(12) United States Patent
Atkinson et al.

(10) Patent No.: US 6,566,118 B1
(45) Date of Patent: May 20, 2003

(54) METHODS FOR GENERATING HIGH TITER HELPER-FREE PREPARATIONS OF RELEASED RECOMBINANT AAV VECTORS

(75) Inventors: Edward M. Atkinson, Seattle, WA (US); Ryan K. Takeya, Lynnwood, WA (US); Ian L. Aranha, Seattle, WA (US)

(73) Assignee: Targeted Genetics Corporation, Seattle, WA (US)

(*) Notice: Subject to any disclaimer, the term of this patent is extended or adjusted under 35 U.S.C. 154(b) by 0 days.

(21) Appl. No.: 09/526,333

(22) Filed: Mar. 15, 2000

Related U.S. Application Data

(63) Continuation-in-part of application No. 09/142,474, filed as application No. PCT/US98/18600 on Sep. 4, 1998, now abandoned, application No. 09/526,333, which is a continuation-in-part of application No. PCT/US99/20524, filed on Sep. 7, 1999, which is a continuation of application No. 09/142,474, filed on Sep. 4, 1998.

(60) Provisional application No. 60/123,385, filed on Mar. 10, 1999, provisional application No. 60/071,733, filed on Jan. 16, 1998, and provisional application No. 60/084,193, filed on Sep. 5, 1997.

(51) Int. Cl.[7] ................................................. C12N 7/02
(52) U.S. Cl. .................. 435/239; 435/235.1; 435/320.1
(58) Field of Search ............................. 435/235.1, 239, 435/320.1

(56) References Cited

U.S. PATENT DOCUMENTS

| | | | |
|---|---|---|---|
| 4,797,368 A | | 1/1989 | Carter et al. |
| 5,173,414 A | | 12/1992 | Leblowki et al. |
| 5,316,938 A | * | 5/1994 | Keen et al. .................. 435/404 |
| 5,436,146 A | | 7/1995 | Shenk et al. |
| 5,474,931 A | * | 12/1995 | DiSorbo et al. ............ 252/380 |
| 5,656,785 A | | 8/1997 | Trainor et al. |
| 5,658,776 A | | 8/1997 | Flotte et al. |
| 5,837,484 A | | 11/1998 | Trempe et al. |
| 5,866,552 A | | 2/1999 | Wilson et al. |

FOREIGN PATENT DOCUMENTS

| | | | |
|---|---|---|---|
| AU | 34470/97 | | 1/1998 |
| EP | WO 97/08298 | * | 6/1997 |
| FR | 2 750 433 | | 1/1998 |
| WO | WO 94/13788 | | 6/1994 |
| WO | WO 95/06743 | | 3/1995 |
| WO | WO 95/13365 | | 5/1995 |
| WO | WO 95/13392 | | 5/1995 |
| WO | WO 95/27071 | | 10/1995 |
| WO | WO 95/34671 | | 12/1995 |
| WO | WO 96/17947 | | 6/1996 |
| WO | WO 96/27677 | | 9/1996 |
| WO | WO 97/06243 | | 2/1997 |
| WO | WO 97/08298 | | 3/1997 |
| WO | WO 97/09441 | | 3/1997 |
| WO | WO 97/17458 | | 5/1997 |
| WO | WO 97/21825 | | 6/1997 |
| WO | WO 97/32990 | | 9/1997 |
| WO | WO 98/09657 A2 | | 3/1998 |
| WO | WO 98/23018 | | 5/1998 |
| WO | WO 98/27204 | | 6/1998 |
| WO | WO 98/27207 | | 6/1998 |
| WO | WO 99/11764 | | 3/1999 |
| WO | WO 00/14205 | | 3/2000 |

OTHER PUBLICATIONS

Tamayose 1996 Human Gene Therapy 7: 507–513.*

Graham (J. Gen. Virol. 1987, vol. 68 pp. 937–940).*

U.S. patent application Ser. No. 09/237,064, Wilson et al., filed Jan. 26, 1999.

U.S. patent application Ser. No. 09/242,977, Wilson et al., filed Feb. 26,1999.

U.S. patent application Ser. No. 09/757,673, Wilson et al., filed Jan. 10, 2001.

Afione, S.A., et al. (May 1996). "In Vivo Model of Adeno–Associated Virus Vector Persistence and Rescue," *J. Virol.* 70(5):3235–3241.

Allen, J.M. (Sep. 1997). "Identification and Elimination of Replication–Competent Adeno–Associated Virus (AAV) That Can Arise by Nonhomologous Recombination During AAV Vector production," *Journal of Virology* 71(9):6816–6822.

Antoni et al. (Jan. 1991). "Adeno–Associated Virus Rep Protein Inhibits Human Immunodeficiency Virus Type 1 Production in Human Cells". *J. Virol.* 65(1):396–404.

(List continued on next page.)

*Primary Examiner*—James Housel
*Assistant Examiner*—Myron G. Hill
(74) *Attorney, Agent, or Firm*—Morrison & Foerster LLP

(57) ABSTRACT

This invention provides methods and compositions for producing high titer, substantially purified preparations of recombinant adeno-associated virus (AAV) that can be used as vectors for gene delivery. At the onset of vector production, AAV producer cells of this invention typically comprise one or more AAV packaging genes, an AAV vector comprising a heterologous (i.e. non-AAV) transgene of interest, and a helper virus such as an adenovirus. The AAV vector preparations produced are generally replication incompetent but are capable of mediating delivery of a transgene of interest (such as a therapeutic gene) to any of a wide variety of tissues and cells. The AAV vector preparations produced according to this invention are also substantially free of helper virus as well as helper viral and cellular proteins and other contaminants. The invention described herein provides methods of producing rAAV particles by culturing producer cells under conditions, such as temperature and pH, that promote release of virus. Also provided is a quantitative, high-throughput assay useful in the assessment of viral infectivity and replication, as well as in the screening of agent that affect viral infectivity and/or replication.

41 Claims, 44 Drawing Sheets

OTHER PUBLICATIONS

Arispe, N. et al. (Mar. 1992). "Intrinsic Anion Channel Activity of the Recombinant First Nucleotide Binding Fold Domain of the Cystic Fibrosis Transmembrane Regulator Protein," *Proc. Natl. Acad. Sci. USA,* Cell Biology 89:1539–1543.

Atkinson, E.M. (1998). "A High–Throughput Hybridization Method for Titer Determination of Viruses and Gene Therapy Vectors," *Nucleic Acids Research* 26(11):2821–2823.

Ausubel, F.M. et al., Eds. (1995). *Current Protocols in Molecular Biology.* John Wiley & Sons, Inc. Vol. I, Table of Contents, Supplement 39, pp. iii–xii.

Bantel–Schaal, U. (1993). "Carcinogen–Induced Accumulation of Adeno–Associated Parvovirus DNA is Transient as a Result of Two Antagonistic Activities That Both Require de novo Protein Synthesis," *Int. J. Cancer* 53:334–339.

Barr, D. et al. (1995). "Strain Related Variations in Adenovirally Mediated Transgene Expression from Mouse Hepatocytes in vivo: Comparisons Between Immunocompetent and Immunodeficient Inbred Strains," *Gene Therapy* 2:151–155.

Berns, K.I. (1990). "Parvoviridae and Their Replication," *Virology.* $2^{nd}$ edition. Raven Press, NY. Chapter 62, pp. 1743–1763.

Bibila, T.A. et al. (1994). "Monoclonal Antibody Process Development Using Medium Concentrates" *Biotechnol. Prog.* 10(1):87–96.

Blacklow, N.R. (1988). "Adeno–Associated Viruses of Humans," *Parvoviruses and Human Disease.* J.R. Pattison, Ed. Chapter 11 pp. 165–174.

Borys, M.C. et al. (Mar. 15, 1994). "Ammonia Affects the Glycosylation Patterns of Recombinant Mouse Placental Lactogen–1 by Chinese Hamster Ovary Cells in a pH–Dependent Manner," *Biotech. Bioeng.* 43(6):505–514.

Byrnes, A.P. et al. (1995). "Adenovirus Gene Transfer Causes Inflammation in the Brain," *Neuroscience* 66(4):1015–1024.

Carter et al. (1979). "Adeno–Associated Virus Autointerference," *Virology* 92:449–462.

Carter, B.J. et al. (1990). "AAV DNA Replication, Integration, and Genetics," *Handbook of Parvoviruses.* vol. I. Chapter 11, pp. 169–226.

Carter, B.J. (1992). "Adeno–Associated Virus Vectors," *Curr. Opin. in Biotech.* 3:533–539.

Carter, B.J. et al. (1992). "Adenovirus Containing a Deletion of the Early Region 2A Gene Allows Growth of Adeno–Associated Virus with Decreased Efficiency," *Virology* 191:473–476.

Chejanovsky et al. (1989). "Mutagenesis of an AUG Codon in the Adeno–Associated Virus rep Gene: Effects on Viral DNA Replication," *Virology* 173:120–128.

Chirico et al. (1998). "Optimization of Packaging of Adeno–Associated Virus Gene Therapy Vectors Using Plasmid Transfections," *J. Viral Methods* 76:31–41.

Clark et al. (1996). "A Stable Cell Line Carrying Adenovirus–Inducible rep and cap Genes Allows for Infectivity Titration of Adeno–Associated Virus Vectors," *Gene Therapy* 3:1124–1132.

Coligan, J.E. et al., Eds. (1998). *Current Protocols in Protein Science.* vols. 1 & 2. John Wiley & Sons, Inc. Table of Contents, pp. 1–6.

Conrad, C.K. et al. (1996). "Safety of Single–Dose Administration of an Adeno–Associated Virus (AAV)–CFTR Vector in the Primate Lung," *Gene Therapy* 3:658–668.

Dorin, G. et al. (1990). "Fractionation of Recombinant Tumor Necrosis Factor Using Hydrophobic and Hydrophilic Membranes," *Biotechnol. Prog.* 6(6):494–497.

Drake, S. et al. (1974). "Complementation of Adeno–Associated Satellite Viral Antigens and Infectious DNA by Temperature–Sensitive Mutants of Herpes Simplex Virus," *Virology* 60:230–236.

Egan, M. et al. (Aug. 13, 1992). "Defective Regulation of Outwardly Rectifying Cl⁻ Channels by Protein Kinase Corrected by Insertion of CFTR," *Nature* 358:581–584.

Ensinger, M.J. et al. (Sep. 1972). "Selection and Preliminary Characterization of Temperature–Sensitive Mutants of Type 5 Adenovirus," *J. Virol.* 10(3):328–339.

Esparza, J. et al. (1974). "Isolation, Complementation and Preliminary Pphenotypic Characterization of Temperature–Sensitive Mutants of Herpes Simplex Virus Type $2^1$," *Virology* 57:554–565.

Fisher, K.J. et al. (Jan. 1996). "Transduction with Recombinant Adeno–Associated Virus for Gene Therapy is Limited by Leading–Strand Synthesis," *Journal of Virology* 70(1):520–532.

Flotte, T.R. et al. (1992). "Gene Expression from Adeno–Associated Virus Vectors in Airway Epithelial Cells," *Am. J. Respir. Cell. Mol. Biol.* 7: 349–356.

Flotte, T.R. et al. (Feb. 15, 1993). "Expression of the Cystic Fibrosis Transmembrane Conductance Regulator from a Novel Adeno–Associated Virus Promoter," *The Journal of Biological Chemistry* 268(5):3781–3790.

Freshney, R.I., Ed. (1987). *Animal Cell Culture: A Practical Approach.* IRL Press, Oxford. Table of Contents, pp. vii–xii.

Ginsberg, H.S. et al. (1974). "Cell transformation: A Study of Regulation with Types 5 and 12 Adenovirus Temperature–Sensitive Mutants," *Cold Spring Harbor Symp. Quant. Biol.* 34:419–426.

Glacken, M.W. et al. (1986). "Reduction of Waste Product Excretion via Nutrient Control: Possible Strategies for Maximizing Product and Cell Yields on Serum in Cultures of Mammalian Cells," *Biotech. Bioeng.* 28:1376–1389.

Glacken, M.W. (Sep. 1988). "Catabolic Control of Mammalian Cell Culture," *Bio/Technology* 6:1041–1043, 1047–1048, 1050.

Graham, F.L. et al. (1991). "Manipulation of Adenovirus Vectors." *Methods in Molecular Biology: Gene Transfer and Expression Protocols.* E.J. Murray, Ed. Humana Press, Clifton, NJ vol. 7. Chapter 11, pp. 109–128.

Handa, H. et al. (1975). "Complementation of Adeno–Associated Virus Growth with Temperature–Sensitive Mutants of Human Adenovirus Types 12 and 5," *J. Gen. Viro.* 29:239–242.

Harrison, T. et al. (1977). "Host–Range Mutants of Adenovirus Type 5 Defective for Growth in HeLa Cells," *Virology* 77:319–329.

Hermonat. P.L. et al. (Oct. 1984). "Use of Adeno–Associated Virus as a Mammalian DNA Cloning Vector: Transduction of Neomycin Resistance into Mammalian Tissue Culture Cells," *Proc. Natl. Acad. Sci. USA* 81:6466–6470.

Horowitz. (1991). "Adenoviridae and Their Replication," *Fundamental Virology.* Fields et al., Eds. 2nd Edition. Raven Press, New York. pp. 771–813.

Huyghe, B.G. et al. (Nov. 1995). "Purification of a Type 5 Recombinant Adenovirus Encoding Human p53 by Column Chromatography," *Human Gene Therapy* 6:1403–1416.

Ishibashi, M. (Feb. 1970). "Retention of Viral Antigen in the Cytoplasm of Cells Infected with Temperature–Sensitive Mutants of an Avian Adenovirus," *Proc. Natl. Acad. Sci. USA* 65(2):304–309.

Ishibashi, M. et al. (1971). "The Potentiation of Type 1 Adeno–Associated Virus by Temperature–Sensitive Conditional–Lethal Mutants of CELO Virus at the Restrictive Temperature," *Virology* 45:317–320.

Ito, M. (1970). "Adeno–Associated Satellite Virus Growth Supported by a Temperature–Sensitive Mutant of Human Adenovirus," *J. Gen. Virol.* 9:243–245.

Laughlin, C.A. et al. (Nov. 1979). "Spliced Adenovirus–Associated Virus RNA," *Proc. Natl. Acad. Sci. USA* 76(11):5567–5571.

Laughlin, C.A. et al. (1983). "Cloning of Infectious Adeno–Associated Virus Genomes in Bacterial Plasmids," *Gene* 23: 65–73.

Lebkowski, J.S. et al. (Oct. 1988). "Adeno–Associated Virus: a Vector System for Efficient Introduction and Integration of DNA into a Variety of Mammalian Cell Types," *Mol. Cell. Biol.* 8(10):3988–3996.

Lundholm, U. et al. (1971). "Temperature–Sensitive Mutants of Human Adenovirus Type 12," *Virology* 45:827–829.

Maiorella, B. et al. (1991). "Crossflow Microfiltration of Animal Cells," *Biotechnol. Bioeng.* 37:121–126.

Matthews P.D. et al. (Jun. 1995). "High–Throughput Microplate Format for Producing and Screening Riboprobes from Bacterial Cells," *Biotechniques* 18(6):1000, 1001, 1004.

Mayor, H.D. et al. (1977). "Complementation of Adeno–Associated Satellite Virus (AAV) by Temperature–Sensitive Mutants of Adenovirus Type 31," *J. Gen Virol.* 35:545–553.

McCoy, R.D. et al. (Dec. 1995). "Pulmonary Inflammation Induced by Incomplete or Inactivated Adenoviral Particles," *Human Gene Therapy* 6:1553–1560.

McLaughlin, S.K. et al. (Jun. 1988). "Adeno–Associated Virus General Transduction Vectors: Analysis of Proviral Structures," *J. Virol.* 62(6):1963–1973.

Miller, J.M. and Calos, M.P., Eds. (1987). "Gene Transfer Vectors for Mammalian Cells," In *Current Communications in Molecular Biology.* Cold Spring Harbor Laboratory Press. Table of Contents, pp. vii–ix.

Muzyczka, N. (1992). "Use of Adeno–Associated Virus as a General Transduction Vector for Mammalian Cells," *Curr. Topics in Microbiol. and Immunol.* 158:97–129.

Myers, M.W. et al. (Jul. 1980). "Adenovirus Helper Function for Growth of Adeno–Associated Virus: Effect of Temperature–Sensitive Mutations in Adenovirus Early Gene Region 2," *J. Virol.* 35(1):65–75.

Ostrove, J.M. et al. (1980). "Adenovirus Early Region 1b Gene Function Required for Rescue of Latent Adeno–Associated Virus," *Virology* 104:502–505.

Paul, R.W. et al. (1993). "Increased Viral Titer Through Concentration of Viral Harvests from Retroviral Packaging Lines," *Human Gene Therapy* 4:609–615.

Peel, A. et al. (1997). "Efficient Transduction of Green Fluorescent Protein in Spinal Cord Neurons Using Adeno–Associated Virus Vectors Containing Cell Type–Specific Promoters," *Gene Therapy* 4:16–24.

Perrin P. et al. (1995). "An Experimental Rabies Vaccine Produced with a New BHK–21 Suspension Cell Culture Process: Use of Serum–Free Medium and Perfusion–Reactor System," *Vaccine* 13(13):1244–1250.

Prior, C. et al. (Apr. 1995). "Process Development for the Manufacture of Inactivated HIV–1," *Pharmaceut. Technol.* 19:30, 32, 34, 36, 38, 40, 42, 44, 46, 48, 50, 52.

Rich, D.P. et al. (Jul. 12, 1991). "Effect of Deleting the R Domain on CFTR–Generated Chloride Channels," *Science* 253:205–207.

Roovers, D.J. et al. (1990). "Physical Mapping of Two Temperature–Sensitive Adenovirus Mutants Affected in the DNA Polymerase and DNA Binding Protein," *Virus Genes* 4(1):53–61.

Rose, J.A. (1974). "Parvovirus Reproduction," *Comprehensive Virology.* Chapter 1, pp. 1–61.

Russel, D.W. et al. "Adeno–Associated Virus Vectors Preferentially Transduce Cells in S Phase," *Proc. Natl. Acad. Sci. USA* Medical Sciences 91:8915–8919.

Sambrook, J. et al. (1989). *Molecular Cloning: A Laboratory Manual.* Second edition. Cold Spring Harbor Laboratory Press. Table of Contents, pp. xi–xxxviii.

Samulski, R.J. et al. (Mar. 1982). "Cloning of Adeno–Associated Virus into pBR322:Rescue of Intact Virus from the Recombinant Plasmid in Human Cells," *Proc. Natl. Acad. Sci. USA,* 79:2077–2081.

Samulski, R.J. et al. (Sep. 1989). "Helper–Free Stocks of Recombinant Adeno–Associated Viruses: Normal Integration Does not Require Viral Gene Expression," *J. Virol.* 63(9):3822–3828.

Schaffer, P.A. et al. (1973). "Temperature–Sensitive Mutants of Herpes Simplex Virus Type 1: Isolation, Complementation and Partial Characterization," *Virology* 52: 57–71.

Schlehofer, J.R. et al. (1986). "Vaccinia Virus, Herpes Simplex Virus, and Carcinogens Induce DNA Amplication in a Human Cell Line and Support Replication of a Helpervirus Dependent Parvovirus," *Virology* 152:110–117.

Scopes, R.K., Ed. (1994). *Protein Purification: Principles and Practice.* 2nd Edition Springer–Verlag. Table of Contents, pp. 13–15.

Senapathy, P. et al. (Apr. 10, 1984). "Molecular Cloning of Adeno–Associated Virus Variant Genomes and Generation of Infectious Virus by Recombination in Mammalian Cells," *J. Biol. Chem.* 259(7):4661–4666.

Sheppard, D.N. et al. (Mar. 25, 1994). "The Amino–Terminal Portion of CFTR Forms a Regulated Cl⁻ Channel," *Cell* 76:1091–1098.

Shiroki, K. et al. (1974). "Analysis of Adenovirus 12 Temperature–Sensitive Mutants Defective in Viral DNA Replication," *Virology* 61:474–485.

Straus, S.E. et al. (Jan. 1976). "DNA–Minus Temperature–Sensitive Mutants of Adenovirus Type 5 Help Adenovirus–Associated Virus Replication," *J. Virol.* 17(1):140–148.

Straus, S.E. et al. (Mar. 1976). "Concatemers of Alternating Plus and Minus Strands are Intermediates in Adenovirus–Associated Virus DNA Synthesis," *Proc. Natl. Acad. Sci. USA,* 73(3):742–746.

Tamayose, K. et al. (Mar. 1, 1996). "A New Strategy for Large–Scale Preparation of High–Titer Recombinant Adeno–Associated Virus Vectors by Using Packaging Cell Lines and Sulfonated Cellulose Column Chromatography," *Human Gene Therapy* 7:507–513.

Tratschin, J.D. et al. (Oct. 1984). "A human Parvovirus, Adeno–Associated Virus, as a Eucaryotic Vector: Transient Expression and Encapsidation of the Procaryotic Gene for Chloramphenicol Acetyltransferase," *Mol. Cell. Biol.* 4(10):2072–2081.

Tratschin, J.D. et al. (Nov. 1985). "Adeno–Associated Virus Vector for High–Frequency Integration, Expression, and Rescue of Genes in Mammalian Cells," *Mol. Cell. Biol.* 5(11):3251–3260.

Tratschin, J.D. et al. (Aug. 1986). "Negative and Positive Regulation in trans of Gene Expression from Adeno–Associated Virus Vectors in Mammalian Cells by a Viral rep Cene Product," *Mol. Cell Biol.* 6(8):2884–2894.

Waye, J.S. et al. (1987). "Genomic Organization of Alpha Satellite DNA on Human Chromosome 7: Evidence for Two Distinct Alphoid Domains on a Single Chromosome," *Mol. Cell. Biol.* 7:349–356.

Williams, J.F. et al. (1971). "Isolation of Temperature–Sensitive Mutants of Adenovirus Type 5," *J. Gen Virol.* 11:95–101.

Yakobson, B. et al. (Apr. 1987). "Replication of Adeno–Associated Virus in Synchronized Cells Without the Addition of a Helper Virus," *Journal of Virology* 61(4):972–981.

Yakobson, B. et al. (Mar. 1989). "Replication of Adeno–Associated Virus in Cells Irradiated with UV Light at 254 nm," *Journal of Virology* 63(3):1023–1030.

Yalkinoglu, A. Ö. et al. (Jun. 1, 1988). "DNA Amplification of Adeno–Associated Virus as a Response to Cellular Genotoxic Stress," *Cancer Research* 48:3123–3129.

\* cited by examiner-

Fig. 26A

| Lactalbumun Hydrolysate w/Earle's Salts (ELH) | | |
|---|---|---|
| Base Cat No. | 11250 1XLiquid mg/L | 11800 Powder mg/L |
| Component | | |
| INORGANIC SALTS: | | |
| CaCl₂ (anhyd.) | 200.00 | 200.00 |
| KCl | 400.00 | 400.00 |
| MgSO₄ (anhyd.) | 97.67 | 97.70 |
| NaCl | 6800.00 | 6800.00 |
| NaHCO₃ | 2200.00 | — |
| NaH₂PO₄·H₂O | 140.00 | 140.00 |
| OTHER COMPONENTS: | | |
| D-Glucose | 1000.00 | 1000.00 |
| Lactalbumin Hydrolysate | 6500.00 | 5000.00 |
| Phenol Red | 10.00 | 10.00 |

| MEM Amino Acids Solutions[2] | | |
|---|---|---|
| Base Cat No. | 11136 | 21135 |
| Component | 50X Liquid mg/L | 50X Liquid mg/L |
| AMINO ACIDS: | | |
| L-Arginine | 6320.00 | 6320.00 |
| L-Cystine | 1200.00 | 1200.00 |
| L-Glutamine | — | 14600.00 |
| L-Histidine-HCL-H₂O | 2100.00 | 2100.00 |
| L-Isoleucine | 2625.00 | 2625.00 |
| L-Luecine | 2620.00 | 2620.00 |
| L-Lysins HCL | 3625.00 | 3625.00 |
| L-Methionine | 755.00 | 755.00 |
| L-Phenylalhine | 1650.00 | 1650.00 |
| L-Threonine | 2380.00 | 2380.00 |
| L-Tryptophan | 510.00 | 510.00 |
| L-Tyrosine | 1800.00 | 1800.00 |
| L-Valine | 2340.00 | 2340.00 |

References:
1. Eagle, H. (1955) Proc. Soc. Exp. Biol. Med. 89, 362.
2. Eagle, H. (1959) Science 130, 432

| MEM Non-Essential Amino Acids Solution[2] | |
|---|---|
| Base Cat No. | 11140 100X Liquid mg/L |
| Component | |
| AMINO ACIDS: | |
| L-Algnine | 890.00 |
| L-Asparagine | 1500.00 |
| L-Aspartic | 1330.00 |
| L-Glutamine | 1470.00 |
| Glycine | 750.00 |
| L-Proline | 1150.00 |
| L-Serine | 1050.00 |

| MEM Vitamon Solutions[2] | |
|---|---|
| Base Cat No. | 11120 50X Liquid mg/L |
| Component | |
| NaCl | 8500.00 |
| D-Ca Pantothenate | 100.00 |
| Choline Chloride | 100.00 |
| Folic Acid | 100.00 |
| I-Inositol | 200.00 |
| Nicotinamide | 100.00 |
| Pyridoxal-HCL | 100.00 |
| Riboflavin | 10.00 |
| Thiamine HCL | 100.00 |

Fig. 26B

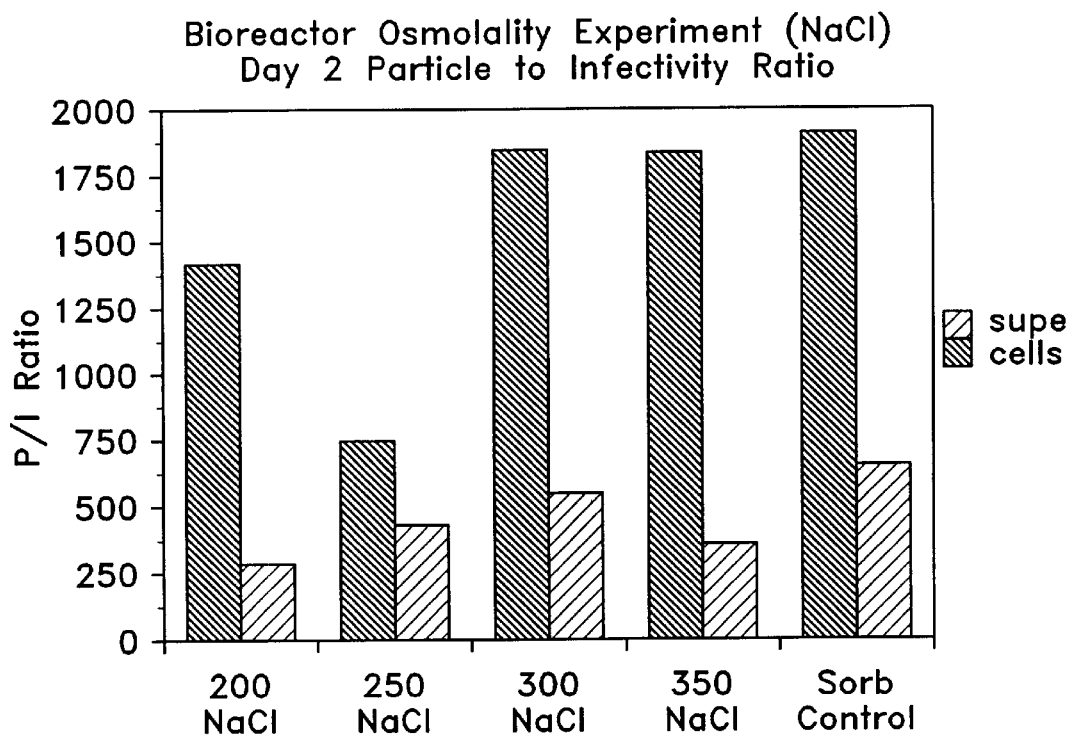
Fig. 37A
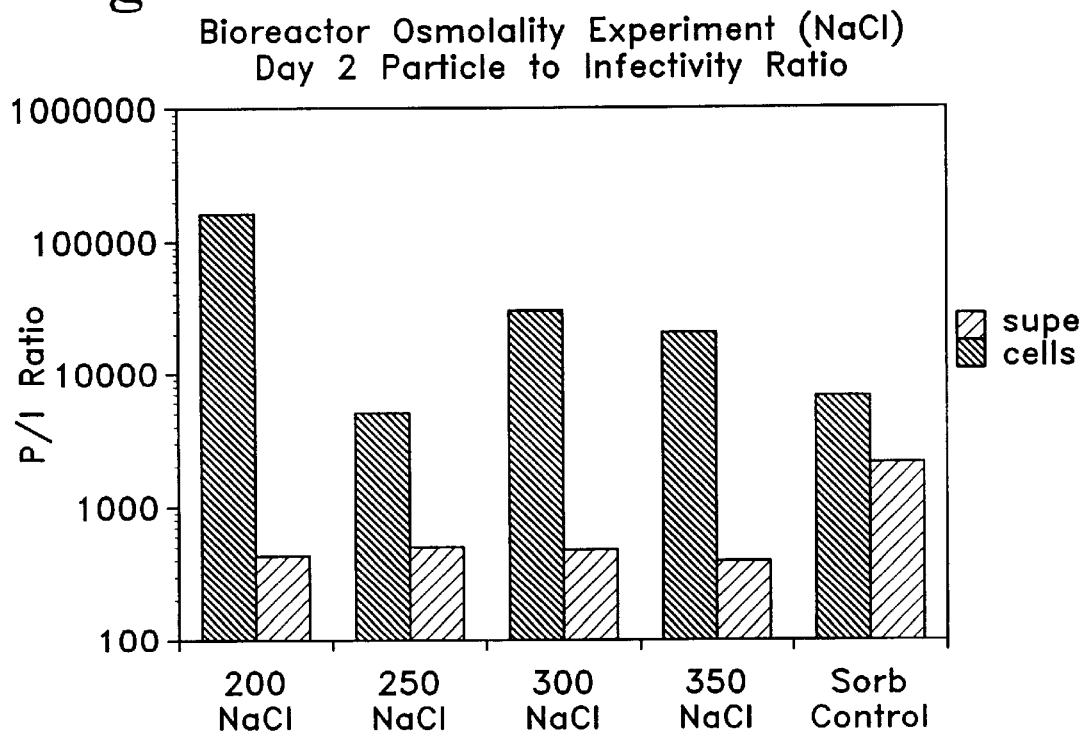
Fig. 37B  *Base dump between day 2 and day 3

METHODS FOR GENERATING HIGH TITER HELPER-FREE PREPARATIONS OF RELEASED RECOMBINANT AAV VECTORS

CROSS-REFERENCE TO RELATED APPLICATIONS

This is a continuation-in-part of U.S. Ser. No. 09/142,474, filed Sep. 4, 1998, which was a U.S. National filing under Section 371 (via PCT application PCT/US98/18600, filed Sep. 4, 1998), which claims the priority benefit of provisional U.S. Ser. Nos. 60/071,733, filed Jan. 16, 1998, and 60/084,193, filed Sep. 5, 1997. This application also is a continuation-in-part of PCT patent application PCT/US99/20524 filed Sep. 7, 1999, designating the U.S., which claims priority to provisional application U.S. Ser. No. 20 60/1 23,685, filed Mar. 10, 1999 and is a continuation of U.S. Ser. No. 09/142,474, filed Sep.4, 1998 now ABN. All of these applications are incorporated by reference in their entirety.

STATEMENT OF RIGHTS TO INVENTIONS MADE UNDER FEDERALLY SPONSORED RESEARCH

This invention was made in part during work supported by a grant from the National Institutes of Health (NIH) R44DK4460. The government may have certain rights in this invention.

TECHNICAL FIELD

The present invention relates generally to the field of-recombinant adeno-associated virus (AAV) vectors and preparations thereof that can be used for gene transfer. More specifically, it relates to methods for generating high titer preparations of recombinant AAV vectors that are substantially free of helper virus (e.g. adenovirus) as well as cellular proteins.

BACKGROUND ART

Adeno-associated viruses (AAV) have unique features that make them attractive as vectors for gene therapy. Adeno-associated viruses infect a wide range of cell types. However, they are non-transforming, and are not implicated in the etiology of any human disease. Introduction of DNA to recipient host cells generally leads to long-term persistence and expression of the DNA without disturbing the normal metabolism of the cell.

There are at least three desirable features of a recombinant AAV vector preparation for use in gene transfer, especially in human gene therapy. First, it is preferred that the vector should be generated at titers sufficiently high to transduce an effective proportion of cells in the target tissue. Gene therapy in vivo typically requires a high number of vector particles. For example, some treatments may require in excess of $10^8$ particles, and treatment of cystic fibrosis by direct delivery to the airway may require in excess of $1^{10}$ particles. Second, it is preferred that the vector preparations should be essentially free of replication-competent AAV (i.e. phenotypically wild-type AAV which can be replicated in the presence of helper virus or helper virus functions). Third, it is preferred that the rAAV vector preparation as a whole be essentially free of other viruses (such as a helper virus used in AAV production) as well as helper virus and cellular proteins, and other components such as lipids and carbohydrates, so as to minimize or eliminate any risk of generating an immune response in the context of gene therapy. This latter point is especially significant in the context of AAV because AAV is a "helper-dependent" virus that requires co-infection with a helper virus (typically adenovirus) or other provision of helper virus functions in order to be effectively replicated and packaged during the process of AAV production; and, moreover, adenovirus has been observed to generate a host immune response in the context of gene therapy applications (see, e.g., Byrnes et al., Neuroscience 66:1015, 1995; McCoy et al., Human Gene Therapy 6:1553, 1995; and Barr et al., Gene Therapy 2:151, 1995). The methods of the present invention address these and other desirable features of rAAV vector preparations, as described and illustrated in detail below.

General reviews of AAV virology and genetics are available elsewhere. The reader may refer inter alia to Carter, "Handbook of Parvoviruses", Vol. I pp. 169–228 (1989), and Berns, "Virology", pp. 1743–1764, Raven Press, (1990). AAV is a replication-defective virus, which means that it relies on a helper virus in order to complete its replication and packaging cycle in a host cell. Helper viruses capable of supporting AAV replication are exemplified by adenovirus, but include other viruses such as herpes and pox viruses. The AAV genome generally comprises the packaging genes rep and cap, with other necessary functions being provided in trans from the helper virus and the host cell.

AAV particles are comprised of a proteinaceous capsid having three capsid proteins, VP1, VP2 and VP3, which enclose a ~4.6 kb linear single-stranded DNA genome. Individual particles package only one DNA molecule strand, but this may be either the plus or minus strand. Particles containing either strand are infectious, and replication occurs by conversion of the parental infecting single strand to a duplex form, and subsequent amplification, from which progeny single strands are displaced and packaged into capsids. Duplex or single-strand copies of AAV genomes (sometimes referred to as "proviral DNA" or "provirus") can be inserted into bacterial plasmids or phagemids, and transfected into adenovirus-infected cells.

By way of illustration, the linear genome of serotype AAV2 is terminated at either end by an inverted terminal repeat (ITR) sequence. Between the ITRs are three transcription promoters p5, p19, and p40 that are used to express the rep and cap genes (Laughlin et al., 1979, Proc. Natl. Acad. Sci. USA, 76:5567–5571). ITR sequences are required in cis and are sufficient to provide a functional origin of replication, integration into the cell genome; and efficient excision and rescue from host cell chromosomes or recombinant plasmids. The rep and cap gene products provide functions for replication and encapsidation of viral genome, respectively, and it is sufficient for them to be present in trans.

The rep gene is expressed from two promoters, p5 and p 19, and produces four proteins designated Rep78, Rep68, Rep52 and Rep40. Only Rep78 and Rep68 are required for AAV duplex DNA replication, but Rep52 and Rep40 appear to be needed for progeny, single-strand DNA accumulation (Chejanovsky et al., Virology 173:120, 1989). Rep68 and Rep78 bind specifically to the hairpin conformation of the AAV ITR and possess several enzyme activities required for resolving replication at the AAV termini. Rep78 and Rep68, also exhibit pleiotropic regulatory activities including positive and negative regulation of AAV genes and expression from some heterologous promoters, as well as inhibitory effects on cell growth. The cap gene encodes capsid proteins VP1, VP2, and VP3. These proteins share a common overlapping sequence, but VP1 and VP2 contain additional amino terminal sequences transcribed from the p40 promoter by use of alternate initiation codons. All three proteins are required for effective capsid production.

AAV genomes have been introduced into bacterial plasmids by procedures such as GC tailing (Samulski et al., 1982, Proc. Natl. Acad. Sci. USA, 79:2077–2081), addition of synthetic linkers containing restriction endonuclease cleavage sites (Laughlin et al., 1983, Gene, 23:65–73) or by direct, blunt-end ligation (Senapathy & Carter, 1984, J. Biol. Chem., 259:4661–4666). Transfection of such AAV recombinant plasmids into mammalian cells with an appropriate helper virus results in rescue and excision of the AAV genome free of any plasmid sequence, replication of the rescued genome and generation of progeny infectious AAV particles.

Recombinant AAV vectors comprising a heterologous polynucleotide of therapeutic interest may be constructed by substituting portions of the AAV coding sequence in bacterial plasmids with the heterologous polynucleotide. General principles of rAAV vector construction are also reviewed elsewhere. See, e.g., Carter, 1992, Current Opinions in Biotechnology, 3:533–539; and Muzyczka, 1992, Curr. Topics in Microbiol. and Immunol., 158:97–129). The AAV ITRs are generally retained, since packaging of the vector requires that they be present in cis. However, other elements of the AAV genome, in particular, one or more of the packaging genes, may be omitted. The vector plasmid can be packaged into an AAV particle by supplying the omitted packaging genes in trans via an alternative source.

In one approach, the sequence flanked by AAV ITRs (the rAAV vector sequence), and the AAV packaging genes to be provided in trans, are introduced into the host cell in separate bacterial plasmids. Examples of this approach are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822–3828) have described a packaging plasmid called pAAV/Ad, which consists of Rep and Cap encoding regions enclosed by ITRs from adenovirus. Human airway epithelial cells from a cystic fibrosis patient have been transduced with an AAV vector prepared using the pAAV/Ad packaging plasmid and a plasmid comprising the selective marker gene neo expressed via the AAV p5 promoter (Flotte et al., Am. J. Respir. Cell. Mol. Biol. 7:349, 1992).

A second approach is to provide either the vector sequence, or the AAV packaging genes, in the form of an episomal plasmid in a mammalian cell used for AAV replication. For example, U.S. Pat. No. 5,173,414 describes a cell line in which the vector sequence is present as a high-copy episomal plasmid. The cell lines can be transduced with the trans-complementing AAV functions rep and cap to generate preparations of AAV vector. This approach is not ideal, because the copy number per cell cannot be rigorously controlled and episomal DNA is much more likely to undergo rearrangement, leading to production of vector byproducts.

A third approach is to provide either the vector sequence, or the AAV packaging genes, or both, stably integrated into the genome of the mammalian cell used for replication.

One exemplary technique is outlined in international patent application WO 95/13365 (Targeted Genetics Corporation and Johns Hopkins University) and corresponding U.S. Pat. No. 5,658.776 (by Flotte et al.). This example uses a mammalian cell with at least one intact copy of a stably integrated rAAV vector, wherein the vector comprises an AAV ITR and a transcription promoter operably linked to a target polynucleotide, but wherein the expression of rep is limiting. In a preferred embodiment, an AAV packaging plasmid comprising the rep gene operably linked to a heterologous AAV is introduced into the cell, and then the cell is incubated under conditions that allow replication and packaging of the AAV vector sequence into particles.

A second exemplary technique is outlined in patent application WO 95/13392 (Trempe et al.). This example uses a stable mammalian cell line with an AAV rep gene operably linked to a heterologous promoter so as to be capable of expressing functional Rep protein. In various preferred embodiments, the AAV cap gene can be provided stably as well or can be introduced transiently (e.g. on a plasmid). A recombinant AAV vector can also be introduced stably or transiently.

Another exemplary technique is outlined in patent application WO 96/17947 (by Targeted Genetics Corporation, J. Allen). This example uses a mammalian cell which comprises a stably integrated AAV cap gene, and a stably integrated AAV rep gene operably linked to a heterologous promoter and inducible by helper virus. In various preferred embodiments, a plasmid comprising the vector sequence is also introduced into the cells (either stably or transiently). The rescue of AAV vector particles is then initiated by introduction of the helper virus.

Other methods for generating high-titer preparations of recombinant AAV vectors have been described. International Patent Application No. PCT/US98/18600 describes culturing a cell line which can produce rAAV vector upon infection with a helper virus; infecting the cells with a helper virus, such as adenovirus; and lysing the cells. AAV and other viral production methods and systems are also described in, for example, WO 97/09441 (PCT/US96/14423); WO 97/08298 (PCT/US96/13872); WO 97/21825 (PCTIUS96/20777); WO 97/06243 (PCT/FR96/01064); WO 99/11764; Perrin et al. (1995) Vaccine 13:1244–1250; Paul et al. (1993) Human Gene Therapy 4:609–615; Clark et al. (1996) Gene Therapy 3:1124–1132.

These various examples address the issue of providing AAV at sufficiently high titer, minimizing recombination between vector and packaging components, and reducing or avoiding the potential difficulties associated with the expression of the AAV rep gene in mammalian cell line (since the Rep proteins can not only limit their own expression but can also affect cellular metabolism). However, packaging of an AAV vector into viral particles still relies on the presence of a suitable helper virus for AAV or the provision of helper virus functions. Helper viruses capable of supporting AAV replication are exemplified by adenovirus, but include other viruses such as herpes and pox viruses. The presence of significant quantities of infectious helper virus in a preparation of AAV vectors is problematic in that the preparation is intended for use in human administration. Even the presence of non-replicative helper virus components can cause an unacceptable immunological reaction in the treated subject.

The potential problems elicited by helper virus antigen have been illustrated in several recent studies. Byrnes et al. (Neuroscience 66:1015, 1995) injected an E1-region deleted, non-replicating human adenovirus type 5 into the brains of inbred rats. An inflammatory response was observed that was attributed to the particles administered rather than to expression of new viral proteins due to viral replication in the cells. Presence of the virus was associated with an increase in MHC Class I gene expression and a heavy infiltration of macrophages and T cells. McCoy et al. (Human Gene Therapy 6:1553, 1995) instilled the lungs of mice with intact adenovirus, adenovirus with incomplete genomes, or adenovirus inactivated with ultraviolet light. All induced pulmonary inflammation, and the number of inflammatory cells in the lung tissue was quantitatively similar for all three forms of the virus. Comparative experiments using adenovirus constructs in normal and immune-deficient mice performed by Barr et al. (Gene Therapy 2:151, 1995) indicate that the anti-adenovirus immune response is primarily T-cell mediated and gives rise to a memory response that affects subsequent doses.

Accordingly, in the development of recombinant AAV vectors such as those for use in gene therapy, there is a need for strategies that minimize the amount of helper virus, as well as helper virus proteins and cellular proteins, present in the final preparation, while at the same time still achieving a high titer of AAV so that the methods can be effectively employed on a scale that is suitable for the practical application of gene therapy techniques.

Since high titers of rAAV vector preparations are particularly useful, but the production of high titers of rAAV, particularly in large-scale procedures, can lead to the generation of significant quantities of contaminating helper virus (e.g. adenovirus or "Ad"), helper virus proteins (e.g. Ad proteins), and/or cellular proteins, it became especially important to design scalable methods for the production of rAAV that can be used for the generation of high-titer preparations that are substantially free of contaminating virus and/or viral or cellular proteins.

Prior art methods used to produce recombinant AAV particle using packaging cells required a cell lysis step due to the pervasive belief that AAV is not released from producer cells in any appreciable amount without lysing the cells. See, for example, Chirico and Trempe (1998) J. Viral. Methods 76:31–41. However, the cell lysate contains various cellular components which must be separated from the rAAV vector before it is suitable for in vivo use.

The present disclosure provides methods for achieving high-titer production of rAAV vectors, including rAAV released from a producer cell without lysing the cell(s), and demonstrates that such techniques can be employed for the large-scale production of recombinant AAV vector preparations.

SUMMARY OF THE INVENTION

This invention provides methods and materials for generating high titer preparations of adeno-associated virus (AAV) that are substantially free of helper virus, helper virus proteins, and cellular proteins and other components. These methods entail upstream processing (such as growth in suspension and/or under conditions that permit release of virus) as well as downstream processing (such as chromatography). The upstream and downstream methods may be used alone or in various combinations.

Accordingly, in one aspect, the invention provides methods of generating a population of rAAV particles comprising the step of: incubating a producer cell in a cell culture medium, wherein said producer cell is cultured under suspension conditions, whereby greater than about $10^2$ particles are produced from the producer cell. In some embodiments, tangential flow filtration is employed to purify the population of virus produced (with or without other steps and conditions as described herein).

In another aspect, the invention provides methods for generating a population of recombinant adeno-associated virus (rAAV) particles, comprising the step of: incubating an AAV producer cell under conditions that are permissive for replication of AAV, said producer cell comprising (i) one or more AAV packaging genes wherein each said AAV packaging gene encodes an AAV replication or encapsidation protein; (ii) a recombinant AAV (rAAV) vector that comprises a heterologous non-AAV polynucleotide flanked by at least one AAV inverted terminal repeat (ITR); and (iii) a helper virus for AAV, wherein said helper virus is a temperature-sensitive helper virus, wherein the incubating the producer cell line is conducted at a temperature that is permissive for replication of AAV but non-permissive for replication of the temperature-sensitive helper virus, whereby AAV virus particles are produced. In some embodiments, the incubation occurs for at least five days from the time of introduction of the temperature-sensitive adenovirus. In some embodiments, the temperature sensitive helper virus is adenovirus Ad-ts149. The temperature-sensitive helper virus may be in the form of a virus particle or plasmid. In some embodiments, rAAV production is increased at least about 5-fold as compared to rAAV production using a wild type adenovirus.

In another aspect, the invention provides methods for isolating a population of rAAV particles, comprising the steps of: (a) chromatographing an AAV producer cell lysate containing rAAV particles on a positively-charged anion exchange resin (i.e., at least one positively-charged anion exchange resin); and (b) chromatographing an AAV producer cell lysate containing rAAV particles on a negatively-charged cation exchange resin (i.e., at least one negatively charged cation exchange resin), whereby a purified population of rAAV particles is generated. The steps may be performed in either order. In some embodiments, an additional step of subjecting the producer cells to tangential flow filtration is performed. In some embodiments, an additional step of subjecting the lysate to tangential flow filtration, which can be before and/or after performing chromatography. These methods are applicable to cells which are adherent or cells which are grown in suspension.

In another aspect, the invention provides methods for isolating a population of rAAV particles, comprising the steps of: (a) chromatographing AAV producer cell culture supernatant which contains rAAV particles on a positively-charged anion exchange resin; and (b) chromatographing the AAV producer cell culture supernatant containing rAAV particles on a negatively-charged cation exchange resin, whereby a purified population of rAAV particles is generated. The steps may be performed in either order. In some embodiments, an additional step of subjecting the supernatant to tangential flow filtration is performed, which may be before and/or after chromatography. These methods are applicable to cells which are adherent or cells which are grown in suspension.

In another aspect, the invention provides methods for isolating rAAV particles comprising the steps of (a) chromatographing an AAV producer cell lysate containing rAAV particles on a positively charged anion exchange resin; and (b) subjecting the product of step a to tangential flow filtration to generate a purified population of rAAV. The steps may be performed in either order. These methods are applicable to cells which are adherent or cells which are grown in suspension.

In another aspect, the invention provides methods for isolating rAAV particles comprising the steps of (a) chromatographing an AAV producer cell culture supernatant which contains rAAV particles on a positively charged anion exchange resin; and (b) subjecting the product of step a to tangential flow filtration to generate a purified population of rAAV. The steps may be performed in either order. These methods are applicable to cells which are adherent or cells which are grown in suspension.

In another aspect, the invention provides methods for generating a population of rAAV particles comprising culturing a producer cell under a stress condition, said producer cell comprising (i) one or more AAV packaging genes, wherein each said AAV packaging gene encodes an AAV replication or encapsidation protein; (ii) a recombinant AAV (rAAV) vector that comprises a heterologous non-AAV polynucleotide flanked by at least one AAV inverted terminal repeat (ITR); and (iii) helper virus function for AAV, whereby about two-fold or more rAAV particles are produced compared to a producer cell not grown under said stress condition. Examples of stress conditions are provided herein. These methods are applicable to cells which are adherent or cells which are grown in suspension.

Other embodiments of the invention include but are not limited to the following:

A method of generating a population of recombinant adeno-associated virus (rAAV) particles, comprising the steps of: a) providing an AAV producer cell that comprises: (i) one or more AAV packaging genes, wherein each said AAV packaging gene encodes an AAV replication or encapsidation protein; (ii) a recombinant AAV (rAAV) pro-vector that comprises a heterologous non-AAV polynucleotide flanked by at least one AAV inverted terminal repeat (ITR); and (iii) a helper virus for AAV; b) incubating the producer cell provided in step a) under conditions that are permissive for replication of AAV; c) lysing the producer cell after the incubation of step b) to produce an AAV producer cell lysate; and d) chromatographing the AAV producer cell lysate of step c) on a plurality of ion-exchange resins comprising at least one positively-charged anion exchange resin and at least one negatively-charged cationic exchange resin to generate a purified population of rAAV vector particles, or chromatographing the AAV producer cell lysate of step c) on an anion exchange resin followed by tangential flow filtration (TFF).

A method of generating a population of rAAV particles, wherein said helper virus is an adenovirus or a temperature-sensitive helper virus, and said step of incubating the producer cell is conducted at a temperature that is permissive for replication of AAV but non-permissive for replication of the temperature-sensitive helper virus.

A method of generating a population of rAAV particles, wherein incubating the producer cell is conducted in a vessel selected from the group consisting of a tissue culture flask, a roller bottle, a spinner flask, a tank reactor, a fermentor, and a bioreactor, optionally using a microcarrier, and preferably using a suspension-adapted mammalian cell line.

A method of generating a population of recombinant adeno-associated virus (rAAV) particles, comprising the steps of: a) providing an AAV producer cell that comprises: (i) one or more AAV packaging genes, wherein each said AAV packaging gene encodes an AAV replication or encapsidation protein; (ii) a recombinant AAV (rAAV) pro-vector that comprises a heterologous non-AAV polynucleotide flanked by at least one AAV inverted terminal repeat (ITR); and (iii) a helper virus for AAV or a polynucleotide sequence of said helper virus that encodes at least one helper virus function; b) subjecting the producer cell provided in step a) to a sub-lethal stress; and c) incubating the stressed producer cell of step b) under conditions that are permissive for replication of AAV. Possible forms of sub-lethal stress may be selected but are not limited to those in the group consisting of a nutritional stress, an osmotic stress, a pH stress, a temperature stress, an aerobic stress, a mechanical stress, a radiational stress and a toxic stress. A non-limiting example by which nutritional stress is imposed is by culturing the producer cells in a medium that is deficient in one or more amino acids. Additional illustrations are provided below.

A method of generating a population of rAAV particles, wherein said purified population of rAAV vector particles is substantially free of replication-competent AAV and of helper virus and cellular proteins.

A method of generating a population of recombinant adeno-associated virus (rAAV) particles, comprising the steps of: a) providing an AAV producer cell that comprises: (i) one or more AAV packaging genes, wherein each said AAV packaging gene encodes an AAV replication or encapsidation protein; (ii) a recombinant AAV (rAAV) pro-vector that comprises a heterologous non-AAV polynucleotide flanked by at least one AAV inverted terminal repeat (ITR); and (iii) a helper virus for AAV; b) incubating the producer cell provided in step a) under conditions that are permissive for replication of AAV and which comprise inducing a sub-lethal stress in the AAV producer cell; c) lysing the producer cell after the incubation of step b) to produce an AAV producer cell lysate; and d) purifying the AAV producer cell lysate to generate a population of recombinant adeno-associated virus (rAAV) particles. Suitable purification methods include those described elsewhere in this disclosure. An exemplary purification procedure comprises chromatographing the AAV producer cell lysate of step c) on at least one chromatographic resin selected from the group consisting of a positively-charged anion exchange resin and a negatively-charged cationic exchange resin to generate a purified population of rAAV vector particles (preferred methods include anion exchange followed by cation exchange or tangential flow filtration (TFF)). Illustrative chromatographic procedures, including ion exchange chromatography, and chromatographic purification on heparin sulfate are provided below by way of example.

A host cell for producing recombinant adeno-associated virus (rAAV) particles at high efficiency, comprising: a) one or more AAV packaging genes, wherein each said AAV packaging gene encodes an AAV replication or encapsidation protein; b) a heterologous polynucleotide introduced into said host cell using an rAAV pro-vector, wherein the rAAV pro-vector comprises the heterologous polynucleotide flanked by at least one AAV inverted terminal repeat (ITR) and is deficient in said AAV packaging gene(s); c) a helper virus such as a temperature-sensitive helper virus (tsHV) for AAV, wherein said tsHV is temperature-sensitive for self-replication.

In other embodiments, the methods entail release of rAAV particle from producer cells without actively lysing the cells as is typical in the art, which provides a distinct and significant advantage over previously described production methods. The methods are also applicable to viruses which are non-lytic and/or generally not released (i.e., non-budding viruses).

Accordingly, in one aspect, the invention provides methods of generating a population of virus particles, such as recombinant adeno-associated virus (rAAV) particles, comprising the step of: a) incubating a producer cell in a cell culture medium under conditions which promote release of AAV particles from the cell, whereby rAAV particles are released from the producer cell into the culture medium, and wherein the producer cell comprises (i) one or more AAV packaging genes, wherein each said AAV packaging gene encodes an AAV replication or encapsidation protein; (ii) a recombinant AAV (rAAV) vector that comprises a heterologous non-AAV polynucleotide flanked by at least one AAV inverted terminal repeat (ITR); and (iii) a helper virus for AAV or helper virus function for AAV. The released rAAV particles may then be collected, or harvested, from the culture medium. Conditions which promote release of rAAV viral particles are described herein and include, but are not limited to, pH, osmolality, dissolved oxygen, enriched media, and temperature.

In some embodiments, the methods further include various purification and/or inactivation steps. In some of these embodiments, the method further comprises the steps of: chromatographing the AAV producer cell supernatant on a plurality of ion-exchange resins comprising at least one positively-charged anion exchange resin and at least one negatively-charged cationic exchange resin to generate a purified population of rAAV vector particles, or chromatographing the AAV producer cell supernatant on an anion exchange resin followed by tangential flow filtration (TFF). Heparin sulphate chromatography can also be used as a cation exchange resin to further purify the virus.

In the methods of the invention, cell culture can be carried out such that the cells are in suspension or under conditions that promote adherence of cells to a solid support. Accordingly, in some embodiments, the producer cell is cultured in a vessel selected from the group consisting of a tissue culture flask, a roller bottle, a spinner flask, a tank reactor, a fermentor, and a bioreactor, a flat stock reactor, a hollow fiber system, a packed bed reactor and optionally using a microcarrier.

In some embodiments of the invention, recombinant AAV vector preparations produced by the methods result in a purified population of rAAV vector particles which is substantially free of replication-competent AAV and of helper virus and cellular proteins as well as substantially free cellular DNA.

The present invention further provides a population of rAAV particles, produced according to any of the production methods of this invention. Preferably, the population of particles contains no more than about one infectious adenovirus particles per thousand infectious rAAV particles, preferably less than one per $10^6$ rAAV, still more preferably less than about one in $10^9$, even more preferably less than about one in $10^{10}$.

Also provided are high-throughput assay techniques which can be used, for example, in the titering of virus preparations as well as in the screening of agents that affect viral infectivity and/or replication.

These and other embodiments of the invention are outlined in the description that follows.

DESCRIPTION OF THE DRAWINGS

FIGS. 26A and 26B provides amino acid and vitamin compositions for the media supplements described in Example 17.

FIGS. 37A–D are bar graphs depicting P/I ratios of rAAV particles in cell lysates (solid bars) and cell culture media (hatched bars) on day 2 (FIGS. 37A and 37C) and day 3 (FIGS. 37B and 37D) post infection in bioreactors for media formulated at the indicated starting osmolality with NaCl (FIGS. 37A and 37B) or sorbitol (FIGS. 37C and D).

MODES FOR CARRYING OUT THE INVENTION

Figure 1:
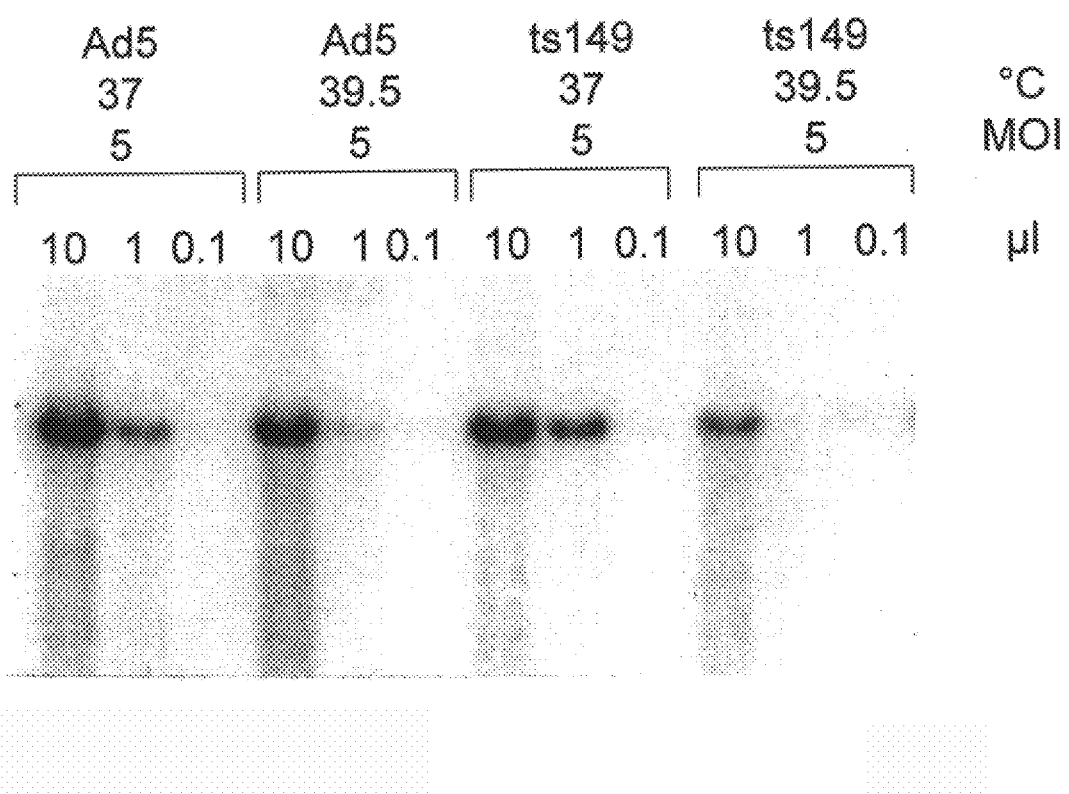
FIG. 1 is a half-tone reproduction of a Southern analysis for rAAV vector production, using a probe for a model CF therapeutic gene contained in the vector. The prominent band at 1.4 kb indicates presence of rAAV in the preparation. Helper function was supplied by adenovirus subtype 5 (Ad5) or by the adenovirus temperature-sensitive strain ts149.

It is an object of this invention to provide methods and materials for generating high titer preparations of adeno-associated virus (AAV) that are substantially free of helper virus, helper virus proteins, and cellular proteins and other components.

Various methods for the generation and processing of AAV particles in mammalian cells are described in detail below, and illustrations of the use of such techniques are provided in the Examples following.

By way of introduction, it is typical to employ a host or "producer" cell for rAAV vector replication and packaging. Such a producer cell (usually a mammalian host cell) generally comprises or is modified to comprise several different types of components for rAAV production. The first component is a recombinant adeno-associated viral (rAAV) vector genome (or "rAAV pro-vector") that can be replicated and packaged into vector particles by the host packaging cell. The rAAV pro-vector will normally comprise a heterologous polynucleotide (or "transgene"), with which it is desired to genetically alter another cell in the context of gene therapy (since the packaging of such a transgene into rAAV vector particles can be effectively used to deliver the transgene to a variety of mammalian cells). The transgene is generally flanked by two AAV inverted terminal repeats (ITRs) which comprise sequences that are recognized during excision, replication and packaging of the AAV vector, as well as during integration of the vector into a host cell genome. A second component is a helper virus that can provide helper functions for AAV replication. Although adenovirus is commonly employed, other helper viruses can also be used as is known in the art. Alternatively, the requisite helper virus functions can be isolated genetically from a helper virus and the encoding genes can be used to provide helper virus functions in trans. The AAV vector elements and the helper virus (or helper virus functions) can be introduced into the host cell either simultaneously or sequentially in any order. The final components for AAV production to be provided in the producer cell are "AAV packaging genes" such as AAV rep and cap genes that provide replication and encapsidation proteins, respectively. Several different versions of AAV packaging genes can be provided (including wild-type rep-cap cassettes as well as modified rep and/or cap cassettes in which the rep and/or cap genes can be left under the control of the native promoters or operably linked to heterologous promoters. Such AAV packaging genes can be introduced either transiently or stably into the host packaging cell, as is known in the art and described in more detail below.

After culturing the host cells under conditions that permit AAV replication and encapsidation, the cells and sub-cellular fractions can be processed to generate high titer preparations of adeno-associated virus (AAV) that are substantially free of helper virus, helper virus proteins, and cellular proteins. Detailed descriptions of processing techniques and illustrative protocols employing such techniques are provided below.

In some embodiments, the methods generally entail culturing (which generally involves maintaining) producer cells under conditions which promote release of rAAV particles from the producer cells. Following these methods of the invention, rAAV particles are released into the cell culture medium ("supernatant") from intact (i.e., not lysed) cells. After culturing the host cells under conditions that permit AAV replication, encapsidation, and release the supernatant can be processed to generate high titer preparations of adeno-associated virus (AAV) that are substantially free of helper virus, helper virus proteins, cellular proteins, and, significantly, cellular DNA. Detailed descriptions of processing techniques and illustrative protocols employing such techniques are provided below.

It is well-established in the AAV field that AAV is not released from the cell unless the cell is lysed, but remains in the nucleus of the cell. Accordingly, the pervasive and universal belief is that, in order to produce rAAV particles, the cells must be lysed. In contrast to the teachings of the field, we have discovered that rAAV particles can be released from cells without lysing the cells, and further that release of rAAV particles can be increased by maintaining the producer cells under various controlled environmental conditions. Using these conditions, rAAV particles can be produced at titers higher than previously obtained. Cells cultured under the conditions described herein produce more virus per cell and release more virus into the culture medium, and, even more significantly, may release a population of AAV with higher infectivity than AAV which is retained within the cell. In other words, the DNAse resistant particle to infectivity ratio can be smaller in the AAV population released into the cell culture medium compared to this ratio of AAV retained within the cell (see, e.g., FIG. 4). Furthermore, since lysis is not an obligatory step in the methods of the present invention, the rAAV particles can be collected from the cell supernatant, thus simplifying subsequent optional purification steps. Alternatively, lysis could also be performed.

In some embodiments, the invention provides methods of release, or preferential release, of infectious viral particles. This preferential release of infectious particles is particularly significant in the viral production context, in which it is highly desirable to produce a population containing a large number of infectious particles as opposed to noninfective particles.

It is understood that the methods and principles described herein are applicable to a number of other viruses which are normally retained (i.e., not released), particularly adenovirus. AAV is exemplified herein.

The rAAV particles produced by the methods of this invention are particularly useful as gene transfer vectors. Methods of using such vectors are known in the art and need not be described herein.

Definitions

A "vector" as used herein refers to a macromolecule or association of macromolecules that comprises or associates with a polynucleotide and which can be used to mediate delivery of the polynucleotide to a cell. Illustrative vectors include, for example, plasmids, viral vectors, liposomes and other gene delivery vehicles.

"AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector").

An "rAAV vector" as used herein refers to an AAV vector comprising a polynucleotide sequence not of AAV origin (i.e., a polynucleotide heterologous to AAV), typically a sequence of interest for the genetic transformation of a cell. In preferred vector constructs of this invention, the heterologous polynucleotide is flanked by at least one, preferably two AAV inverted terminal repeat sequences (ITRs). The term rAAV vector encompasses both rAAV vector particles and rAAV vector plasmids.

An "AAV virus" or "AAV viral particle" or "rAAV vector particle" refers to a viral particle composed of at least one AAV capsid protein (preferably by all of the capsid proteins of a wild-type AAV) and an encapsidated polynucleotide rAAV vector. If the particle comprises a heterologous polynucleotide (i.e. a polynucleotide other than a wild-type AAV genome such as a transgene to be delivered to a mammalian cell), it is typically referred to as an "rAAV vector particle" or simply an "rAAV vector". Thus, production of rAAV particle necessarily includes production of rAAV vector, as such a vector is contained within an rAAV particle.

"Packaging" refers to a series of intracellular events that result in the assembly and encapsidation of an AAV particle.

AAV "rep" and "cap" genes refer to polynucleotide sequences encoding replication and encapsidation proteins of adeno-associated virus. They have been found in all AAV serotypes examined, and are described below and in the art. AAV rep and cap are referred to herein as AAV "packaging genes".

A "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudo-rabies viruses (PRV); which are also available from depositories such as ATCC.

"Helper virus function(s)" refers to function(s) encoded in a helper virus genome which allow AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans.

The term "tsHV" refers to a temperature-sensitive helper virus, which can provide helper functions for AAV replication and packaging but is temperature-sensitive with respect to its own replication (i.e. it can replicate at a "permissive" temperature but replicates at lower efficiency, or preferably not at all, at a "non-permissive" temperature). The ability of the tsHV to provide help for AAV replication may also be temperature sensitive, but preferred tsHV for use with this invention efficiently support AAV replication at temperatures at which AAV can replicate but which are non-permissive for replication of the tsHV. Examples of such tsHV are described below.

An "infectious" virus or viral particle is one that comprises a polynucleotide component which it is capable of delivering into a cell for which the viral species is trophic. The term does not necessarily imply any replication capacity of the virus. Assays for counting infectious viral particles are described elsewhere in this disclosure and in the art. Viral infectivity can be expressed as the P:I ratio, or the ratio of total viral particles to infective viral particles.

A "replication-competent" virus (e.g. a replication-competent AAV) refers to a phenotypically wild-type virus that is infectious, and is also capable of being replicated in an infected cell (i.e. in the presence of a helper virus or helper virus functions). In the case of AAV, replication competence generally requires the presence of functional AAV packaging genes. Preferred rAAV vectors as described herein are replication-incompetent in mammalian cells (especially in human cells) by virtue of the lack of one or more AAV packaging genes. Preferably, such rAAV vectors lack any AAV packaging gene sequences in order to minimize the possibility that replication competent AAV are generated by recombination between AAV packaging genes and an incoming rAAV vector. Preferred rAAV vector preparations as described herein are those which contain few if any replication competent AAV (rcAAV, also referred to as RCA) (preferably less than about 1 rcAAV per $10^2$ rAAV particles, more preferably less than about 1 rcAAV per $10^4$ rAAV particles, still more preferably less than about 1 rcAAV per $10^8$ rAAV particles, even more preferably less than about 1 rcAAV per $10^{12}$ rAAV particles, most preferably no rcAAV).

"Release" of rAAV particles means that rAAV particles enter the cell culture medium from an intact producer cell, i.e., the rAAV particle is released without lysing the cell. It is understood that, in a given producer cell culture, some cells lyse, for example, upon cell death. However, this invention provides methods which promote release of rAAV particle without performing deliberate cell lysis, as it typically done in the art. The terms "release" and "secretion" from a producer cell are used interchangeably herein. As the data disclosed herein indicate, release of rAAV under conditions described herein to promote release is not due to, for example, lytic function of helper virus.

The term "condition that promotes release of rAAV particles" from a producer cell, as used herein, refers to a condition for growing producer cells which lead to increased, or enhanced, rAAV particle release from the producer cell into the culture medium. Conditions which promote release of rAAV from the producer cell into the culture medium are described herein, and are generally, but not necessarily, conditions which enhance cellular metabolism. "Promoting release" of rAAV particles from a producer cell into the culture medium means that the rAAV release from the producer cell is increased when compared to rAAV release from a producer cell not cultured under the environmental condition(s) which enhance release. The increase may be any detectable increase, such as at least about 1%, at least about 5%, at least about 10%, more preferably at least about 20%, more preferably at least about 25%, more preferably at least about 35%, more preferably at least about 50%, more preferably at least about 60%, more preferably at least about 65%, more preferably at least about 75%, more preferably at least about 80%, more preferably at least about 85%, more preferably at least about 90%, more preferably at least about 100% or 2-fold, more preferably at least about 5-fold, more preferably at least about 10-fold, more preferably at least about 20-fold, even more preferably at least about 50-fold. As is well known in the art, when a cell population is grown under a given starting culture condition, the cells' metabolic by-products will change certain of the culture conditions, such as pH and osmolality. Under environmental conditions which promote rAAV particle release, one or more of these parameters is controlled as necessary, i.e, monitored at regular intervals and adjusted to maintain the parameter within a suitable range (i.e., a range that promotes release). Setting and/or control of these conditions will be discussed in more detail below.

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

A "gene" refers to a polynucleotide containing at least one open reading frame that is capable of encoding a particular protein after being transcribed and translated.

"Recombinant", as applied to a polynucleotide means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

An "expression vector" is a vector comprising a region which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

"Heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter.

"Genetic alteration" refers to a process wherein a genetic element is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. Preferably, the genetic element is introduced into a chromosome or minichromosome in the cell; but any alteration that changes the phenotype and/or genotype of the cell and its progeny is included in this term.

A cell is said to be "stably" altered, transduced, or transformed with a genetic sequence if the sequence is available to perform its function during extended culture of the cell in vitro. In preferred examples, such a cell is "inheritably" altered in that a genetic alteration is introduced which is also inheritable by progeny of the altered cell.

The terms "polypeptide", "peptide" and "protein" are used interchangeably herein to refer to polymers of amino acids of any length. The terms also encompass an amino acid polymer that has been modified; for example, disulfide bond formation, glycosylation, lipidation, or conjugation with a labeling component. Polypeptides such as "CFTR", "p53", "E1A" and the like, when discussed in the context of gene therapy and compositions therefor, refer to the respective intact polypeptide, or any fragment or genetically engineered derivative thereof, that retains the desired biochemical function of the intact protein. Similarly, references to CFTR, p53, E1A genes, and other such genes for use in gene therapy (typically referred to as "transgenes" to be delivered to a recipient cell), include polynucleotides encoding the intact polypeptide or any fragment or genetically engineered derivative possessing the desired biochemical function.

An "isolated" plasmid, virus, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more preferred. Thus, for example, a 2-fold enrichment is preferred, 10-fold enrichment is more preferred, 100-fold enrichment is more preferred, 1000-fold enrichment is even more preferred.

A preparation of AAV is said to be "substantially free" of helper virus if the ratio of infectious AAV particles to infectious helper virus particles is at least about $10^2$:1; preferably at least about $10^4$:1, more preferably at least about $10^6$:1; still more preferably at least about $10^8$:1. Preparations are also preferably free of equivalent amounts of helper virus proteins (i.e. proteins as would be present as a result of such a level of helper virus if the helper virus particle impurities noted above were present in disrupted form). Viral and/or cellular protein contamination can generally be observed as the presence of Coomassie staining bands or silver stained bands on SDS gels (e.g. the appearance of bands other than those corresponding to the AAV capsid proteins VP1, VP2 and VP3).

"Efficiency" when used in describing viral production, replication or packaging refers to useful properties of the method; in particular, the growth rate and the number of virus particles produced per cell. "High efficiency" production indicates production of at least 100 viral particles per cell; preferably at least about 10,000 and more preferably at least about 100,000 particles per cell, over the course of the culture period specified. Even more preferably, "high efficiency" production encompasses these production levels of particles per cell as well as the maximum number of cells producing particles, such as at least about 10%, preferably at least about 20%, preferably at least 30%, preferably at least 50%, preferably at least 75%. Example 6 describes culture conditions ("complete" medium) which resulted in 93,000–123,000 rAAV particles per producer cell. In the context of the present invention, efficiency may also be considered in terms of percentage, or extent, of release of viral particles compared to viral particles retained in the cell. Efficiency may also be considered in terms of ratio or relative proportion of total viral particles to infectious viral particles (such as a "P/I" ratio). Assays for determining parameters of efficiency of production, such as replicative units and infectious center assay, are known in the art.

An "individual" or "subject" treated in accordance with this invention refers to vertebrates, particularly members of a mammalian species, and includes but is not limited to domestic animals, sports animals, and primates, including humans.

"Treatment" of an individual or a cell is any type of intervention in an attempt to alter the natural course of the individual or cell at the time the treatment is initiated. For example, treatment of an individual may be undertaken to decrease or limit the pathology caused by any pathological condition, including (but not limited to) an inherited or induced genetic deficiency, infection by a viral, bacterial, or parasitic organism, a neoplastic or aplastic condition, or an immune system dysfunction such as autoimmunity or immunosuppression. Treatment includes (but is not limited to) administration of a composition, such as a pharmaceutical composition, and administration of compatible cells that have been treated with a composition. Treatment may be performed either prophylactically or therapeutically; that is, either prior or subsequent to the initiation of a pathologic event or contact with an etiologic agent.

General techniques

The practice of the present invention will employ, unless otherwise indicated, conventional techniques of molecular biology, virology, animal cell culture and biochemistry which are within the skill of the art. Such techniques are explained fully in the literature. See, for example, "Molecular Cloning: A Laboratory Manual", Second Edition (Sambrook, Fritsch & Maniatis, 1989); "Animal Cell Culture" (R. I. Freshney, ed., 1987); "Gene Transfer Vectors for Mammalian Cells" (J. M. Miller & M. P. Calos, eds., 1987); "Current Protocols in Molecular Biology" (F. M. Ausubel et al., eds., 1987); "Current Protocols in Protein Science" (John E Coligan, et al. eds. Wiley and Sons, 1995); and "Protein Purification: Principles and Practice" (Robert K. Scopes, Springer-Verlag, 1994).

All patents, patent applications, articles and publications mentioned herein, both supra and infra, are hereby incorporated herein by reference.

Selection and Preparation of AAV Vector and AAV Packaging Genes

A recombinant AAV vector of this invention comprises a heterologous (i.e. non-AAV) polynucleotide of interest in place of all or a portion of the AAV rep and/or cap genes that normally make up the bulk of the AAV genome. As in the wild-type AAV genome, however, the rAAV pro-vector is preferably flanked by two AAV inverted terminal repeats (ITRs) as noted above. Variations in which an rAAV construct is flanked by a only a single (typically modified) ITR have also been described in the art and can be employed in connection with the present invention.

Adeno-associated viruses of any serotype are suitable, since the various serotypes are functionally and structurally related, even at the genetic level (see, e.g., Blacklow, pp. 165–174 of "Parvoviruses and Human Disease" J. R. Pattison, ed. (1988); and Rose, Comprehensive Virology 3:1, 1974). All AAV serotypes apparently exhibit similar replication properties mediated by homologous rep genes; and all generally bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to ITRs. The similar infectivity patterns also suggest that the replication functions in each serotype are under similar regulatory control. Among the various AAV serotypes, AAV2 is most commonly employed.

An AAV vector of this invention will typically comprise a polynucleotide that is heterologous to the AAV. The polynucleotide is typically of interest because of a capacity to provide a function to a target cell in the context of gene therapy, such as up- or down-regulation of the expression of a certain phenotype. Such a heterologous polynucleotide or "transgene", will generally be of sufficient length to provide the desired function or encoding sequence. For encapisdation within AAV2 particles, the transgene will preferably be less than about 5kb although other serotypes and/or modifications may be employed to allow larger sequences to packaged into the AAV viral particles.

Where transcription of the heterologous polynucleotide is desired in the intended target cell, it can be operably linked to its own or to a heterologous promoter, depending for example on the desired level and/or specificity of transcription within the target cell, as is known in the art. Various types of promoters and enhancers are suitable for use in this context. Constitutive promoters provide an ongoing level of gene transcription, and are preferred when it is desired that the therapeutic polynucleotide be expressed on an ongoing basis. Inducible promoters generally exhibit low activity in the absence of the inducer, and are up-regulated in the presence of the inducer. They may be preferred when expression is desired only at certain times or at certain locations, or when it is desirable to titrate the level of expression using an inducing agent. Promoters and enhancers may also be tissue-specific: that is, they exhibit their activity only in certain cell types, presumably due to gene regulatory elements found uniquely in those cells.

Illustrative examples of promoters are the SV40 late promoter from simian virus 40, the Baculovirus polyhedron enhancer/promoter element, Herpes Simplex Virus thymidine kinase (HSV tk), the immediate early promoter from cytomegalovirus (CMV) and various retroviral promoters including LTR elements. Inducible promoters include heavy metal ion inducible promoters (such as the mouse mammary tumor virus (mMTV) promoter or various growth hormone promoters), and the promoters from T7 phage which are active in the presence of T7 RNA polymerase. By way of illustration, examples of tissue-specific promoters include various surfactin promoters (for expression in the lung), myosin promoters (for expression in muscle), and albumin promoters (for expression in the liver). A large variety of other promoters are known and generally available in the art, and the sequences for many such promoters are available in sequence databases such as the GenBank database.

Where translation is also desired in the intended target cell, the heterologous polynucleotide will preferably also comprise control elements that facilitate translation (such as a ribosome binding site or "RBS" and a polyadenylation signal). Accordingly, the heterologous polynucleotide will generally comprise at least one coding region operatively linked to a suitable promoter, and may also comprise, for example, an operatively linked enhancer, ribosome binding site and poly-A signal. The heterologous polynucleotide may comprise one encoding region, or more than one encoding regions under the control of the same or different promoters. The entire unit, containing a combination of control elements and encoding region, is often referred to as an expression cassette.

The heterologous polynucleotide is integrated by recombinant techniques into or preferably in place of the AAV genomic coding region (i.e. in place of the AAV rep and cap genes), but is generally flanked on either side by AAV inverted terminal repeat (ITR) regions. This means that an ITR appears both upstream and downstream from the coding sequence, either in direct juxtaposition, preferably (although not necessarily) without any intervening sequence of AAV origin in order to reduce the likelihood of recombination that might regenerate a replication-competent AAV genome. Recent evidence suggests that a single ITR can be sufficient to carry out the functions normally associated with configurations comprising two ITRs (WO 94/13788), and vector constructs with only one ITR can thus be employed in conjunction with the packaging and production methods of the present invention.

The native promoters for rep are self-regulating, and can limit the amount of AAV particles produced. The rep gene can also be operably linked to a heterologous promoter, whether rep is provided as part of the vector construct, or separately. Any heterologous promoter that is not strongly down-regulated by rep gene expression is suitable; but inducible promoters are preferred because constitutive expression of the rep gene can have a negative impact on the host cell. A large variety of inducible promoters are known in the art; including, by way of illustration, heavy metal ion inducible promoters (such as metallothionein promoters); steroid hormone inducible promoters (such as the MMTV promoter or growth hormone promoters); and promoters such as those from T7 phage which are active in the presence of T7 RNA polymerase. An especially preferred sub-class of inducible promoters are those that are induced by the helper virus that is used to complement the replication and packaging of the rAAV vector. A number of helper-virus-inducible promoters have also been described, including the adenovirus early gene promoter which is inducible by adenovirus E1A protein; the adenovirus major late promoter; the herpesvirus promoter which is inducible by herpesvirus proteins such as VP16 or 1CP4; as well as vaccinia or poxvirus inducible promoters.

Methods for identifying and testing helper-virus-inducible promoters have been described in a commonly-owned copending application published as WO96117947 by Targeted Genetics Corporation (Allen et al.). Thus, methods are known in the art to determine whether or not candidate promoters are helper-virus-inducible, and whether or not they will be useful in the generation of high efficiency packaging cells. Briefly, one such method involves replacing the p5 promoter of the AAV rep gene with the putative helper-virus-inducible promoter (either known in the art or identified using well-known techniques such as linkage to promoter-less "reporter" genes). The AAV rep-cap genes (with p5 replaced), preferably linked to a positive selectable marker such as an antibiotic resistance gene, are then stably integrated into a suitable host cell (such as the HeLa or A549 cells exemplified below). Cells that are able to grow relatively well under selection conditions (e.g. in the presence of the antibiotic) are then tested for their ability to express the rep and cap genes upon addition of a helper virus. As an initial test for rep and/or cap expression, cells can be readily screened using immunofluorescence to detect Rep and/or Cap proteins. Confirmation of packaging capabilities and efficiencies can then be determined by functional tests for replication and packaging of incoming rAAV vectors. Using this methodology, a helper-virus-inducible promoter derived from the mouse metallothionein gene has been identified as a suitable replacement for the p5 promoter, and used for producing high titers of rAAV particles (as described in WO 96/17947, Targeted Genetics Corporation).

Given the relative encapsidation size limits of various AAV genomes, insertion of a large heterologous polynucleotide into the genome necessitates removal of a portion of the AAV sequence. Removal of one or more AAV genes is in any case desirable, to reduce the likelihood of generating replication-competent AAV ("RCA"). Accordingly, encoding or promoter sequences for rep, cap, or both, are preferably removed, since the functions provided by these genes can be provided in trans.

The resultant vector is referred to as being "defective" in these functions. In order to replicate and package the vector, the missing functions are complemented with a packaging gene, or a plurality thereof, which together encode the necessary functions for the various missing rep and/or cap gene products. The packaging genes or gene cassettes are preferably not flanked by AAV ITRs and preferably do not share any substantial homology with the rAAV genome. Thus, in order to minimize homologous recombination during replication between the vector sequence and separately provided packaging genes, it is desirable to avoid overlap of the two polynucleotide sequences. The level of homology and corresponding frequency of recombination increase with increasing length of the homologous sequences and with their level of shared identity. The level of homology that will pose a concern in a given system can be determined theoretically and confirmed experimentally, as is known in the art. Typically, however, recombination can be substantially reduced or eliminated if the overlapping sequence is less than about a 25 nucleotide sequence if it is at least 80% identical over its entire length, or less than about a 50 nucleotide sequence if it is at least 70% identical over its entire length. Of course, even lower levels of homology are preferable since they will further reduce the likelihood of recombination. It appears that, even without any overlapping homology, there is some residual frequency of generating RCA. Even further reductions in the frequency of generating RCA (e.g. by nonhomologous recombination) can be obtained by "splitting" the replication and encapsidation functions of AAV, as described by Allen et al. in U.S. patent application 08/769,728, filed Dec. 18, 1996, published internationally as WO98/27204 on Jun. 25, 1998 (Targeted Genetics Corporation)).

The rAAV vector construct, and the complementary packaging gene constructs can be implemented in this invention in a number of different forms. Viral particles, plasmids, and stably transformed host cells can all be used to introduce such constructs into the packaging cell, either transiently or stably.

In certain embodiments of this invention, the AAV vector and complementary packaging gene(s), if any, are provided in the form of bacterial plasmids, AAV particles, or any combination thereof. In other embodiments, either the AAV vector sequence, the packaging gene(s), or both, are provided in the form of genetically altered (preferably inheritably altered) eukaryotic cells. The development of host cells inheritably altered to express the AAV vector sequence, AAV packaging genes, or both, provides an established source of the material that is expressed at a reliable level.

A variety of different genetically altered cells can thus be used in the context of this invention. By way of illustration, a mammalian host cell may be used with at least one intact copy of a stably integrated rAAV vector. An AAV packaging plasmid comprising at least an AAV rep gene operably linked to a promoter can be used to supply replication functions (as described in a co-owned application by Flotte et al., now U.S. Pat. No. 5,658,776). Alternatively, a stable mammalian cell line with an AAV rep gene operably linked to a promoter can be used to supply replication functions (see, e.g., Trempe et al., (U.S. Ser. No. 08/362,608, Jan. 9, 1995, WO95/13392, May 18, 1995); Burstein et al., (U.S. Ser. No. 08/770,122, filed Dec. 18, 1996, WO98/23018, Jun. 25, 1998); and Johnson et al., (U.S. Ser. No. 08/254,358, filed Jun. 6, 1994, issued as U.S. Pat. No. 5,656.785, Aug. 19, 1997)). The AAV cap gene, providing the encapsidation proteins as described above, can be provided together with an AAV rep gene or separately (see, e.g., the above-referenced applications and patents as well as Allen et al., USSN 08/769,728, filed Dec. 18, 1996, WO98/27204 on Jun. 25, 1998 (Targeted Genetics Corporation)). Other combinations are possible and included within the scope of this invention.

Introduction of Genetic Material Into Cells

As is described in the art, and illustrated both herein and in the references cited above, genetic material can be introduced into cells (such as mammalian "producer" cells for the production of AAV) using any of a variety of means to transform or transduce such cells. By way of illustration, such techniques include for example transfection with bacterial plasmids, infection with viral vectors, electroporation, calcium phosphate precipitation, and introduction using any of a variety of lipid-based compositions (a process often referred to as "lipofection"). Methods and compositions for performing these techniques have been described in the art and are widely available.

Selection of suitably altered cells may be conducted by any technique in the art. For example, the polynucleotide sequences used to alter the cell may be introduced simultaneously with or operably linked to one or more detectable or selectable markers as is known in the art. By way of illustration, one can employ a drug resistance gene as a selectable marker. Drug resistant cells can then be picked and grown, and then tested for expression of the desired sequence - i.e., a packaging gene product, or a product of the heterologous polynucleotide, as appropriate. Testing for acquisition, localization and/or maintenance of an introduced polynucleotide can be performed using DNA hybridization-based techniques (such as Southern blotting and other procedures as known in the art). Testing for expression can be readily performed by Northern analysis of RNA extracted from the genetically altered cells, or by indirect immunofluorescence for the corresponding gene product. Testing and confirmation of packaging capabilities and efficiencies can be obtained by introducing to the cell the remaining functional components of AAV and a helper virus, to test for production of AAV particles. Where a cell is inheritably altered with a plurality of polynucleotide constructs, it is generally more convenient (though not essential) to introduce them to the cell separately, and validate each step seriatim. References describing such techniques include those cited herein.

Selection and Preparation of Helper Virus

As discussed above, AAV is a parvovirus that is defective for self-replication, and must generally rely on a helper virus to supply certain replicative functions. A number of such helper viruses have been identified, including adenoviruses, herpes viruses (including but not limited to HSV1, cytomegalovirus and HHV-6), and pox viruses (particularly vaccinia). Any such virus may be used with this invention.

Frequently, the helper virus will be an adenovirus of a type and subgroup that can infect the intended host cell. Human adenovirus of subgroup C, particularly serotypes 1, 2, 4, 6, and 7, are commonly used. Serotype 5 is generally preferred.

The features and growth patterns of adenovirus are known in the art. The reader may refer, for example, to Horowitz, "Adenoviridae and their replication", pp 771–816 in "Fundamental Virology", Fields et al., eds. The packaged adenovirus genome is a linear DNA molecule, linked through adenovirus ITRs at the left- and right-hand termini through a terminal protein complex to form a circle. Control and encoding regions for early, intermediate, and late components overlap within the genome. Early region genes are implicated in replication of the adenovirus genome, and are grouped depending on their location into the E1, E2, E3, and E4 regions.

Although not essential, in principle it is desirable that the helper virus strain be defective for replication in the subject ultimately to receive the genetic therapy. Thus, any residual helper virus present in an rAAV preparation will be replication-incompetent. Adenoviruses from which the E1A or both the E1A and the E3 region have been removed are not infectious for most human cells. They can be replicated in a permissive cell line (e.g. the human 293 cell line) which is capable of complementing the missing activity. Regions of adenovirus that appear to be associated with helper function, as well as regions that do not, have been identified and described in the art (see, e.g., P. Colosi et al., WO97/17458, and references cited therein).

Use of a Conditionally-Sensitive Helper Virus

As described herein, a "conditionally-sensitive" helper virus can also be employed to provide helper virus activity. Such a helper virus strain must minimally have the property of being able to support AAV replication in a host cell under at least one set of conditions where it itself does not undergo efficient genomic replication. Where helper virus activity is supplied as intact virus particles, it is also generally necessary that the virus be capable of replication in a host cell under a second set of conditions. The first set of conditions will differ from the second set of conditions by a readily controllable feature, such as the presence or absence of a required cofactor (such as a cation), the presence or absence of an inhibitory drug, or a shift in an environmental condition such as temperature. Most conveniently, the difference between the two conditions is temperature, and such a conditionally-sensitive virus is thus referred to as a temperature-sensitive helper virus (tsHV).

For the purposes of this disclosure, a "temperature-sensitive" or "ts" helper virus is one which is capable of replicating its genetic material in a eukaryotic cell at a certain temperature range (the "permissive" temperature range), typically about 15–35° C. and preferably about 20–32° C. However, at the "non-permissive" temperature, even when other conditions are kept the same, the rate of replication of genetic material is substantially lower, at least 10-fold lower; usually at least about 100-fold lower; and preferably at least about 1000-fold lower. This temperature is typically about 35–50° C., generally about 42° C. In a typical example of such a ts helper virus, the virus is capable of efficient replication at relatively low temperatures such as temperatures of about 20–32° C., but is incapable of efficient replication at relatively high temperatures such as temperatures of about 37–42° C. It is understood that the virus-infected cell may nonetheless exhibit some metabolic processes attributable to the virus at the non-permissive temperature, including but not limited to helper function for AAV production.

A temperature-sensitive helper virus can be produced in bulk quantities by culturing infected cells at a permissive temperature. AAV vector can then be produced by culturing cells comprising vector elements and the temperature-sensitive helper virus at a non-permissive temperature. The vector preparation will be substantially free of helper virus components.

A large number of temperature-sensitive adenovirus variants have been described in the art; see, e.g., the variants described by Ensinger et al. (J. Virol. 10:328, 1972); Williams et al. (J. Gen Virol. 11:95, 1971); Ishibashi (Proc. Natl. Acad. Sci. USA 65:304, 1970); Lundholm et al. (Virology 45:827, 1971); and Shiroki et al., (Virology 61:474, 1974); amongst others. Complementation analysis indicates that such variants fall into a plurality of different complementation groups (Ginsberg et al., Cold Spring Harbor Symp. Quant. Biol. 34:419, 1974). This suggests that a number of steps in the adenovirus replicative cycle may be rendered temperature-sensitive.

Since helper function for AAV replication requires that only part of the adenovirus cycle be intact, testing for helper function of various mutants at the non-permissive temperature provides a means for mapping the helper function. For example, Ishibashi et al. (Virology 45:317, 1971) reported that temperature-sensitive avian adenovirus variants support replication of AAV1 and AAV2. Ito et al. reported that temperature-sensitive mutant ts13 of human adenovirus 7 (Ad7ts13) helps AAV replication at the non-permissive temperature as efficiently as the wild strain. Drake et al. (Virology 60:230, 1974) reported complementation of AAV4 antigen synthesis by 3 groups of temperature-sensitive mutants of herpes simplex virus type 1 (HSV 1). Handa et al. (J. Gen. Viro. 29:239, 1975) reported helper activity for AAV1 virus production by human adenovirus mutants Ad5ts36, Ad5ts125, Ad5ts149, Ad12tsA275, Ad12tsB221, and Ad12tsC295. Ostrove et al. (Virology 104:502, 1980) reported that temperature sensitive mutants Ad5ts125, Ad5ts135, Ad5ts157, Ad5ts 116, and Ad5ts142, and the host range mutants hr6 but not hr3 support AAV replication. Mayor et al. (J. Gen Virol. 35:545, 1977) reported that Ad31ts13 but not Ad31ts94 supported AAV1 production at the non-permissive temperature.

Straus et al. (Proc. Natl. Acad. Sci. USA 73:742, 1976) reported that Ad5ts125 supported AAV2 replication under conditions where the adenovirus did not itself replicate. They used this property to study DNA intermediates formed during AAV replication. Myers et al. (J. Virol. 35:65, 1980) performed a quantitative study on helper function, and showed that Ad5ts149 supported the production of 20,000 infectious AAV particles per cell at the non-permissive temperature, whereas Ad5ts107 produced only ~100 particles per cell. Since Ad5ts107 has a mutation in the 72 kDa DNA binding protein encoding region, they concluded that this protein played a role in the AAV RNA expression. More recently, Carter et al. (Virology 191:473, 1992) proposed that a fully functional 72 kDa protein is required for quantitative post-transcriptional expression of the AAV rep and cap genes.

As outlined in the background section, the existence of temperature-sensitive adenovirus has been known for quite some time. However, there has been no effective teaching or suggestion regarding the actual use of conditional helper viruses in the generation of recombinant AAV vectors, such as those that might be used for gene therapy.

Part of the explanation may be the difficulty in obtaining workable titers of AAV when using recombinant vectors. Among other things, AAV Rep proteins apparently down-regulate their own expression through the p5 promoter (Tratschin et al., Mol. Cell Biol. 6:2884, 1986). In addition, it has been observed that the expression of the rep gene in packaging cell lines such as those that might be used for the production of recombinant AAV vector, tends to inhibit the growth and/or metabolism of the cell (see, e.g., Targeted Genetics Corporation, WO96/17947, by Allen et al.).

The differences between the generation of wild-type AAV and recombinant AAV vectors tend to be quite dramatic when considered in terms of production. In particular, it has been observed that production of recombinant AAV vectors tends to be substantially lower that production of wild-type AAV particles, and that the presence or generation of even small amounts of contaminating wild-type AAV tends to result in a preferential production of wild-type virus that can eventually outnumber the recombinant AAV vectors.

These phenomena are further illustrated by the results described in Examples 1 and 2 of this disclosure, and in FIG. 1. The adenovirus temperature-sensitive mutant ts149 is reported elsewhere to support AAV particle replication (Myers et al., J. Virol. 35:65, 1980). However, Example 2 shows that when this mutant is used to support the production of an AAV vector with a heterologous promoter under standard conditions, the level of production is several orders of magnitude lower than is supported by wild-type adenovirus.

This disclosure shows that temperature-sensitive helper virus can indeed be used to prepare recombinant AAV vectors at workable titers, overcoming the apparent production obstacles. The descriptions that follow illustrate how to select a temperature-sensitive helper virus and optimize conditions to provide sufficient AAV for the purposes of gene therapy.

In particular, it is shown that extending the replication period for AAV when using tsAd as helper dramatically increases the amount of AAV vector that is produced (Example 3). This is counter-intuitive, because extending the replication period when using wild-type Ad in the same way decreases the amount of AAV vector by at least an order of magnitude. A practitioner of skill in the art seeking to optimize conditions for AAV production would logically go to shorter culture times and higher concentrations of helper virus; both of which are shown herein to be ineffective.

This invention further provides improved culture and separation methods for preparing quantitative amounts of temperature-sensitive adenovirus. While not strictly required for the practice of certain embodiments of this invention, preparations of temperature-sensitive adenovirus obtained by these methods are particularly suited for production of AAV, inter alia, for the purposes of gene therapy.

Condition-sensitive variants of the selected strain of helper virus may be generated by an appropriate mutagenization and selection strategy. For example, virus may be mutagenized with nitrosoguanidine, nitrous acid, hydroxylamine, or 5-bromo-2-deoxyuridine. Candidates are selected that can multiply in a suitable eukaryotic cell under the desired permissive conditions, but not under the desired non-permissive conditions. As an illustration, adenovirus temperature-sensitive mutants can be obtained that multiply, e.g., at 32° C., but not at 39.5° C. Plaquing efficiency ratios at 39.5° C. versus 32° C. are preferably less than $10^{-4}$ and more preferably less than $10^{-5}$. Further illustration of suitable selection processes for temperature-sensitive adenovirus can be found, for example, in Ensinger et al., J. Virol. 10:328, 1972; and Williams et al., J. Gen Virol. 11:95, 1971. Description of adenovirus variants which are not temperature-sensitive, but host-range sensitive, can be found in Harrison et al., Virology 77:319, 1977. Temperature-sensitive mutants effective for use in this invention can be prepared, for example, from alternative helper viruses like herpes simplex 1 (HSV1), or herpes simplex 2 (HSV2). See, e.g., Schaffer et al., Virology 52:57, 1973 for HSV l; Esparza et al., Virology 57:554, 1974 for HSV2. As indicated in the background section, a large number of condition-sensitive helper viruses have been described, and can be obtained from the scientists who developed or described them or from a public depository.

Not all condition-sensitive variants of the aforelisted viruses will work with the present invention. In particular, the strain must be rendered condition-sensitive at a stage in its replicative cycle such that the function that is blocked under non-permissive conditions is not one that is required for high-efficiency replication of AAV. The choice of which helper virus strain to use can be made by reference to both the known biology of the helper virus and the replicative requirements of AAV.

An exemplary helper virus for use with this invention is the temperature-sensitive adenovirus ts149 of the Ad5 serotype (Ad5ts149). As shown in the example section, under optimized conditions, this strain can be used to produce rAAV at levels that match or exceed those supported by wild-type Ad5. The ts149 has a single transition of C–G to A–T at position 7563 (Roovers et al., Virus Genes 4:53, 1990). This results in a change of amino acid leucine at residue 411 of the DNA polymerase to phenylalanine. The DNA polymerase is contained within the E2 transcription unit of adenovirus. However, other ts mutants mapping to this region are less suitable. In particular, the E2 transcription unit also comprises the encoding region for the 72 kDa DNA binding protein (DBP). A strain that produces no detectable DBP (Add/802) supports AAV replication, but at a level that is reduced by an order of magnitude (Carter et al., Virology 191:473, 1992). Adts125, which also comprises a mutation mapping to the DBP encoding region, support AAV replication (Straus et al., J. Virol. 17:140, 1976), although the levels are generally much lower than with wild-type Ad5 (Myers et al., J. Virol. 35:65, 1980). Accordingly, suitable temperature-sensitive adenovirus vectors for use in this invention include those for which the sensitivity maps to the E2A region of the genome, preferably to the DNA polymerase encoding region.

The artisan can readily determine which viral strains are suitable for use as helper virus by conducting an rAAV replication assay using a panel of candidate helper virus strains in a candidate cell under conditions that are non-permissive for self-replication of the helper. For temperature-sensitive variants, screening is done at the non-permissive temperature according to the known properties of the strain. Non-permissive temperatures are generally higher than permissive temperatures, typically about 35–50° C., preferably 38–45° C., more preferably about 39.5° C. Variants supporting AAV replication at a level that is within one order of magnitude of that supported by the corresponding wild-type virus is preferred. In conducting the screening, the artisan should incorporate the other teachings of this disclosure. In particular, screening by culturing for times that give peak AAV replication with wild-type virus is insufficient. A kinetic matrix should be set up in which the candidate helper viruses are used for longer periods, and then compared with the wild-type virus at peak harvest time. A more detailed illustration of this analysis is provided in Example 3 of this disclosure.

Once a suitable helper virus strain has been selected, it may be implemented in this invention in a number of different forms. Viral particles, viral plasmids, and stably transformed host cells can all be used.

In one embodiment, the genome of the helper virus (or minimally, the regions of the helper virus genome encoding helper function) is introduced into the host cell to be used for replication of the rAAV vector in the form of a DNA plasmid, or a plurality of plasmids that provide complementary functions. Procedures for experimental manipulation of adenovirus are known in the art. The reader is referred to Graham et al., "Manipulation of adenovirus vectors". In: Murray E J, ed Methods in molecular biology: Gene transfer and expression protocols, vol7. Clifton, N.J.: The Human Press, 1991:109–128, which provides detailed protocols for propagation, titration, and purification of adenovirus, cotransfection and in vivo recombination. Adenovirus plasmids are available commercially from Microbix Biosystems Inc., Toronto, Canada.

In another embodiment, the host cell is stably transfected with adenovirus genes, or genetically altered to provide the requisite functions for rAAV replication. Alternatively, the host cell may be genetically altered with only a portion of the adenovirus genome, and is subsequently infected or transfected with an adenovirus particle or plasmid. Patent applications WO 95/27071 and WO 95/34671 describe host cells inheritably altered to provide adenovirus function, which complements the replicative property of various defective adenovirus constructs.

In yet another embodiment, the host cell used for AAV replication is infected with a helper virus which is capable of self-replication, but not under non-permissive conditions. Any preparation of the requisite strain providing a sufficient MOI may be used. In keeping with GMP and other regulatory requirements, and to facilitate scale-up for commercial purposes, preparations of helper virus preferably comprise a high density of infectious particles and are substantially free of cellular debris and other contaminants. Desirable properties include the following:

A density of at least $10^6$, preferably at least about $10^8$, more preferably at least about $10^{10}$ IU/ml, as determined in a $TCID_{50}$ assay.

A ratio of adenovirus DNA to total protein or adenovirus hexon that indicates that at least 10%, preferably at least about 50%, more preferably at least about 80% of the viral particles contain adenovirus DNA.

Less than 20%, preferably less than about 10%, more preferably less than about 1% contamination by non-adenovirus material at the protein or DNA level, as detected by SDS gels stained for protein, or agarose gels of restriction nuclease digests stained with ethidium bromide.

A total of at least $10^9$, preferably at least about $10^{11}$, more preferably at least about $10^{13}$ IU per production batch.

Helper virus may be prepared in any cell that is permissive for viral replication. For adenovirus, preferred cells include 293 cells and HeLa cells. Traditionally, when these cells have been used for replication of adenovirus, they have been used in plate cultures. However, as shown in Example 4, these methods generally support replication of temperature-sensitive adenovirus at levels that are one or two logs lower than for wild-type adenovirus.

Accordingly, it is preferable to employ culture techniques-that permit an increase in seeding density. 293 cells and HeLa cell variants are available that have been adapted to suspension culture. HeLa is preferable for reasons of cell growth, viability, and morphology in suspension. As shown in Example 5, these cells can be grown at sufficient density ($2 \times 10^6$ per ml) to make up for the lower replication rate of the temperature-sensitive adenovirus strain. Once established, cells are infected with the virus and cultured at the permissive temperature for a sufficient period; generally 3–7 days and typically about 5 days.

Tangential flow filtration is a technique used in the art for processing large volumes of mammalian cells for the purpose of perfusing, concentrating, and harvesting them. See, e.g., Dorin et al., Biotechnol. Prog. 6:494, 1990; Maiorella et al., Biotechnol. Bioeng. 37:121, 1991.It is recommended that this technique be used with suspension cultures for the preparation of helper virus for use in this invention. Example 5 demonstrates that HeLa S3 cells withstand shear forces of 750–1500 sec$^{-1}$, permitting concentration of the cells and diafiltration of spent media.

Virus is harvested from the culture either from the spent media or by microfluidization of the cells. The level of helper virus produced in the culture is typically at least $10^7$ IU/ml, and preferably at least about $3 \times 10^7$ IU/ml.

Helper virus prepared according to the foregoing description may be used directly for infecting host cells used for rAAV replication. More usually, the virus is isolated and concentrated before use. Current methods for purifying and concentrating helper virus typically involve isopynic CsCl gradients. This method is time and labor intensive, requires numerous open processing steps, and is difficult to scale up. Instead, purification by chromatography is recommended. The reader is referred generally to Prior et al., Pharmaceut. Technol. 19:30, 1995; and Huyghe et al., Human Gene Therapy 6:1403, 1995. Particularly preferred for isolation of temperature-sensitive strains of adenovirus is anion exchange chromatography, especially on a resin of polyethyleneimine using a continuous NaCl gradient at pH 7.4. A detailed illustration of the polyethyleneimine separation method is provided in Example 6.

Providing a Host Cell (Producer Cell) Comprising Helper Virus Function and AAV

In the methods of the invention, producer cells comprising components necessary for viral replication and encapsidation are cultured (in some embodiments, under conditions that promote viral release). Several criteria influence selection of cells for use in producing rAAV particles as described herein. As an initial matter, the cell must be permissive for replication and packaging of the rAAV vector when using the selected helper virus. However, since most mammalian cells can be productively infected by AAV, and many can also be infected by helper viruses such as adenovirus, it is clear that a large variety of mammalian cells and cell lines effectively satisfy these criteria. Among these, the more preferred cells and cell lines are those that can be easily grown in culture so as to facilitate large-scale production of recombinant AAV vector preparations. Again, however, many such cells effectively satisfy this criterion. Where large-scale production is desired, the choice of production method will also influence the selection of the host cell. For example, as described in more detail below and in the art, some production techniques and culture vessels or chambers are designed for growth of adherent or attached cells, whereas others are designed for growth of cells in suspension. In the latter case, the host cell would thus preferably be adapted or adaptable to growth in suspension. However, even in the case of cells and cell lines that are regarded as adherent or anchorage-dependent, it is possible (as described below) to derive suspension-adapted variants of an anchorage-dependent parental line by serially selecting for cells capable of growth in suspension. Developing and obtaining a suspension-adapted cell line which is also capable of producing high yields of virus provides a significant advantage.

Where a temperature-sensitive helper virus is used, the cell must be able to effectively replicate the rAAV vector under conditions that are non-permissive for replication of the helper virus. By way of illustration, when adenovirus ts149 is used as a ts helper virus (as described and illustrated below), the cell must be capable of supporting rAAV replication and packaging at temperatures well above 32° C., preferably about 39.5° C. Human 293 cells are an example of a cell line fulfilling these criteria but numerous other cells and cell lines are capable of replicating rAAV at this relatively elevated temperature.

Ultimately, the helper virus, the rAAV vector sequence, and all AAV sequences needed for replication and packaging must be present in the same cell. Where one or more AAV packaging genes are provided separately from the vector, a host cell is provided that comprises: (i) one or more AAV packaging genes, wherein each said AAV packaging gene encodes an AAV replication or encapsidation protein; (ii) a heterologous polynucleotide introduced into said host cell using an rAAV vector or pro-vector, wherein said rAAV vector or pro-vector comprises said heterologous polynucleotide flanked by at least one AAV ITR and is deficient in said AAV packaging gene(s); and (iii) a helper virus or sequences encoding the requisite helper virus functions. It should be noted, however, that one or more of these elements may be combined on a single replicon. By way of illustration, a helper virus can also comprise an rAAV pro-vector or an AAV packaging gene.

The helper virus is preferably introduced into the cell culture at a level sufficient to infect most of the cells in culture, but can otherwise be kept to a minimum in order to limit the amount of helper virus present in the resulting preparation. A multiplicity of infection or "MOI" of 1–100 may be used, but an MOI of 5–10 is typically adequate.

Similarly, if the AAV vector and/or packaging genes are transiently introduced into the packaging cell (as opposed to being stably introduced), they are preferably introduced at a level sufficient to genetically alter most of the cells in culture. Amounts generally required are of the order of 10 μg per $10^6$ cells, if supplied as a bacterial plasmid; or $10^8$ particles per $10^5$ cells, if supplied as an AAV particle. Determination of an optimal amount is an exercise of routine titration that is within the ordinary skill of the artisan.

These elements can be introduced into the cell, either simultaneously, or sequentially in any order. Where the cell is inheritably altered by any of the elements, the cell can be selected and allowed to proliferate before introducing the next element.

In one preferred embodiment, the helper virus is introduced last into the cell to rescue and package a resident rAAV vector. The cell will generally already be supplemented to the extent necessary with AAV packaging genes. Preferably, either the rAAV vector or the packaging genes, and more preferably both are stably integrated into the cell. It is readily appreciated that other combinations are possible. Such combinations are included within the scope of the invention.

Once the host cell is provided with the requisite elements, the cell is cultured under conditions that are permissive for the replication AAV, to allow replication and packaging of the rAAV vector. Culture time is preferably adjusted to correspond to peak production levels, and is typically 3–6 days. Preferably, at least 100 viral particles are produced per cell; more preferably at least about 1000 per cell, still more preferably at least about 10,000 per cell. Preferably, at least $0.5 \times 10^6$, more preferably at least about $1 \times 10^6$, even more preferably at least about $2 \times 10^6$ RU/ml AAV vectors are produced per $2 \times 10^5$ cells during the culture period. Optionally, large-scale production methods such as suspension culture and tangential flow filtration may be used. AAV particles are then collected, and isolated from the cells used to prepare them.

Preparations of rAAV particles of the present invention preferably comprise a high density of infectious AAV particles and are substantially free of helper virus, helper virus proteins and cellular debris and other contaminants. Desirable properties include the following:

- A concentration of at least $10^7$, preferably at least about $10^8$, more preferably at least about $10^9$ RU/ml, as determined in a replication assay or quantitative hybridization comparison with a known standard.
- No more than $10^3$, preferably no more than about $10^2$, more preferably no more than about $10^1$ infectious particles of helper virus per $10^8$ RU of rAAV particles.
- Less than 5%, preferably less than about 1%, more preferably less than about 0.01%, even more preferably less than about 0.001% contamination by helper virus on a protein basis (wt/wt), detected either by densitometric analysis of SDS gels, or by immunoassay for helper virus specific protein (such as hexon or penton-fiber of adenovirus).
- Less than 5%, preferably less than about 1%, more preferably less than about 0.01%, even more preferably less than about 0.001% contamination by helper virus or cellular protein (wt/wt), detected either by densitometric analysis of SDS gels, or by immunoassay for helper virus or cellular specific proteins.
- Preferably, the preparation is also substantially free of other potential cellular components such as cellular lipids, carbohydrates and/or nucleic acids.

The methods outlined in this disclosure are suitable for preparing small experimental batches, or preparative batches of 10–100 liters or more. For large scale batch preparations, the following property is also desirable:

- A total of at least $10^{10}$, preferably $10^{12}$, and more preferably $10^{14}$ RU of AAV vector particles in the preparation.

Optionally, rAAV vectors may be further processed to enrich for rAAV particles, deplete helper virus particles, or otherwise render them suitable for administration to a subject. Purification techniques may include isopynic gradient centrifugation, and chromatographic techniques. Reduction of infectious helper virus activity may include inactivation by heat treatment or by pH treatment as is known in the art. Other processes may include concentration, filtration, diafiltration, or mixing with a suitable buffer or pharmaceutical excipient. Preparations may be divided into unit dose and multi dose aliquots for distribution, which will retain the essential characteristics of the batch, such as the homogeneity of antigenic and genetic content, and the relative proportion of contaminating helper virus.

Exemplary techniques for generating preparations of helper virus and AAV exhibiting various desirable properties as described above are provided in the following sections and in the subsequent examples.

Various methods for the determination of the infectious titer of a viral preparation are known in the art. However, a preferred method for titer determination is a high-throughput titering assay as provided herein. In an exemplary high-throughput titering assay, an array of culture wells each comprising an aliquot of mammalian cells and an aliquot of virus preparation as well as control wells comprising e.g., cells alone, virus alone and null) is established. The array of culture wells may, for example, be in the form of a microtiter vessel. Typically, aliquots (e.g., serially diluted aliquots) of the virus preparation to be titered are added to the cells, and then the cells and virus are incubated under conditions that allow for infection and replication of the virus (typically growth conditions suitable for the mammalian host cell). Following replication of the virus, viral nucleic acid is generally released by lysis of the mammalian cells (using conditions or agents that promote lysis as necessary). In preferred embodiments, nucleic acid (including viral nucleic acid) in the multiplicity of lysates is transferred and fixed to a membrane under conditions that bind nucleic acid (washing as appropriate to remove proteins and other contaminants). The membrane preferably is a replicate or mirror image of the culture array in which the individual wells of the original array are subsequently represented by "pools" of nucleic acid (from the lysate of each culture well) that are bound at corresponding positions on the membrane. Hybridizing the membrane with a labeled virus-specific (or viral-insert-specific) probe can then be used to identify and quantify the relative amount of viral-specific nucleic acid in each of the points on the array, and by correspondence, in each of the original culture wells. Conditions and materials for nucleic acid transfer, binding, washing and hybridizing can be adapted from routine molecular biological techniques such as "dot blot" hybridization (as described in the art, see, e.g. the molecular biological techniques in Sambrook et al., supra, and Ausubel et al., supra). Illustrative applications of these techniques are presented below.

These methods thus provide a high-throughput infectivity assay which can be used in the determination of the infectious titer of a virus preparation. As shown in Example 4, virus titers determined by this rapid and quantitative method closely correspond to the titers determined by more classical techniques. In addition, however, this high-throughput method allows for the concurrent processing and analysis of many viral replication reactions and thus has many others uses, including for example the screening of cell lines permissive or non-permissive for viral replication and infectivity, as well as the screening of agents that affect viral infection and/or replication, as discussed further below.

Preferred Helper Virus Production and Purification Techniques for use in the Present Invention In various preferred aspects of the present invention, production and purification methods are employed for the generation of helper virus suitable for use in the production of rAAV vectors as described herein. A commonly used helper virus for the production of AAV is adenovirus, typically Ad5, although other helper viruses can also be employed as discussed herein and in the art.

For purposes of illustration, it is convenient to divide the discussion of virus production and purification into "upstream" and "downstream" phases. The "upstream" process generally refers to the production of the virus in suitable host cells and release or removal of the virus from the cells to produce a "crude" virus preparation such as a lysate. "Downstream" processing can be employed to purify the crude virus preparation (e.g. to isolate it away from cellular proteins and/or other contaminants).

A variety of techniques are known for the production and processing of helper viruses, including adenovirus (e.g., CsCl centrifugation, as well as other techniques such as those described in WO 96/27677). Helper virus produced using such techniques can then be employed in the production of rAAV vectors as described herein.

The following sections describe, for purposes of illustration, techniques that can be employed for the production of adenovirus although other techniques are known in the art and can be employed herein.

(i) Helper Virus Upstream

Helper virus, such as Ad5, can be readily produced by infecting mammalian cells (e.g. human cells). In illustrative examples described below, cells are grown in media and culture vessels suitable for growth of the host cell, concentrated prior to infection, and then infected with helper virus (e.g. at an MOI of 1–5) with gentle stirring. Following infection, cells can be resuspended in fresh medium and incubated for an additional period of time (typically about 2 days) in order to allow for replication and packaging of the helper virus. Following incubation, cells can be harvested and lysed to release the helper virus. Following lysis, the cell lysate is preferably treated with a nuclease to degrade free nucleic acid (e.g. cellular nucleic acid) without degrading nucleic acid that is encapsidated in viral particles. The lysate can be clarified (e.g. by filtration and/or centifugation), and can also be subjected to further purification techniques in order to purify and concentrate the helper virus in the preparation, as described and illustrated below. In some embodiments, the lysate is subjected to filtration (such as depth filtration) to clarify the lysate, followed by heat killing, followed by filtration (such as filtration using a 0.5 $\mu$m filter) to further clarify the lysate, followed by cation exchange chromatography (using, for example, an HS resin), followed by nuclease digestion, followed by anion exchange chromatography (using, for example, a PI resin), followed by heparin sulfate chromatography, followed by gel filtration.

As an illustrative example of such a process, cells can be grown in media at a density of about $1 \times 10^6$ cell/ml in a vessel such as a spinner flask. After incubation, cells can then be concentrated to about $10^7$ cells/ml, and infected with Ad5 at 1–2 infectious units/cell with gentle stirring. Cells can then be resuspended in medium at about $10^6$ cells/ml, and allowed to produce virus over an incubation period of about 2 days. Cells can then be harvested, resuspended in medium or buffer (e.g., at about $5 \times 10^6$ cells/ml), and then disrupted, e.g. by mechanical lysis such as by passaging through a microfluidizer at 8000 psi or equivalent technique (e.g. freeze-thaw or sonication). The lysate can be treated with a nuclease (e.g., Benzonase) for one hour at 37° C. The lysate can be clarified through a filter, such as a $1.0 \mu$ filter, or by centrifugation. Analogous techniques and modifications thereof are further described below.

(ii) Helper Virus Downstream

Preferred techniques for the downstream processing of helper virus, such as adenovirus, employ ion-exchange chromatographic procedures for the purification of the helper virus.

By way of illustration, the adenovirus filtrate as described above can be loaded on an anion-exchange resin, such as an N-charged amino or imino resin (e.g. POROS 50 PI, or any DEAE, TMAE, tertiary or quaternary amine, or PEI-based resin) in a chromatography column equilibrated with buffer (such as TMEG, also referred to herein as Chromatography Buffer A: 50 mM Tris (pH 8.0), 5 mM MgCl$_2$, 1 mM EDTA, 5% glycerol).

The column can then be washed with multiple column volumes of TMEG (e.g. 5–6 volumes), followed by multiple volumes of a saline wash (e.g. 5–6 volumes of TMEG with 800 mM NaCl (Chromatography Buffer "B":60% TMEG and 40% TMEG with 2M NaCl). The Adenovirus can be eluted with TMEG with 1300 mM NaCl. (35% Chromatography Buffer A, 65% Chromatography Buffer B).

The peak of adenovirus can be identified in the fractions by an infectivity assay or by a nucleic acid hybridization or immunoassay, as have been described in the art. The peak can be sterile filtered through a $0.2 \mu$ sterile filter. Optionally, the peak can be concentrated by tangential-flow filtration, for example in a Filtron Ultrasette or Millipore Pellicon unit. The peak or concentrate may be diafiltered in this system into a suitable buffer, such as PBS+5% Sucrose. Alternatively, the adenovirus can be left in elution buffer. The final adenovirus product can be sterile filtered through a $0.2 \mu$ filter and stored for use. As described and illustrated herein, a temperature-sensitive helper virus (such as a temperature-sensitive adenovirus) can also be employed.

Examples describing the preparation and use of such helper viruses are provided below for purposes of further illustration.

Preferred AAV Production and Purification Techniques for use in the Present Invention As with helper virus, it is convenient for purposes of illustration to divide the discussion of AAV production and purification into "upstream" and "downstream" process phases; with the "upstream" process generally referring to the production of AAV in suitable host cells and release or removal of the virus from the cells to produce a "crude" AAV preparation. "Downstream" processing can be employed to purify the AAV preparation (e.g. to isolate AAV away from cellular proteins and/or other contaminants).

In preferred aspects of the present invention, upstream and downstream processing of AAV are conducted in a manner designed to substantially reduce and/or eliminate contaminating cellular proteins, as well as any contaminating helper virus (e.g. Ad) or helper virus proteins, any of which might contribute to elicitation of an immune response if present at substantial levels in the final rAAV vector preparation to be used for gene transfer.

The following sections describe, for purposes of illustration, techniques that can be employed for the production of AAV.

(i) AAV Upstream Processing

AAV vector can be produced from a mammalian cell line that contains the necessary AAV packaging genes (e.g. an AAV rep and cap gene); a recombinant AAV (rAAV) provector that comprises a heterologous non-AAV polynucleotide flanked by at least one AAV inverted terminal repeat (ITR); and a helper virus for AAV (e.g. an adenovirus). These components can be introduced into the cell in a variety of configurations, as described above and illustrated below. Since AAV can be replicated and packaged in any of a variety of mammalian cells, there are a large number of cell lines that can be modified and employed for the production of AAV.

By way of illustration, AAV vector can be produced from a cell line, such as "C12" (as described by K. R. Clark et al., Gene Therapy, 3:1124–1132, 1996) or the "C137.5" line (described in a commonly-owned copending application by Targeted Genetics Corporation, J. Allen et al., WO 96/17947), that has been engineered to contain a rep and/or a cap construct, as well as a vector construct. Optionally, a cell line such as C12 or cl37 that contains a rep and/or a cap construct can be transfected with a plasmid that contains a vector construct, such as ptgAAV-CF. Or a cell can be transfected with a plasmid that contains rep and cap, such as pRS5, as well as a plasmid that contains a vector construct. The cell can be infected with Adenovirus, or transfected with DNA that contains adenovirus genes.

A variety of such AAV "producer" cells can be generated, as described in the references cited herein and in the art.

The AAV producer cells can be grown under conditions (including media, temperature and the like) that are generally suitable for growth of the mammalian cells, which are generally also permissive for the replication of AAV. For example, DMEM/F12 suspension medium is preferred for growth of the cells and DMEM medium alone is preferred for AAV vector production. As is known in the art, some cell types and cell lines tend to be attachment-dependent, whereas others are capable of growth in suspension; and many attachment-dependent cells can also be "adapted" to growth in suspension by cycling of the cells under suspension conditions as a means of enriching for and ultimately selecting for variants that are capable of suspension growth. Accordingly, the invention provides methods of generating a population of rAAV particles comprising the step of incubating a producer cell in a cell culture medium, wherein said producer cell is cultured under suspension conditions, whereby rAAV particles are produced. For these embodiments, the producer cell is other than a KB cell. Carter et al. (1979) Virology 92:449–462; Tratschin et al. (1985) Mol. Cell Biol. 5(11):3251–3260. Levels of production using suspension cultures of the invention has been very high (e.g., greater than about $10^2$, $10^3$ or even $10^4$ particles per cell on average in a given cell population). Examples of cells which may be grown in suspension are described herein. In some embodiments, cells produce about $10^2$ to about $10^4$ virus particles per cell; in other embodiments, about $10^2$ to about $10^3$ virus particles per cell; in other embodiments, about $10^3$ to about $10^5$ virus particles per cell; in other embodiments, about $10^4$ to about $10^6$ virus particles per cell. Growth of cells for AAV production can be conducted in any of a variety of vessels, depending in part on whether the selected producer cell line is relatively attachment dependent or is suspension adapted. Such vessels for the growth of attachment-dependent cells include, for example, tissue culture flasks, roller bottles, microcarriers and bioreactors (such as hollow-fiber, packed-bed or fluidized-bed bioreactors). Vessels for suspension-adapted mammalian cell lines include, for example, spinner flasks, tank reactors and air lift fermentors.

AAV replication proceeds for a period of time as well as to a point in the growth cycle where viral production is optimal, preferable mid- to late-logarithmic growth (typically one to three days), after which time the cells can be harvested and lysed to release progeny virus. For example, cells can be resuspended in growth media to about $1$–$10 \times 10^6$ cells/ml, and allowed to produce for 48 hours. Cells can then be harvested (e.g. by centrifugation), and resuspended in buffer (e.g., TMEG (or "Chromatography Buffer A"): 50 mM Tris, pH 8.0, 5 mM $MgCl_2$, 1mM EDTA, 5% Glycerol) at about $1$–$10 \times 10^6$ cells/ml.

AAV can replicate to high copy number (e.g. $10^5$–$10^6$ genomes/cell) in transduced cells if the necessary AAV Rep proteins and helper virus functions are provided relatively simultaneously. If Cap proteins are also provided, AAV particles are assembled in the nucleus of the infected cells where they tend to be assembled in crystalline arrays. The first step in product recovery is therefore generally cellular disruption, except in those embodiments which involve culturing cells under conditions which promote release of virus. It is understood, however, that embodiments which involve release of virus may also include a cell lysis step. Although freeze-thawing and/or sonication can be used to disrupt the cells (as with adenovirus), such techniques are not very suitable to large-scale preparation. Mechanical lysis, using techniques such as microfluidization are thus preferable in those regards. Detergents and other chemical agents can also be employed to mediate or facilitate lysis. Treatment of lysates with nucleases (such as Benzonase) has been found to be helpful for reducing viscosity and improving filterability. Clarification, e.g. by microfiltration to separate vector from at least some portion of the cellular debris, is also helpful for promoting recovery and purification.

By way of illustration, cells can be mechanically lysed after the incubation period by sequential passaging through a microfluidizer (typically at about 8000 psi, using two passages). Other commonly-employed techniques include freeze-thaw cycling and sonication, as is known in the art. The lysate can also be treated with a nuclease to degrade nucleic acid (such as cellular or viral nucleic acid) that is not effectively "protected" by virtue of being packaged into a viral particle. We typically employ Benzonase digestion for about one hour at 37° C. The lysate can also be clarified. Methods for clarification include passage through a filter, such as a 1.0 $\mu$ filter, and centrifugation.

Tangential flow filtration (TFF) can be beneficially employed for processing and harvesting large volumes of cells. TFF can be used to perfuse, concentrate and harvest animal cells. For example, TFF can be used to process cells under laminar flow conditions at average wall shear rates of up to 30000 per second (see, e.g., Maiorella, B., et al., Biotechnology and Bioengineering, 37: 121–126, 1991). Large-scale concentration of viruses using TFF ultrafiltration has been described by R. Paul et al. Human Gene Therapy, 4:609–615, 1993.

If lysis if not required or indicated, cells may be removed from culture medium to provide culture supernatant containing virus particles using methods standard in the art, such as centrifugation and/or filtration.

Illustrative production runs employing such techniques are described below.

(ii) AAV Downstream Processing

As described above, it would be particularly advantageous to obtain preparations of AAV that are substantially free of helper virus particles (such as Ad particles). In addition, AAV vector preparations will preferably also be substantially free of helper virus and cellular proteins (which can also be immunogenic). However, there is a further set of constraints that influence the suitability of techniques for AAV production. Namely, in order to be particularly useful for the production of AAV for gene therapy, it is most desirable for the techniques to be "scalable", i.e. applicable in conjunction with large-scale manufacturing devices and procedures. This latter set of constraints effectively reduces or eliminates the utility of available standard techniques such as cesium chloride separation (which is not well-suited to large-scale preparation procedures).

We have discovered a combination of procedures that are both scalable and remarkably effective for the generation of AAV preparations that are substantially free of helper virus particles, as well as helper virus and cellular proteins and other such contaminants. Our preferred combination of procedures employs ion exchange chromatographic procedures which contrast with various procedures mentioned in the art for the potential purification of, e.g., AAV or Ad. In particular, such procedures as described in the art typically employ a single type of ionic separation, sometimes in combination with other sorts of chromatographic procedures (see, e.g., K. Tamayose et al., Human Gene Therapy 7: 507–513 (1996), and WO96/27677, Sep. 12, 1996). However, in the case of AAV production, we have found that a combination of sequential opposing ion exchange chromatography is particularly effective for the generation of AAV preparations that are substantially free of helper virus particles and proteins, as well as cellular proteins. These opposing ion exchange chromatography steps may be in any order, and may include additional opposing ion exchange chromatography step(s). For example, in some embodiments, a lysate or culture supernatant is subjected to cation exchange chromatography followed by anion exchange chromatography followed by cation exchange chromatography. Preferably, heparin sulfate is used in at least one (preferably the last) cation exchange chromatography.

In view of these discoveries, it appears that AAV is not only "adapted" to both anion exchange and cation exchange chromatography, but that such a combination of both opposing ionic exchanges is particularly effective for eliminating all of the various particle and protein contaminants that typically occur in the generation or AAV vector preparations. Any of a variety of cation and anion exchange resins can be employed in conjunction with these procedures, the fundamental properties of which are the availability of negatively- and positively-charged groups, respectively, to which AAV can bind at least to some degree (most preferably to a degree that differs substantially from the relative binding affinity of one or more of the contaminants referred to above, i.e. Ad particles and proteins, as well as mammalian cellular proteins). Without wishing to be bound by theory, it is believed that the anionic exchange step is particularly effective for separating AAV from Adenovirus; whereas both steps (but especially the cationic exchange step) are believed to be particularly effective for separating AAV from cellular proteins. We have also employed anion exchange followed by tangential flow filtration, as described and illustrated below. As further described below, we have found AAV preparations can be highly concentrated by chromatography on heparin sulfate.

By way of illustration, a clarified AAV lysate as described above can be loaded on an positively charged anion-exchange column, such as an N-charged amino or imino resin (e.g. POROS 50 PI, or any DEAE, TMAE, tertiary or quaternary amine, or PEI-based resin) or a negatively charged cation-exchange column (such as HS, SP, CM or any sulfo-, phospho- or carboxy-based cationic resin). The column can be washed with a buffer (such as chromatography buffer A/TMEG). The column can be eluted with a gradient of increasing NaCl concentration and fractions can be collected and assayed for the presence of AAV and/or contaminants.

Other procedures can be used in place of or, preferably, in addition to the above-described anion and cation exchange procedures, based on inter-molecular associations mediated by features other than charge as is known in the art. Such other procedures include intermolecular associations based on ligand-receptor pairs (such as antibody-antigen or lectin-carbohydrate interactions), as well as separations based on other attributes of the molecules, such as molecular sieving chromatography based on size and/or shape. To take just a single example, the filtrate or partially purified AAV preparation may be loaded on a column that contains an AAV-specific antibody. This column can bind AAV. The column can be rinsed with buffer to remove contaminating proteins, and then eluted with a gradient or step of increasing NaCl concentration and fractions can be collected. Alternatively, such a column can be eluted with a buffer of different pH than that of the loading buffer.

The peaks of AAV and adenovirus can be identified in the fractions by infectivity assays or by a nucleic acid hybridization or immunoassays. The peaks can be pooled, and the pool can be diluted or dialyzed or diafiltered with a buffer (e.g. TMEG or equivalent) to reduce the salt concentration.

This pool can be injected on a positively charged anion-exchange column and/or a negatively charged cation-exchange column (such as those referred to above). The column can be washed with a buffer (such as chromatography buffer A/TMEG). The column can be eluted with a gradient of increasing NaCl concentration and fractions can be collected. The peaks of AAV and adenovirus can be identified in the fractions by an infectivity assay or by a nucleic acid hybridization or immunoassay. The peaks can be pooled based on the results of any of these assays.

The pool of AAV-containing fractions eluted from an anion exchange column as described above can be concentrated and purified by tangential flow filtration (TFF), for example in a Filtron Ultrasette or Millipore Pellicon unit. A membrane of suitable molecular weight cut-off (such as a 100,00 or 300,000 cut-off), is typically composed of a polymer such as regenerated cellulose or polyethersulfone. The preparation is filtered through the membrane, and the product is retained. The retained material can be diafiltered using the membrane with successive washes of a suitable buffer such as Ringer's Balanced Salt Solution +5% glycerol. The final sample is highly enriched for the product and can be sterile filtered through a $0.2\,\mu$ filter and stored for use.

In the purification and concentration of AAV with tangential flow filtration from post-anionic exchange column material, the 300,000 molecular weight cut-off membrane has resulted in higher yields of replicative units than the 100,000 molecular weight cut-off membrane.

An additional step that can be employed for removal of adenovirus, if desired, involves treating the eluant pool with a heat inactivation step (as described herein) and then filtration (e.g. prior to subjecting the preparation to TFF). However, we have found that the "anion exchange-to-TFF" procedure described above resulted in an AAV preparation that was free of detectable adenovirus, and resulted in better yields of purified AAV.

In some embodiments, lysate or culture supernatant is subjected to filtration (such as depth filtration) to clarify the lysate, followed by heat killing, followed by filtration (such as filtration using a $0.5\,\mu$m filter) to further clarify the lysate, followed by cation exchange chromatography (using, for example, an HS resin), followed by nuclease digestion, followed by anion exchange chromatography (using, for example, a PI resin), followed by heparin sulfate chromatography, followed by gel filtration.

Illustrative production runs employing such techniques are described below.

Altering the Growth Conditions of the AAV Producer Cells to Enhance Production

During the course of our production tests with AAV in various media and culture vessels, we typically monitored the cultures with respect various growth and/or metabolic parameters such as cell density, availability of glucose and amino acids, and the production of metabolic by-products such as ammonia and lactic acid. Such components can be readily monitored using standard techniques such as HPLC and enzymatic assays, as described in the art.

As described in the Examples below, we discovered that certain amino acids, particularly aspartate and glutamate, were rapidly depleted in both batch and perfusion cultures. Indeed, in various batch and perfusion experiments, we have observed that from 90 to 99% of the available asp and glu is substantially eliminated after 24 to 48 hours in such cultures. Since the levels of asp and glu appeared to be sub-optimal in such media, we therefore provided additional amounts of either or both amino acid. Culture maintenance and optimization techniques such as these have been routinely applied in the context of large-scale bioproduction (see, e.g., Glacken, M. W., et al., Biotechnology and Bioengineering, 28: 1376–1389,1986; Glacken, M. W., Bio/Technology 6: 1041–1050, 1988; Bibila, T. A., et al., Biotechnol. Prog., 10:87–96, 1994; and Borys, M. C., et al., Biotechnology and Bioengineering, 43: 505–514, 1994).

To our surprise, replacement of these depleted amino acids resulted in a sharp drop in AAV production. For example, in experiments described below, supplementing the standard medium (DMEM) with additional asp and glu drove production efficiency down by more than an order of magnitude (from about 1800 DNase-resistant particles (DRP) per cell to about 140 DRP per cell), although viability was slightly enhanced.

Another common component of media for the growth of mammalian producer cells is a component of serum, such as fetal bovine serum (FBS), which is typically included in media at a level of about 10%. As described below, when the serum level for AAV production was increased (to 20%), AAV vector production dropped by more than 2-fold. In contrast, when the cells were subjected to increasingly lower levels of serum, AAV vector production increased dramatically. For example, when serum levels were reduced to one-tenth of the normal starting levels (i.e. to 1%), vector production increased by more than 4-fold.

Without wishing to be bound by theory, it now appears that stressing the producer cells, either metabolically or by other means as described below, can dramatically enhance the production of AAV vector. In some embodiments, the stress condition enhances production of rAAV vector (as compared to production without imposing a stress condition (s)) at least about 2-fold, at least about 3-fold, at least about 5-fold, at least about 10-fold.

Stress can be effectively characterized, and tested, on the basis of the negative effect of the stress condition or stress agent on cellular growth and/or metabolism. In effect, stress can be achieved by the introduction of any condition or agent that inhibits cellular growth and/or metabolism, or by altering the level of a pre-existing condition or agent such that it becomes sub-optimal with respect to cellular growth and/or metabolism. A large variety of such conditions are known and/or apparent, including nutritional stress (one or more nutrients present at sub-optimal levels for growth and/or metabolism), temperature stress (sub-optimal temperature, which may include growing the cells at lower or higher temperatures, or subjecting the cells to temporary temperature shocks such as cold shock or heat shock), osmotic stress (sub-optimal osmotic level, which may be hypoösmotic or hyperosmotic), pH stress (sub-optimal pH which may be acidic or alkaline), aeration stress (e.g., sub-optimal levels of oxygen or gas exchange), mechanical stress (e.g., shear stress as occurs in culture mixing), radiation stress, and toxic, stress (presence of one or more chemicals or other agents that inhibits growth and/or metabolism). With most if not all of such agents and conditions, it is possible to subject the cells to the stress continuously, or temporarily. By way of illustration, in the case of temperature stress, the cells can be grown at temperatures that are above or below the optimum (typically the optimum is approximately the normal body temperature of the animal from which the cells are derived), or the cells can be subjected to a temporary temperature shock, such as a cold shock or a heat shock. Presently preferred examples of such stress conditions include: nutritional stresses, such as amino acid or serum limitation, the alteration of aeration levels and agitation, the alteration of osmotic levels (e.g. using non-metabolizable carbohydrates such as sorbitol), and inclusion of chemical agents, such as saturated aliphatic carboxylic acids (e.g., propionic, butyric, isobutryic, valeric and caproic acids and their salts with organic or inorganic bases), N,N'-diacylated diamines (such as pentamethylenebisacetamide, hexamethylenebisacetamide and heptamethylenebisacetamide), organic sulfur compounds (such as dimethylsulfoxide), and glucocorticoids (such as hydrocortisone dexamethasone, prednisolone, aldosterone, triamcinolone and cortexolone). Other such agents include genotoxic agents such as chemical carcinogens, UV, heat shock, metabolic inhibitors of DNA synthesis (e.g., hydroxyurea, methotrexate, aphidicolin, drugs that affect topoisomerases (e.g., amsacrine, campthecin, etoposide and novobiocin).

As noted above, the producer cells can also be subjected to sub-lethal stress by altering pH. As exemplified below, we found that pH stress induced by elevating medium pH not only increased AAV, but it also caused a dramatic shift in the relative proportions of AAV that were released into the culture medium. As further described below, this technique can thus be used to facilitate AAV purification as well as enhance production.

Illustrative procedures for optimizing the production of AAV by employing various stress conditions are provided below; as are results demonstrating that the application of a variety of different stress conditions can be used to effectively enhance AAV production levels.

Conditions which promote release of rAAV particles from producer cells

As described above with respect to pH, the present invention provides methods for generating a population of recombinant adeno-associated virus (rAAV) particles, comprising the step of: a) incubating a population of producer cells in a cell culture medium under conditions that promote release of rAAV particles from the producer cells into the culture medium. The released rAAV particles may then be harvested from the cell culture medium, thereby obtaining a population of viral particles.

Conditions which promote (or enhance) release of AAV (including rAAV) particles from a producer cell into the culture medium include, but are not limited to pH of the culture medium; osmolality of the culture medium; temperature; concentration of a given ion in the culture medium (which can affect conductivity); cell density; dissolved oxygen concentration in the culture medium; glucose concentration in the culture medium; concentration of amino acids in the culture medium; and conditions which promote cell cycle synchronization. Any one or more of these parameters is maintained within a suitable range (i.e., a range which promotes release) during which the cells release AAV particles. Although one parameter (i.e., condition) may be sufficient to promote release, a combination of two or more parameters can be simultaneously maintained, each within its own suitable range. Further, a suitable range for one parameter may vary depending on whether any additional parameter(s) used. If one parameter is held within a suitable range for a period of time, a second parameter can be maintained within a second suitable range for the same or a different period of time as the first parameter. Alternatively, conditions may be employed serially. For example, control of pH may occur during one phase of growth, followed by control of temperature.

It is well within the ability of one skilled in the art to vary these parameters and to determine whether release of rAAV into the culture medium is enhanced, relative to the amount of rAAV released when producer cells are not maintained under the given environmental condition(s). Enhanced (or increased) release of rAAV particles from a producer cell can be measured by any of a number of methods known in the art, including, but not limited to, functional assays such as a replication center assay and an infectious center assay; immunological assays for cap gene products, such as ELISA; HPLC; and any of a number of DNA detection methods (to detect the presence of viral DNA), such as slot blot.

Generally, any of these conditions may be monitored and controlled to the extent necessary and/or desired using standard methods and equipment known in the art. The condition is measured and adjustments are made to maintain or return the condition to its suitable level (i.e., a level which promotes virus release). We have observed that failure to appropriately or adequately maintain culture conditions may result in cessation of virus particle release, while other conditions, such as osmolality, need not be maintained at a specific level, but setting of initial culture condition with respect to this parameter(s) is sufficient. For conditions that need to be monitored and adjusted, for example, a bioreactor and/or media perfusion system may be used. These systems are preferred, because they allow more careful control of culture conditions. However, any system which allows sufficient control and adjustment of culture conditions to allow sufficient and/or desired release of AAV particles is suitable. Other examples of control mechanisms for providing the conditions are provided herein.

In one embodiment, producer cells are grown under pH conditions that promote viral particle release. Generally, pH of the culture medium is maintained within a range of about 7.0 to about 8.5, preferably about 7.4 to about 8.5, more preferably about 7.5 to about 8.0. Even more preferably, and especially if pH is the only condition used to promote release, the pH is about 8.0. A bioreactor, for example, permits control of pH to +/−0.05, and even more precise control is available (such as to +/−0.01), and can monitor pH every one to 3 minutes or even less. In some embodiments, cells are grown under pH conditions whereby at least about 67% of total virus particles are found in culture supernatant. In other embodiments, cells are grown under pH conditions such that at least about 80%, at least about 82%, at least about 90%, at least about 92%, at least about 95%, of virus particles are found in culture supernatant. Preferably, the P/I, or particle to infectivity ratio, in culture supernatant is less than about 4,000, more preferably less than about 3,000, more preferably less than about 2,000, more preferably less than about 1,700, more preferably less than about 1,500. In some embodiments, cells are cultured at about pH 8 and are harvested on about 96 hours from infection with helper virus (or introduction or initiation of helper virus function(s)). In other embodiments, cells are cultured at about pH 8 and are harvested on about 72 hours from infection with helper virus (or introduction or initiation of helper virus function(s)). In other embodiments, cells are cultured at about pH 8 and are harvested on about 48 hours from infection with helper virus (or introduction or initiation of helper virus function(s)).

In some embodiments a condition or conditions other than pH is used to promote virus release. For example, in other embodiments, temperature is used to promote virus release. Generally, the temperature of the culture medium is maintained between about 30° C. to about 45° C., preferably between about 32° C. to about 42° C., more preferably about 35° C. to about 40° C. Even more preferably, and especially if temperature is the only condition to promote release, the temperature is about 37° to about 39° C. A bioreactor for example can control a temperature to +/−0.5° C, and can monitor as closely as about every 30 seconds.

In other embodiments, osmolality is used to promote virus release. Generally, the osmolarity of the culture medium is initiated and/or maintained between about 11 mOsM to about 650 mOsM, preferably about 150 mOsM to about 500 mOsM, preferably about 200 mOsM to about 400 mOsM, even more preferably about 300 mOsM (especially if osmolarity is the only condition used to promote release). Osmolality, a term well understood in the art, is defined as number of solute molecules per kg water. Generally, compounds such as NaCl and other salts, mannitol, glucose, contribute to osmolality. Osmolality can be measured using standard techniques in the art, such as freezing point depression using, for example, an osmometer. As is understood in the art, use of an ionic solute (such as Na or K) to adjust osmolality also can also affect other parameters, such as conductivity. Accordingly, another condition which may be used to promote viral release is conductivity. Generally, the conductivity of the culture medium is initiated and/or maintained at least about 5 mS, preferably at least about 10 mS, preferably at least about 15 mS (milliSiemens). In some embodiments, the lower limit of conductivity is about any of the following: 5, 7, 10, 12, 15, 20 mS; and the upper limit (selected independently of the lower limit) is about any of the following: 7, 10, 12, 15, 20, 22, 25, 30 mS. Thus, for example, the conductivity (in mS) may range from about 5 to about 7, about 5 to about 10, about 7 to about 10, about 10 to about 20, about 10 to about 25. Preferably, the ion used to adjust conductivity is sodium (Na+). Conductivity can be measured using standard methods and devices in the art.

Other conditions that may be used in the methods of the present invention include, but are not limited to, any one or more of the following: growth factors, such as insulin, EGF and FGF; glucose concentration; dissolved oxygen concentration; enriched media (e.g., additional glucose and/or other nutrients such as vitamins and amino acids). Glucose concentrations are generally between about 0.1 to about 20 g/l; more preferably between about 0.5 to about 15 g/l; more preferably between about 1 to about 10 g/l. Oxygen concentrations (typically measured by, for example, dissolved oxygen electrode or blood gas analyzer) are generally between about 10% to about 200% relative to air, preferably between about 20% to about 100% relative to air, preferably about 30% to about 75% relative to air. Generally, the higher the cell density, the more enriched the media. Media conditions may be maintained and/or supplemented using techniques known in the art, such as perfusion.

Producer cells are grown for a suitable period of time in order to promote release of virus into the media. Generally, cells may be grown for about 24 hours, about 36 hours, about 48 hours, about 72 hours, about 4 days, about 5 days, about 6 days, about 7 days, about 8 days, about 9 days, up to about 10 days. After about 10 days (or sooner, depending on the culture conditions and the particular producer cell used), the level of production generally decreases significantly. Generally, time of culture is measured from the point of viral production. For example, in the case of AAV, viral production generally begins upon supplying helper virus function in an appropriate producer cell as described herein. Generally, cells are harvested about 48 to about 100, preferably about 48 to about 96, , preferably about 72 to about 96, preferably about 68 to about 72 hours after helper virus infection (or after viral production begins). In the Examples, results are usually expressed number of days, e.g., "day 2", "day 3", etc. These designations generally indicate an additional day as measured from infection with helper virus. That is, a result reported for "day 3" generally indicates that the result was obtained approximately 2 days, or 48 hours, from time of introduction of helper virus function(s).

As discussed above, any one or more, in any combination, of the conditions that promote release may be used. For example, cells may be grown under any one or more of the following conditions: (a) pH at about 8.0; (b) temperature of about 39° C.; (c) about 300 mOsM; (d) enriched media, for about 2 to 3 days. "Enriched media" generally mean enriched in terms of additional inorganic salts (such as $Mg^2, Ca^{+2}$), vitamins, and/or co-factors such that serum may be reduced or even eliminated. In a preferred embodiment, cells are grown under the following conditions: (a) about 300 mOsm; (b) about pH 8.00; (c) about 39° C.; (d) and are harvested on about 96 hours from infection with helper virus. In a preferred embodiment, cells are grown under the following conditions: (a) about pH 8.00; (b) about 39° C.; and (c) and are harvested on about 96 hours from infection with helper virus. In another embodiment, cells are grown under the following conditions: (a) about 300 mOsm; (b) about pH 8.00; (c) about 39° C.; (d) and are harvested on about 72 hours from infection with helper virus. In another embodiment, cells are grown under the following conditions: (a) about pH 8.00; (b) about 39° C.; and (c) and are harvested on about 72 hours from infection with helper virus. In another embodiment, cells are grown under the following conditions: (a) about 300 mOsm; (b) about pH 8.00; (c) about 39° C.; (d) and are harvested on about 48 hours from infection with helper virus. In another embodiment, cells are grown under the following conditions: (a) about pH 8.00; (b) about 39° C. ; and (c) and are harvested on about 48 hours from infection with helper virus. In another embodiment, cells are grown under the following conditions: (a) about pH 8.00; (b) conductivity of at least about 10 mS, or in alternative embodiments, conductivity of about 15 mS, preferably about 17 mS. In another embodiment, cells are grown under the following conditions: (a) about pH 7.2 to about 7.4; (b) conductivity of at least about 10 mS, or alternative embodiments, conductivity of about 15 mS, preferably about 17 mS.

In some embodiments, pH is maintained at about 8.0, and the culture is grown at a temperature of about 39° C. In some embodiments, pH is maintained at about 8.0 and the osmolality (at least the initial osmolality) is about 300 mOsm. In some embodiments, pH is maintained at about 8.0, the osmolality (at least the initial osmolality) is about 300 mOsm, and the culture is grown at a temperature of about 39° C. In some embodiments, an ionic salt such as a sodium salt is used to adjust and/or maintain osmolality and/or pH.

In some embodiments, cells are synchronized. This may be accomplished, for example, by subjecting the cells to stress conditions, particularly before addition of helper virus functional(s). Synchronization may contribute to overall productivity. Possible forms of stress include, but are not limited to, a nutritional stress, an osmotic stress, a pH stress, a temperature stress, an aerobic stress, a mechanical stress, a radiational stress and a toxic stress. A non-limiting example by which nutritional stress is imposed is by culturing the producer cells in a medium that is deficient in one or more amino acids.

It is also understood that, the invention also includes methods of treating producer cells (i.e., intact producer cells) with an agent or condition that promotes virus release, for example, treatment with an agent which permeabilizes a cell, such as an ionophore or a toxin (such as a bacterial toxin), and/or osmotic shock. Agents and conditions which permeabilize cells are known in the art. Examples include, but are not limited to, detergents such as saponin, igitonin, Triton X-100, sodium dodecyl sulfate (SDS), C12E8, sodium dodecyl sulfate, sodium cholate and sodium deoxycholate; small inorganic and organic molecules such as glycyl-L-phenylalanine-beta-naphthylamide, Cu2+ ions or methylamin, nystatin, harzianins HC; peptides and proteins such as magainin, rotavirus capsid protein VP5*, amphotericin B, streptolysin O, defensin A, cryptdins 2 and 3, and C5b-9; physical conditions such as electroporation and cell scraping; phospholipids such as lysolecithin (lysophosphatidylcholine). For these embodiments, the producer cells of a culture population generally retain their integrity, i.e., are not lysed (although, as in any cell culture population, some cells may be lysed). Generally, less than about any of the following percentage of cells are lysed: 50%, 45%, 40%, 35%, 30%, 25%, 20%, 15%, 12%, 10%, 8%, 5%, 3%, 2%, 1%. Alternatively, generally about at least any of the following percentage of cellular contents are retained in cells (i.e., retained in the cell membrane): 40%, 45%, 50%, 55%, 60%, 65%, 70%, 75%, 80%, 85%, 90%, 95%, 98%.

Examples of suitable culture media are described in the Examples.

Harvesting and Purifying Released Viral Particles

Producer cells may be cultured in suspension or attached to a suitable surface. Methods of suspension or fixed cultures are known in the art. Upon generation of a population of released viral particles, the released viral particles may be harvested and/or purified for further use. As discussed in more detail herein, virus particles in culture media are separated from producer cells using methods known in the art, such as centrifugation or filtration (such as tangential flow filtration in a hollow-fiber membrane). Preferably, one or more additional purification steps are performed after separating producer cells from the culture medium. Examples of such steps include, but are not limited to, concentration using suitable filters or ion exchange chromatography. Various production and purification methods are described in WO 99/11764 (PCT/US98/18600) (Targeted Genetics Corporation). Any purification step(s) described herein may be applied to culture supernatant, as well as those known in the art (in any combination).

In some embodiments, culture supernatant (after cells are removed) is subjected to opposing ionic chromatography, as described above. In some embodiments anion-exchange chromatography is followed by cation-exchange chromatography. In other embodiments, cation-exchange is followed by anion-exchange chromatography. In some embodiments, culture supernatant is subjected to chromatography on heparin sulphate, preferably after treatment of opposing ionic chromatography, more preferably after treatment of culture supernatant on cation exchange chromatography followed by anion exchange chromatography. In some embodiments, the supernatant is subjected to cation exchange chromatography followed by anion exchange chromatography followed by cation exchange chromatography. Preferably, heparin sulfate is used in at least one (preferably the last) cation exchange chromatography. These techniques are described in more detailed below.

By way of illustration, culture supernatant, or a preparation which has been eluted from an anion-exchange or cation-exchange column and/or concentrated by tangential flow filtration can be purified by binding to a column comprising heparin sulphate which serves as a cationic exchange resin. The AAV can then be eluted from such a column using a buffer containing a salt (eg, a linear gradient of NaCl). For example, AAV obtained from pooled fractions from anion-exchange chromatography column can be concentrated and diafiltered into TMEG plus 100 mM NaCl using a 300K tangential flow filtration membrane. This concentrate may be injected on a one ml heparin sulphate column (Pharmacia "Hi-Trap Heparin" column), and eluted using a linear gradient of NaCl.

Use of rAAV for gene therapy

Embodied in this invention are vector compositions comprising polynucleotides with a therapeutically relevant genetic sequence. AAV viral vectors of this invention can be used for administration to an individual for purposes of gene therapy. Suitable diseases for gene therapy include but are not limited to those induced by viral, bacterial, or parasitic infections, various malignancies and hyperproliferative conditions, autoimmune conditions, and congenital deficiencies.

Gene therapy can be conducted to enhance the level of expression of a particular protein either within or secreted by the cell. Vectors of this invention may be used to genetically alter cells either for gene marking, replacement of a missing or defective gene, or insertion of a therapeutic gene. Alternatively, a polynucleotide may be provided to the cell that decreases the level of expression. This may be used for the suppression of an undesirable phenotype, such as the product of a gene amplified or overexpressed during the course of a malignancy, or a gene introduced or overexpressed during the course of a microbial infection. Expression levels may be decreased by supplying a therapeutic polynucleotide comprising a sequence capable, for example, of forming a stable hybrid with either the target gene or RNA transcript (antisense therapy), capable of acting as a ribozyme to cleave the relevant mRNA, or capable of acting as a decoy for a product of the target gene.

Of particular interest is the correction of the genetic defect of cystic fibrosis, by supplying a properly functioning cystic fibrosis transmembrane conductance regulator (CFTR) to the airway epithelium. Afione et al. (J. Virol. 70:3235, 1996) and Conrad et. al. (Gene Therapy: in press, 1996) have shown stable in vivo CFTR gene transfer to the primate lung using single-dose AAV vectors. There are a variety of CFTR polypeptides that are capable of reconstructing CFTR functional deficiencies in cells derived from cystic fibrosis patients. Rich et al., Science, 253: 205 (1991) described a CFTR derivative missing amino acid residues 708–835, that was capable of transporting chloride and capable of correcting a naturally occurring CFTR defect. Egan et al., Nature, 358:581 (1992) described another CFTR derivative (comprising about 25 amino acids from an unrelated protein followed by the sequence of native CFTR beginning at residue 119) that was also capable of restoring electrophysiological characteristics of normal CFTR. Arispe et al., Proc. Natl. Acad. Sci. USA 89: 1539 (1992) showed that a CFTR fragment comprising residues 433–586 was sufficient to reconstitute a correct chloride channel in lipid bilayers. Sheppard et al., Cell 76: 1091 (1994) showed that a CFTR polypeptide truncated at residue 836 to about half its length was still capable of building a regulated chloride channel. Thus, AAV vectors with encoding sequences for native CFTR protein, and mutants and fragments thereof, are all preferred embodiments of this invention.

Also of particular interest is the correction of the p53 tumor suppressor gene, locally defective in certain tumor types, by supplying a properly functioning p53 gene to the tumor site (Huyghe et al., Human Gene Therapy 6:1403, 1995).

Compositions of this invention may be used in vivo as well as ex vivo. In vivo gene therapy comprises administering the vectors of this invention directly to a subject. Pharmaceutical compositions can be supplied as liquid solutions or suspensions, as emulsions, or as solid forms suitable for dissolution or suspension in liquid prior to use. For administration into the respiratory tract, a preferred mode of administration is by aerosol, using a composition that provides either a solid or liquid aerosol when used with an appropriate aerosolizer device. Another preferred mode of administration into the respiratory tract is using a flexible fiberoptic bronchoscope to instill the vectors. Typically, the viral vectors are in a pharmaceutically suitable pyrogen-free buffer such as Ringer's balanced salt solution (pH 7.4). Although not required, pharmaceutical compositions may optionally be supplied in unit dosage form suitable for administration of a precise amount.

An effective amount of virus is administered, depending on the objectives of treatment. An effective amount may be given in single or divided doses. Where a low percentage of transduction can cure a genetic deficiency, then the objective of treatment is generally to meet or exceed this level of transduction. In some instances, this level of transduction can be achieved by transduction of only about 1 to 5% of the target cells, but is more typically 20% of the cells of the desired tissue type, usually at least about 50%, preferably at least about 80%, more preferably at least about 95%, and even more preferably at least about 99% of the cells of the desired tissue type. As a guide, the number of vector particles present in a single dose given by bronchoscopy will generally be at least about $1 \times 10^8$, and is more typically $5 \times 10^8$, $1 \times 10^{10}$, and on some occasions $1 \times 10^{11}$ particles, including both DNAse resistant and DNAse susceptible particles. In terms of DNAse resistant particles, the dose will generally be between $1 \times 10^6$ and $1 \times 10^{14}$ particles, more generally between about $1 \times 10^8$ and $1 \times 10^{12}$ particles. The treatment can be repeated as often as every two or three weeks, as required, although treatment once in 180 days may be sufficient.

The effectiveness of the genetic alteration can be monitored by several criteria. Samples removed by biopsy or surgical excision may be analyzed by in situ hybridization, PCR amplification using vector-specific probes, RNAse protection, immunohistology, or immunofluorescent cell counting. When the vector is administered by bronchoscopy, lung function tests may be performed, and bronchial lavage may be assessed for the presence of inflammatory cytokines. The treated subject may also be monitored for clinical features, and to determine whether the cells express the function intended to be conveyed by the therapeutic polynucleotide.

The decision of whether to use in vivo or ex vivo therapy, and the selection of a particular composition, dose, and route of administration will depend on a number of different factors, including but not limited to features of the condition and the subject being treated. The assessment of such features and the design of an appropriate therapeutic regimen is ultimately the responsibility of the prescribing physician.

The foregoing description provides, inter alia, methods for generating high titer preparations of recombinant AAV vectors that are substantially free of helper virus (e.g. adenovirus) and cellular proteins. It is understood that variations may be applied to these methods by those of skill in this art without departing from the spirit of this invention.

The examples presented below are provided as a further guide to a practitioner of ordinary skill in the art, and are not meant to be limiting in any way.

EXAMPLES

Example 1

Illustrative Production of Recombinant AAV Vector Using a Wild-Type Helper Virus (AD5) and a Temperature-Sensitive Helper Virus (AD TS149)

This example illustrates the use of a wild-type helper virus (Ad5) and a temperature-sensitive helper virus (Ad ts149) to provide helper functions for the replication of a recombinant AAV vector particle comprising a model therapeutic gene.

The ptgAAVCF plasmid consists of the left hand AAV2 ITR; a full length cystic fibrosis transmembrane regulator cDNA; a synthetic polyadenylation sequence based on the mouse β-globin polyadenylation sequence; AAV2 sequences downstream of the cap coding sequences; and the right-hand AAV2 ITR in a pBR322 plasmid backbone (Afione et al., 1996). The pGEM-RS5 packaging plasmid was derived from the pHIVrep plasmid (Antoni et al., 1991) and consists of the U3 and R regions from the HIV-1 LTR; the rep and cap regions from AAV2 including the p19 and p40 promoters; pBR322 and pGEM plasmid sequences for bacterial replication and selection; and a small region of human Alu repetititve cellular DNA upstream of the HIV LTR.

Adenovirus type 5 was grown from a stock obtained from the American Type Culture Collection (Rockville, Md.). Ad5ts149 (Ensinger et al., J. Virol. 10:328, 1972) was obtained from Harold S. Ginsberg.

Working stocks of Ad5 and Ad5ts149 (ts149) were produced at 37° C. and 32° C.; respectively, by infecting 293–1 cells at a multiplicity of infection (MOI) of 5 and 1; respectively. After 4 hours the cultures were refed with fresh medium and incubated at 37° C. in a humidified 10% $CO_2$ incubator. After seventy-two hours, cells were removed, pelleted at 1000 g at 15° C. and resuspended in PBS containing 0.1 g/L of $MgCl_2$ and 0.1 g/L $CaCl_2$. The cell suspension was then frozen and thawed three times, sheared three times through an 18 gauge needle and clarified by centrifugation at 1000 g at 15° C. The clarified lysate was then treated with DNase I at a final concentration of 2 mg/ml for 30 minutes at 37° C. The treated lysate was layered on a discontinuous step gradient of CsCl in water comprising 4.0 ml of CsCl (1.25 $g/cm^3$) layered over 2.0 ml of CsCl (1.40 $g/cm^3$) in water and centrifuged at 35,000 RPM for 1 to 2 hours in a Beckman SW41 rotor. The adenovirus band from each tube was removed, pooled and diluted in 1.35 $g/cm^3$ CsCl in water and centrifuged overnight at 35,000 RPM in a Beckman SW55 rotor. The adenovirus band was pooled, adjusted to 10% glycerol and dialyzed extensively against 10 mM Tris pH 7.5 buffer supplemented with 1.0 mM $MgCl_2$ and 10% glycerol.

293–1 cells (ATCC CRL 1573) were maintained in T-flasks in a humidified 10% $CO_2$ incubator in DMEM high glucose medium (JRH) supplemented with 10% fetal bovine serum (FBS, Hyclone). For this example, the 293–1 cells were inoculated at $4.4 \times 10^4$ cells/cm² in tissue culture flasks with DMEM supplemented with 10% FBS and 2.0 mM L-glutamine, and incubated for twenty-four hours at 37° C. in a humidified 10 % $C_2$ incubator.

The cells (about $10^7$ cells per flask) were then infected with working stocks of either Ad5 or ts149 for 1 hour at a MOI of 5, followed by transient transfection of vector and packaging plasmids. Transient co-transfection of ptgAAVCF vector plasmid and pGEM-RS5 helper plasmid was performed using LIPOFECTAMINE™ (Gibco). In that process, 37.5 μg of each plasmid along with 150 μl LIPOFECTAMINE™ were mixed and diluted in 4.75 ml of serum-free MEM. The adenovirus inoculum was removed and the plasmid-LIPOFECTAMINE™ mixture was added to the cells and incubated for four hours in a 5% $CO_2$ incubator at the appropriate temperature. The plasmid-LIPOFECTAMINE™ mixture was removed from the culture after four hours and replaced with fresh medium.

Cells infected with wild-type virus were cultured at 37° C. and cells infected with Adts149 were incubated at 39.5° C. After 72 hours, the cells were harvested, pelleted and resuspended in 10 mM Tris pH 7.5. The suspension was then lysed by sonication in a ice-water bath using a Branson cup-horn sonicator utilizing four 15 second pulses and assayed for rAAVCF and adenovirus production.

Example 2

Quantitation of RAAV and Adenovirus Titers in Vector Preparations

Cell lysates from the preceding example were assayed for production of rAAVCF vector by C37 replication assay and analyzed for adenovirus production by slot-blot hybridization.

HeLa C37 was constructed to allow inducible expression of AAV Rep proteins for rAAV vector replication. Briefly, an AAV Rep/Cap expression cassette consisting of the mouse metallothionein I promoter, AAV2 rep and cap genes and AAV transcription termination site was constructed. Also included in the plasmid was a neomycin resistance gene under the control of the SV40 early promoter, SV40 small T intron and the SV40 polyadenylation signal. HeLa cells were transfected with the plasmid and clones were selected in G418. A panel of clones was screened by a rAAV vector amplification assay. One clone, C37, demonstrated consistent and dose dependent amplification of rAAV vector following transduction and adenovirus infection.

Detection of replicating vector is accomplished by DNA isolation followed by hybridization to a CFTR probe. In detail, HeLa C37 cells were inoculated at $4.4 \times 10^4$ cells/cm² in tissue culture flasks with DMEM supplemented with 10% FBS and 2.0 mM L-glutamine and incubated for twenty-four hours at 37° C. in a humidified incubator at 5% $CO_2$. The cells were then inoculated with adenovirus (MOI=5) and dilutions of rAAVCF sample for 72 hours. Cells were harvested by scraping and prepared for Southern blot analysis. Total cellular DNA was prepared, digested with EcoRI, electrophoresed on a 1% agarose gel, transferred to a nylon 66 membrane followed by hybridization with a $^{32}$P-labeled human CFTR cDNA restriction fragment. This probe detects an approximately 1.5 kb fragment from the AAVCF vector (corresponding to the predicted 1.488 kb EcoRI fragment). Vector replication was quantitated relative to an endogenous genomic CFTR band and is expressed as replication units. One replication unit (RU) is defined as a signal intensity equivalent to that of the endogenous genomic CFTR band which is approximately 1.8 kb. In some experiments, linear regression of serially diluted known vector standards was used to extrapolate and calculate vector concentration in samples.

The adenovirus DNA slot blot assay was conducted as follows. Aliquots of samples were denatured in 0.4M NaOH, 10 mM EDTA with 1.0 μg/ml salmon sperm DNA at 65° C. Samples and adenovirus standards were diluted and filtered onto nylon membranes using a slot blot manifold and washed with 0.4 M NaOH. The filter was hybridized with a $^{32}$P-labeled probe corresponding to the adenovirus E1A gene sequence. The entire Ad5 genome is available on Genbank at accession number X02996. We used a 1 kb SspI-XbaI fragment (corresponding to nucleotides 339–1339) and analyzed the blots on a phosphorimager (Molecular Dynamics). One genome equivalent was considered to be equivalent to one adenovirus particle.

FIG. 1 shows the results of the replication assay for rAAVCF vector in lysates prepared with Ad5 or ts149 at permissive (37° C.) and non-permissive temperatures (39.5° C.). Production of recombinant vector was supported by ts149 at 39.5° C. but productivity was approximately 2 to 3 fold less than Ad5.

Figure 2A:
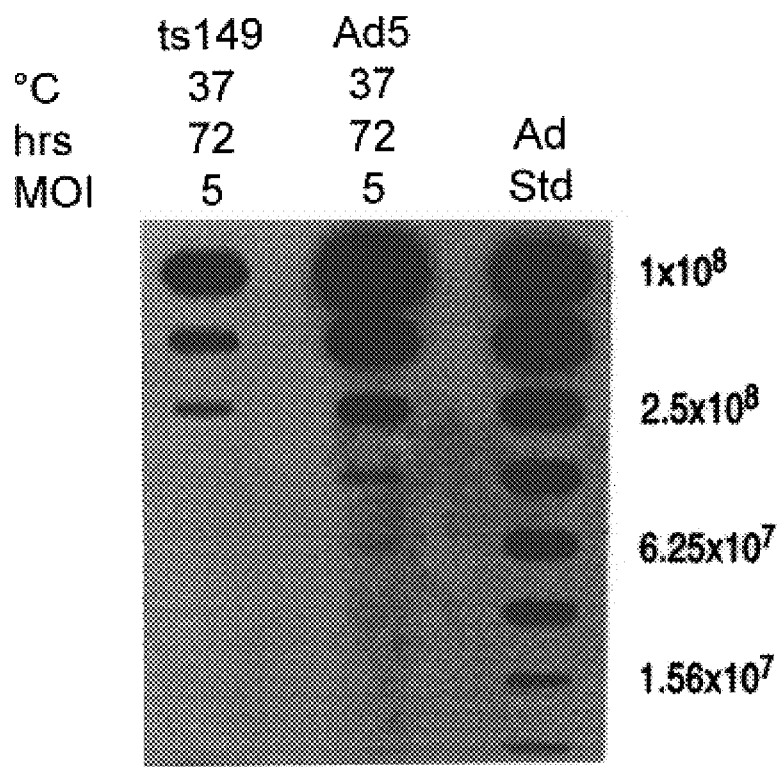
FIGS. 2A and 2B is a half-tone reproduction of a slot-blot analysis for rAAV vector production, to quantitate the level of rAAV present in each preparation. When helper function is supplied by ts149, the amount of rAAV produced under standard culture conditions is several logs below that produced in the presence of Ad5.
Figure 2B:
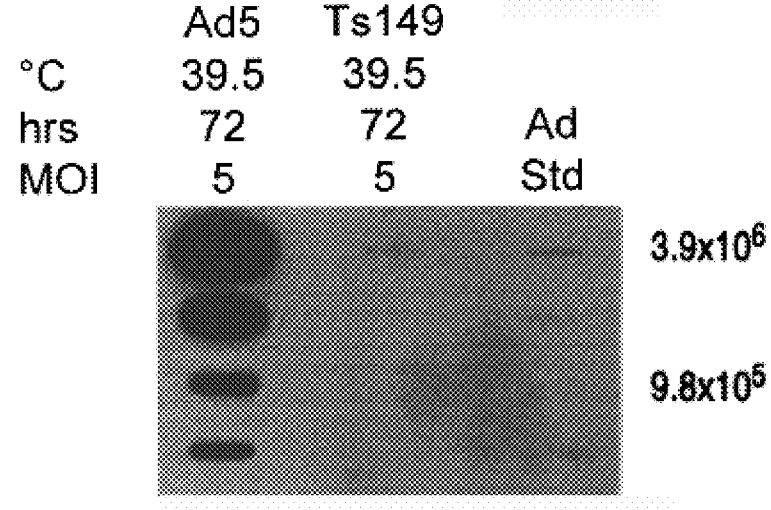

FIGS. 2A and 2B show the results of the slot blot assay to determine the quantity of adenovirus. Production of adenovirus genomes was reduced 3–4 logs by use of the temperature sensitive mutant as compared to wild-type.

Example 3

Optimization of Helper Function to Improve rAAV Production

This example illustrates various attempts to improve the level of rAAV obtained when using temperature-sensitive helper virus. Increasing infection levels of the helper virus was unhelpful, but adjusting the kinetics was surprisingly effective.

The effects of increasing multiplicity of infection on vector production was evaluated first. 293–1 cells were infected with either Ad5 at a MOI of 5 or ts149 at various MOI, followed by transient co-transfection with vector and packaging plasmids. After 72 hours, the cells were lysed and assayed for production of rAAVCF vector by C37 vector replication assay and analyzed for adenovirus production by slot-blot hybridization. An additional 96 hour time point was collected for cells infected with ts149 at a MOI of 5.

Figure 3:
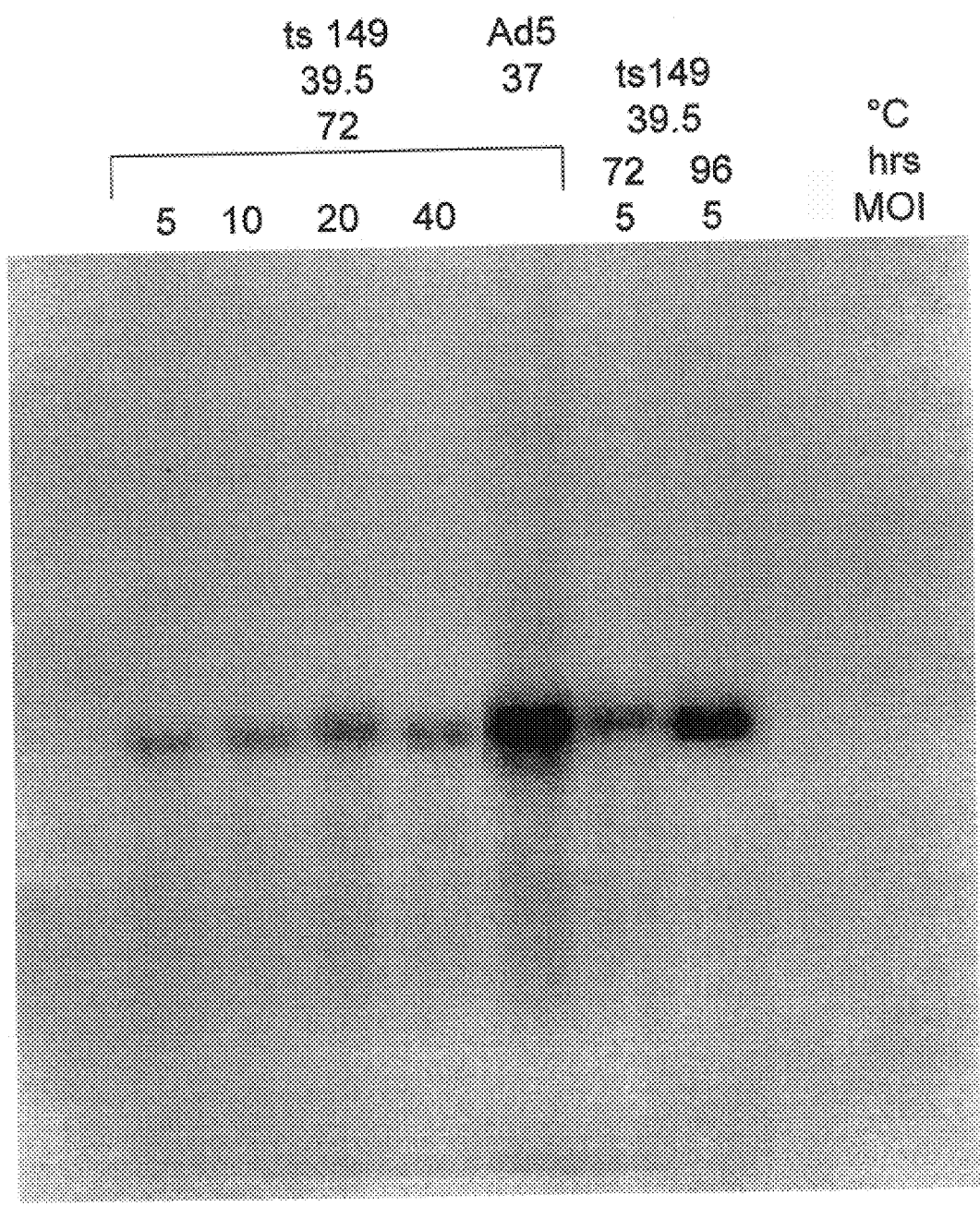
FIG. 3 is a half-tone reproduction of a Southern analysis for rAAV, indicating that increasing the level of ts149 does not improve the level of rAAV production.

FIG. 3 shows the results of the rAAVCF replication assay conducted on cell lysates prepared with ts149 at various MOI. Increasing the MOI of ts149 did not restore vector productivity to levels observed with Ad5 (as shown by the intensity of the 1.4 kb hybridization band). However, a higher level of vector production was observed at the 96 hour time point. The concentration of ts149 in the lysate detected by slot blot analysis increased with increasing MOI, but were still 3 to 4 logs lower compared with Ad5.

Following the observation of increased vector productivity with ts 149 at 96 hours in the previous experiment, a time course and production kinetic study was performed. 293–1 cells were infected with either Ad5 or ts149 at a MOI of 5 followed by transient co-transfection with vector and packaging plasmids. Cells infected with Ad5 and ts149 were cultured at 37° C. and 39.5° C.; respectively, for six days. Lysates from days 3, 4, 5 and 6 were assayed for vector production by vector replication assay and analyzed for adenovirus by slot-blot hybridization.

Figure 4:
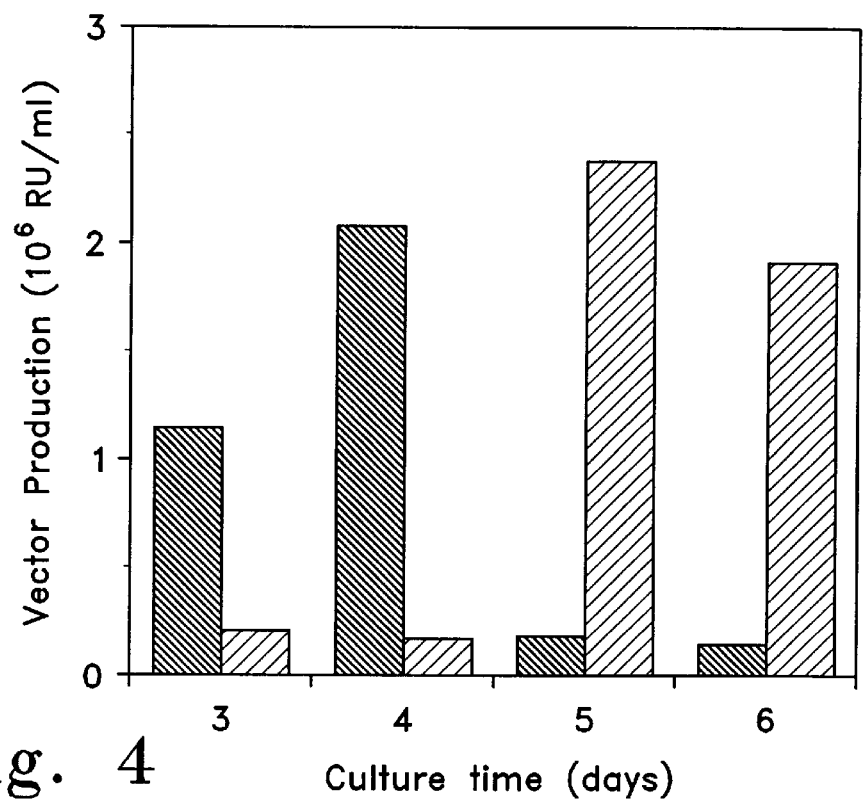
FIG. 4 is a bar graph indicating a dramatic increase in the amount of rAAV produced in the presence of ts149 (hatched bars) if culture periods are extended beyond 5 days. This is in marked contrast to the substantial decrease in rAAV that occurs beyond day 5 when non-temperature sensitive adenovirus is used to supply helper function (solid bars).

FIG. 4 illustrates the kinetics of vector production. Solid bars represent lysates produced using wild-type Ad5 as helper; hatched bars represent lysates produced using ts149 as helper. Maximal vector production when using Ad5 was ~2.0×10$^6$ RU/ml, peaking at day 4. At this time point, the vector production obtained using ts 149 was less than ~0.3×10$^6$ RU/ml. On day 5, however, there was a dramatic alteration in the relative efficacy of the two helper viruses. Vector production supported by Ad5 fell to below 0.3×10$^6$ RU/ml. In contrast, vector production supported by ts149 jumped to over 2×10$^6$ RU/ml. Adenovirus genome levels observed when using ts149 were significantly lower than with Ad5.

Example 4

Development of Suspension Cultures for Producing Helper Virus

The preceding example shows that the levels of temperature-sensitive adenovirus produced by conventional culture techniques is low. This limits the ability to use temperature-sensitive adenovirus as helpers in production of AAV vectors. The present example provides an improved method that allows for the production of temperature-sensitive adenovirus in much higher amounts. Central to the improvement is the use of host cells grown in suspension culture.

293 N3S and HeLa S3 are suspension variants of the 293–1 human embryonic kidney and HeLa human epitheloid carcinoma cell lines; respectively. Suspension cultivation was performed in 500 ml spinner flasks (Bellco) with working volumes of 250 to 300 ml. HeLa S3 (ATCC 2.2-CCL) cells were maintained in DMEM/F-12 with 15 mM HEPES supplemented with 7.5% FBS and 2.0 mM L-glutamine. 293–1 N3S (Microbix Biosystems Inc.) were passaged in Joklik MEM supplemented with 7.5% FBS and 2.0 mM L-glutamine. Spinner-flasks were agitated at 50–65 RPM.

Growth performance was assessed in the following experiment. 293 N3S and HeLa S3 were serially passaged in suspension in replicate 500 ml spinner flasks and cell growth and viability was monitored. Flasks were inoculated at cell densities of 2 to 5 ×10$^5$ cells/ml and then cultured for 2 to 3 days. To control for seeding density differences, population doubling levels (PDLs) were compared for replicate cultures. The average PDL was 2.0±0.49 (mean ± SD.) and 1.1±0.62 for HeLa S3 and 293 N3S; respectively (n=14). Higher cell doublings were consistently observed with the HeLa S3 cells. Cell morphology in suspension was dramatically different for the two lines. HeLa cells grew as single cells or small aggregates. In contrast, 293 N3S cells formed large aggregates of 50 to 100 cells each. Significant numbers of non-viable-cells were observed in the center of the large clumps. Stocks were subcultivated by centrifugation followed by gentle disruption with a pipette releasing the non viable cells from the aggregates. Initial culture viabilities of 293 N3S were consistently lower compared to HeLa S3.

Based on cell growth, viability and morphology in suspension, the HeLa S3 cell line was selected for further process development. Growth and viability at permissive temperatures were evaluated. HeLa S3 cells were seeded into 500 ml spinner flasks at 5×10$^5$ cells/ml, and monitored daily for seven days.

Figure 5:
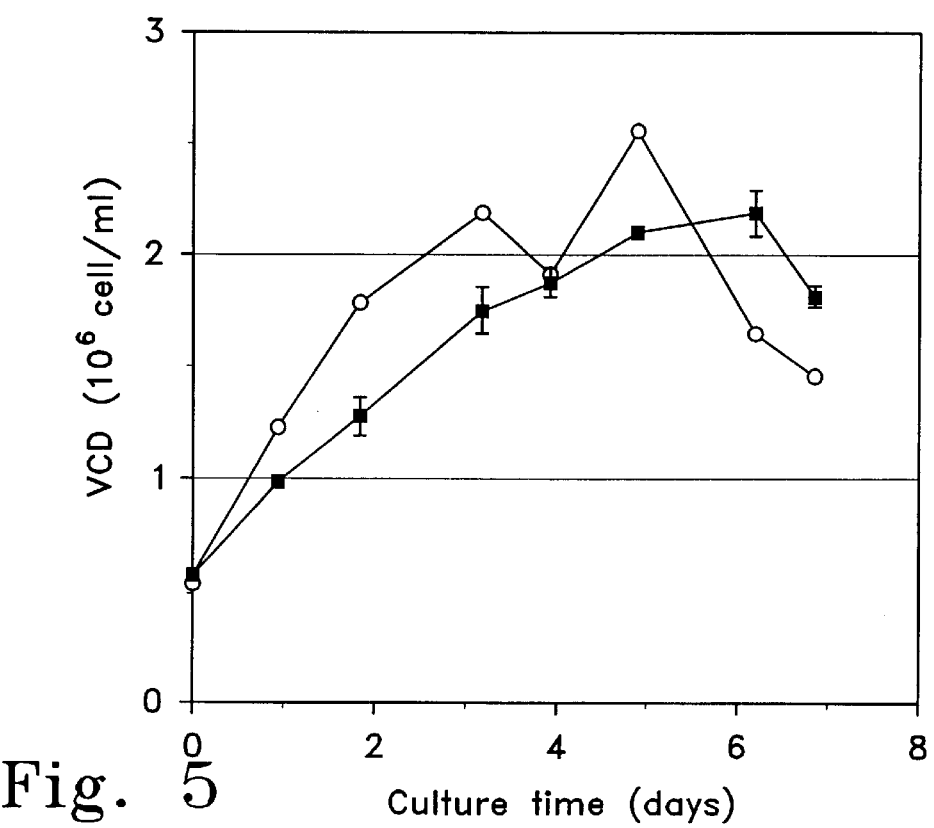
FIG. 5 is a line graph showing the viable cell density (VCD) of HeLa S3 cells grown in suspension culture at 37° C. (circles) or 32° C. (squares).

FIG. 5 shows the viable cell density (VCD) of HeLa S3 cells, grown at 32° C. (squares) and 37° C. (circles). Bars about the 32° C. time points indicate the range of values observed in replicate 500 ml spinner flasks. Cells grown at 37° C. peaked at 2.5×10$^6$ cells/ml on day 5, whereas cells grown at 32° C. peaked at 2×10$^6$ cells/ml on day 6. Viability (determined by trypan blue exclusion) was at least about 90% throughout.

Tangential flow or cross flow filtration is a versatile technique for a wide variety of large scale biopharmaceutical applications including concentration or removal of cells, concentration of macromolecules and media/buffer exchange. Tangential flow processing is required for concentrating cells for infection and for harvesting infected cells at large scale.

The effect of laminar shear on cell viability in tangential flow filtration was evaluated by concentrating and diafiltering the HeLa S3 cells. HeLa S3 cells were inoculated at a density of 4×10$^5$ cells/ml in three liter Applikon bioreactors and cultured to 2×10$^6$ cells/ml in DMEM/F-12 with 15 mM HEPES (JRH) supplemented with 7.5% FBS, 2.0 mM glutamine, 1 X MEM amino acids, 1 X MEM non-essential amino acids, 0.1% Pluronic polyol F-68 and 2 g/L glucose. Bioreactor working volume was two liters. Dissolved oxygen, pH, temperature and agitation were controlled at 60% (relative to air saturation), 7.2, 37° C. and 100 rpm; respectively, using the FERMCON™ (Scius Corporation) controller system.

Tangential flow filtration experiments were performed with mixed cellulose ester hollow fiber membranes (Microgon). Pore size and surface area was 0.2 μ and 725 cm$^2$; respectively. A 0.2 μ filter was selected to retain cells while allowing passage of spent media. Cells were pumped (Cole Palmer) through the inside diameter of the hollow fibers. Recirculation rates were adjusted to provide average wall shear rates of 750 and 1500 sec$^{-1}$. Once the crossflow was established, permeate flow control of 30 and 90 ml/min; respectively, was achieved by a pump (Cole Palmer) located on the permeate line. During cell concentration, permeate withdrawal continued until the desired fold concentration was achieved. During diafiltration, media feed entering the bioreactor was activated until the desired fold medium exchange was achieved. Viable cells were counted before and after each treatment.

Figure 6:
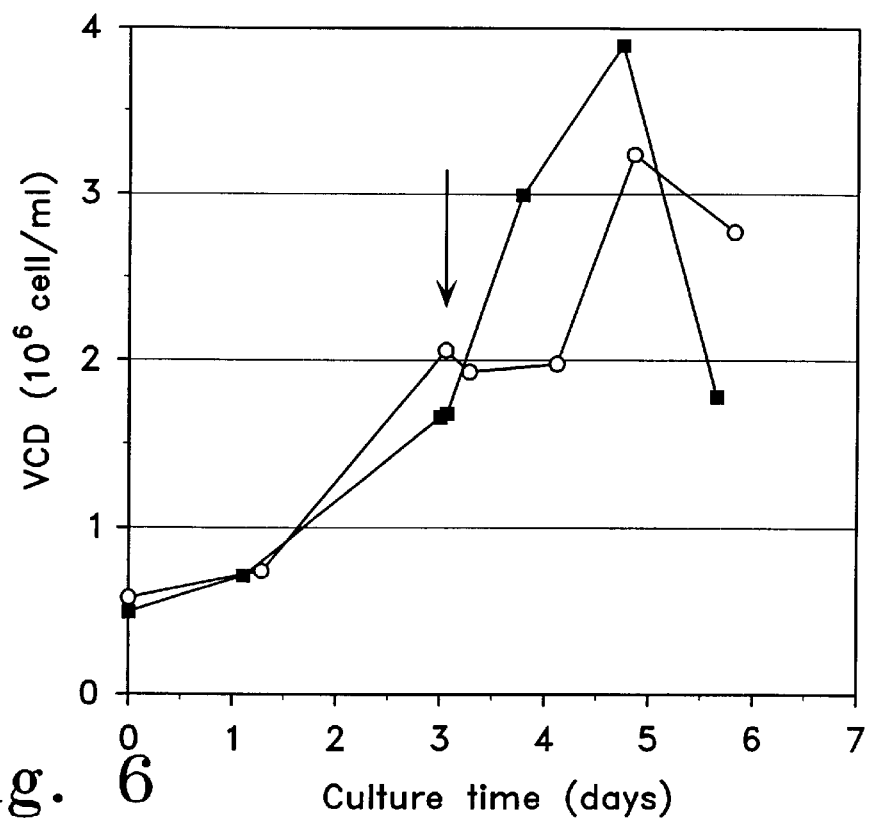
FIG. 6 is a line graph showing the effect of tangential flow filtration at two different rates on HeLa S3 cells grown in suspension culture.

FIG. 6 shows the growth curves of HeLa S3 cells before and after tangential flow processing in an exemplary experiment. Two liters of cells were cultured in 3 liter bioreactors. On day 3 (arrow), cells were concentrated seven fold from the 2-liter working volume, diafiltered against six volumes of growth medium and brought up to the original working volume. The results show that the cells were not damaged by wall shear of 750 sec$^{-1}$ (squares) and 1500 sec$^{-1}$ (circles), and continued to grow to high cell densities.

Suspension cultures of HeLa S3 cells were then tested as host cells for ts149 production. or their ability in 300 ml suspension culture was investigated. HeLa S3 cells from 300 ml suspension culture ($1\times10^6$ cells/ml) were centrifuged, concentrated and infected with ts149 (MOI=3). After 1 hour, the culture was transferred to a spinner-flask, resuspended in media and cultured for seven days at 32° C. The HeLa S3 cells continued to grow from about $1 \times10^6$ cells/ml at the time of infection to about $2\times10^6$ cells/ml by day 5. Viability decreased to ~60% on day 7.

Figure 7:
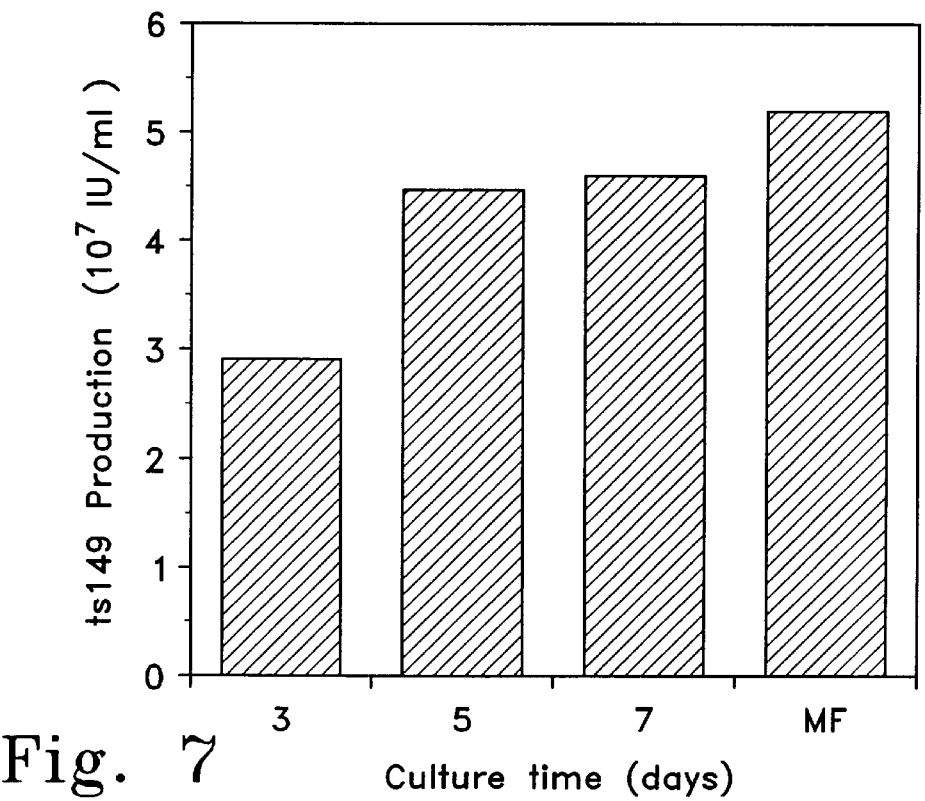
FIG. 7 is a bar graph showing the production of ts149 detected in infected HeLa S3 cells cultured for 3–7 days in suspension at the permissive temperature of 32° C., compared with the level detected at day 7 after microfluidization (MF).

FIG. 7 shows the production of ts149 by HeLa S3 cell cultures. The culture was sampled daily, and lysates were prepared by freeze-thaw for analysis of virus production by the adenovirus infectivity assay. Virus production reached ~$4.5\times10^7$ IU/ml of culture by about day 3–5. On day 7, the cells were collected by centrifugation, resuspended in TMEG 5 buffer and lysed by microfluidization (MF). The infectious titer of the microfluidized lysate was comparable to those of the freeze-thaw lysate sample indicating recovery by microfluidization was comparable to freeze-thaw methods.

Example 5

Improved Purification Method for the Production of a Temperature-Sensitive Helper Virus (AD TS149)

Purification using CsCl gradients is burdensome for large scale production. This example illustrates the purification of ts149 by ion exchange chromatography.

Chromatography was performed on a Perseptive Biosystem BIOCAD™ chromatography workstation. The resin used was a polyethyleneimine (PI) weak anion exchanger (POROS™ 50 PI). The column was equilibrated with TMEG (50 mM Tris, pH 8.0, 5 mM MgCl$_2$, 1 mM EDTA, 5% glycerol). Chromatography was monitored on-line for pH, conductivity and optical density at 280 nm.

Suspension HeLa S3 infected with ts149 at a MOI of 2 was harvested and centrifuged. The pellet was resuspended in TMEG and lysed by cavitation at 3000 PSI using a microfluidizer (Microfluidics). Lysate was clarified by filtration through a 5 μ syringe filter (Millex SV) followed by a 0.45 μ syringe filter (Acrodisc). Clarified lysate was loaded onto a 1.6 ml POROS™ 50 PI anion exchange column run at 1 ml/min. The column was washed with 10 column volumes of TMEG with 900 mM NaCl, and the ts149 was eluted with a linear gradient from 900 to 1300 mM NaCl. Fractions of 0.5 ml were collected and assayed by infectivity assay and slot blot for the presence of adenovirus.

Figure 8A:
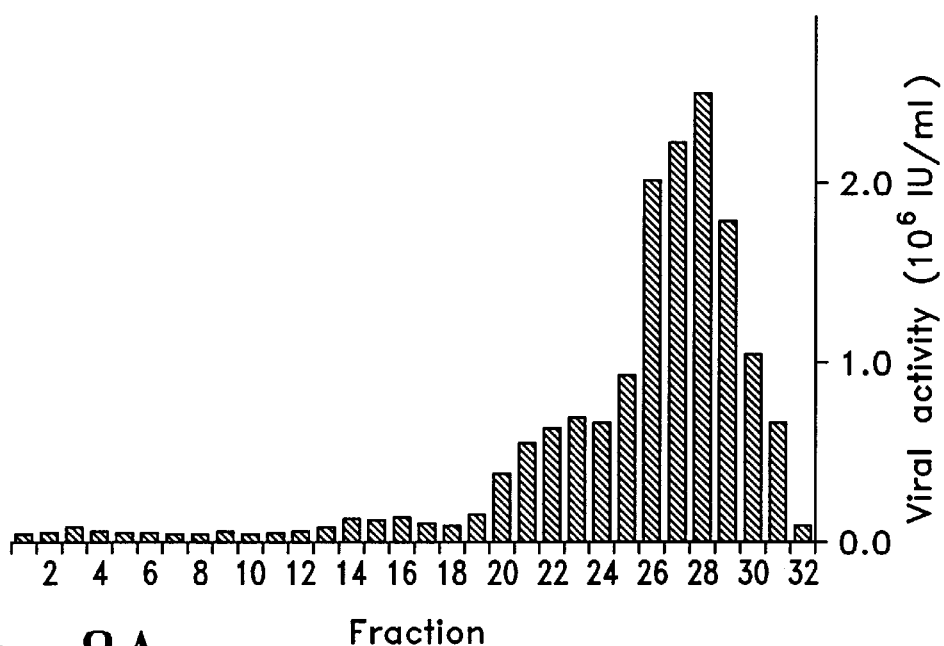
FIGS. 8A and 8B is a combination graph showing the purification of ts149 by anion exchange chromatography on PI matrix, eluted with a linear 900–1300 meq NaCl gradient at pH 8.0.
Figure 8B:
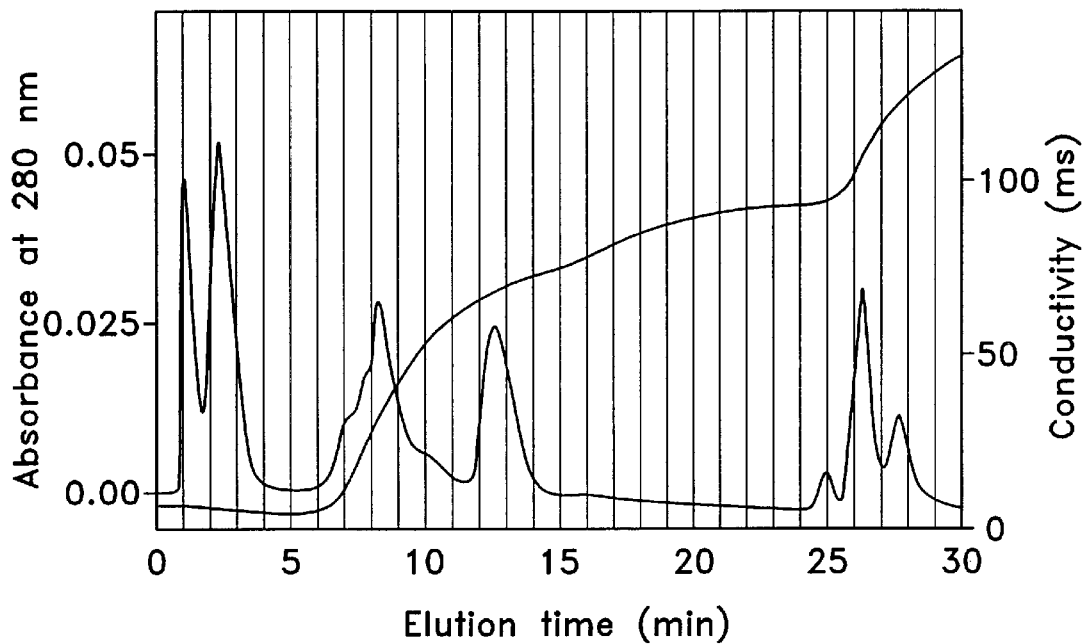

FIG. 8 shows the results of the infectivity assay conducted on consecutive column fractions. The majority of the infectious adenovirus was found in fractions 26 to 28, coincident to the peak of absorbance eluting at about 100 ms at approximately 25 minutes. The ts149 eluted just prior to the large peak at higher salt concentration. Infectivity and slot blot assays conducted in parallel confirmed particles and infectious virus were in the same peak fractions.

Lysate and PI peak fractions were also assayed for total protein by the Bradford method. Protein concentration was 1.8 mg/ml in the lysate and less than 30.0 μg/ml in the PI pool. The virions were separated from the majority of cellular protein in a single step and eluted as a single peak. The virions showed very high affinity for the PI matrix, as evidenced by the relatively high salt concentration required to elute them from the column.

Large-scale production method for temperature-sensitive helper virus can incorporate all the improvements described in these examples. In one illustration, virus production would comprise the following steps:

Cell culture in suspension bioreactor
Concentration/Medium exchange
Infection with helper virus
Virus production
Harvest: Concentration/Diafiltration
Lysis by microfluidization
PI ion-exchange chromatography
Concentration/Diafiltration
Sterile filtration This type of approach is inherently scalable and amenable to current Good Manufacturing Practices.

Additional exemplary illustrations of such techniques are provided below.

Example 6

Comparison of First and Second Generation Processes for Helper Virus Production

A. Illustrative First Generation Helper Virus Production and Processing

In an exemplary "first generation" process for helper virus production, mammalian cells were grown in 40 T225 flasks, and then infected with Ad5 at an MOI of about 1. After incubating, the cells were harvested by centrifugation, and lysed by freeze-thawing and passage through a needle. The lysate was subjected to treatment with DNase I and then run on a step CsCl gradient and isopycnic gradient. Purified material was dialyzed and sterile filtered.

Using this first generation process, we obtained approximately $1\times10^{12}$ particles (or approx. $1\times10^{11}$ infectious units) from $4\times10^8$ cells.

B. Illustrative Second Generation Helper Virus Production and Processing

In an exemplary "second generation" process for helper virus production, mammalian cells (HeLa S3) were grown in 10 liter bioreactors, and then infected with Ad5 (from ATCC, subsequently plaque-purified on 293 cells, serially expanded on HeLa S3 cells and double purified by CsCl gradient centrifugation) at an MOI of about 1. After incubating, the cells were concentrated and harvested by diafiltration, and lysed by microfluidization. The lysate was subjected to treatment with Benzonase (nuclease) and then filtered. The filtrate was then run on an anion exchange column (PI) concentrated and diafiltered, and finally sterile filtered.

Using this second generation process, we obtained approximately $1\times10^{14}$ particles (or approx. $5\times10^{12}$ infectious units) from $1\times10^{10}$ cells.

Figure 9:
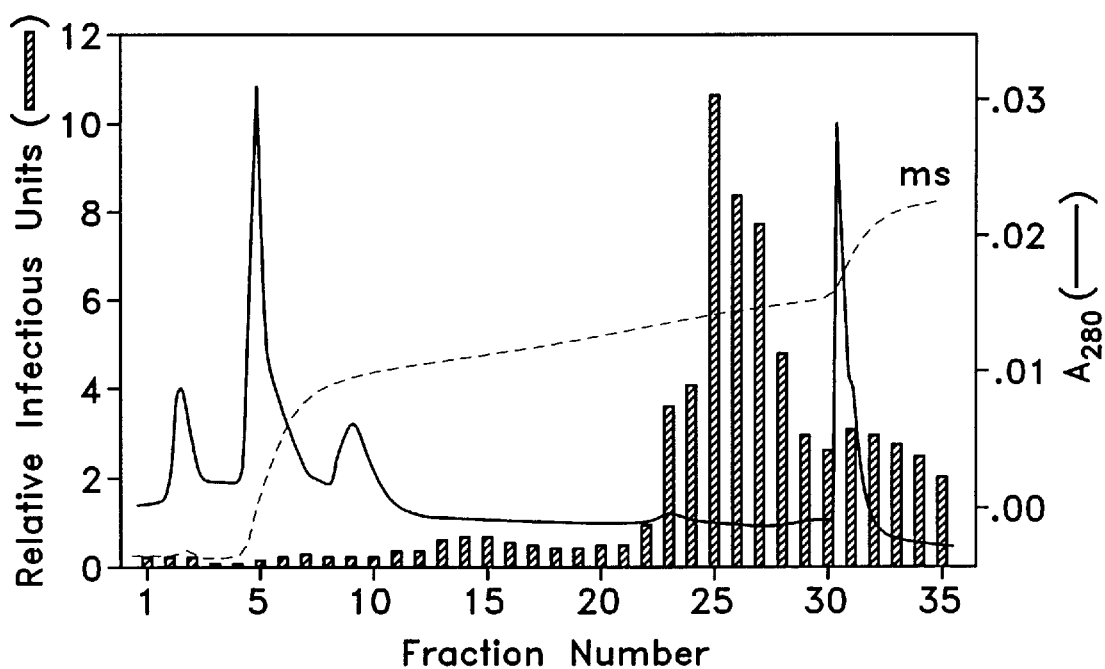
FIG. 9 is a combination graph showing the purification of Adenovirus on PI anion-exchange matrix, eluted with a 800–1300 meq gradient of NaCl at pH8.0. Bars: Viral activity measured in an infectivity assay; Solid line: $A_{280}$ (a measure of total protein); Dotted line: buffer conductivity (mS).

FIG. 9 illustrates the results of the downstream processing of helper virus using anion exchange chromatography as described above. Bars: Viral activity measured in an infectivity assay; Solid line: $A_{280}$; Dotted line: buffer conductivity (mS).

As is apparent from comparing the fractionation of viral activity versus A280 absorbance, these processing procedures resulted in a substantial separation of the helper virus from the bulk of contaminating materials which would be expected to contain cellular proteins and nucleic acids.

Example 7

Comparison of First and Second Generation Processes for Production of Recombinant AAV Vectors A. Illustrative First Generation rAAV Production and Processing In an exemplary "first generation" process for rAAV vector production, mammalian cells were grown in 40 T225 flasks, and then infected with Ad5 at an MOI of about 5. After incubating, the cells were harvested by centrifugation, and lysed by sonication. The lysate was subjected to treatment with DNase I and then run on a series of two CsCl gradients. Purified material was dialyzed and sterile filtered. Using this first generation process, we obtained approximately $5\times10^6$ replicative units RUs from $4\times10^8$ cells.

B. Illustrative Second Generation rAAV Production and Processing

In an exemplary "second generation" process for rAAV vector production, mammalian cells were grown in 10 liter bioreactors, and then infected with Ad5 at an MOI of about 5. After incubating, the cells were concentrated and harvested by diafiltration, and lysed by microfluidization. The lysate was subjected to treatment with Benzonase (nuclease) and then filtered. The filtrate was then run on anion exchange column, followed by a cation exchange column. Eluant fractions containing AAV were pooled, concentrated and diafiltered, and finally sterile filtered. This second generation process is expected to yield greater than $1\times10^{11}$ replicative units RUs from $1\times10^{10}$ cells.

Figure 10A:
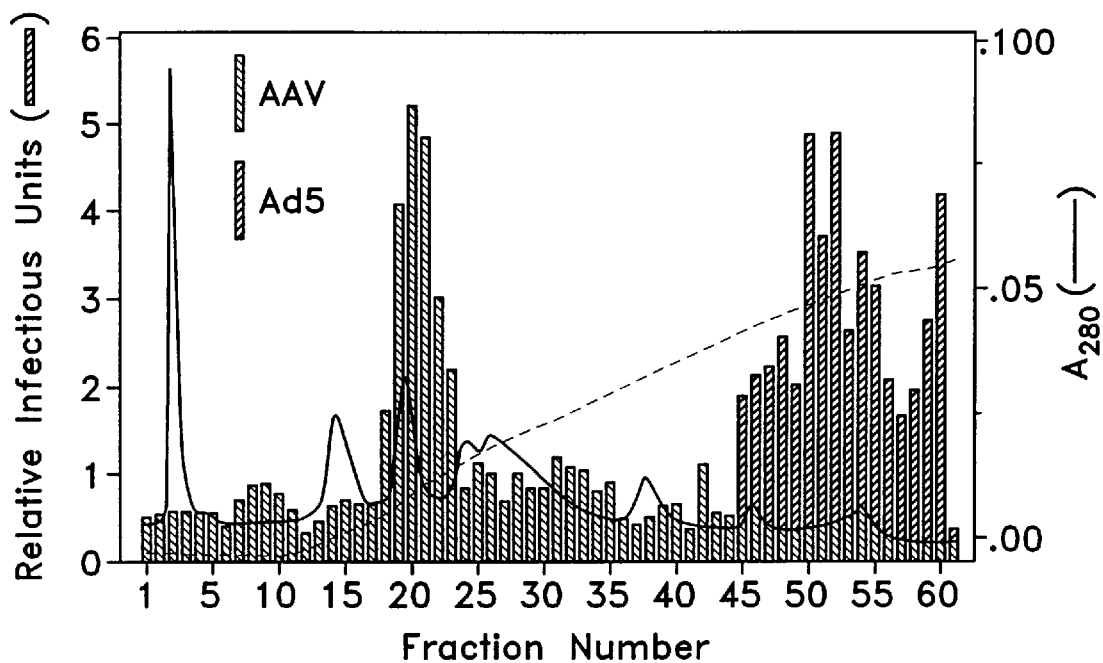
FIGS. 10A and 10B is a combination graph showing the separation of Adenovirus and recombinant AAV. The upper panel shows separation on PI anion-exchange matrix, eluted with a 0–1000 meq gradient of NaCl at pH 8.0. The lower panel shows subsequent separation of Adenovirus from contaminants on HS cation-exchange matrix, eluted with a 0–500 meq gradient of NaCl at pH 8.0.
Figure 10B:
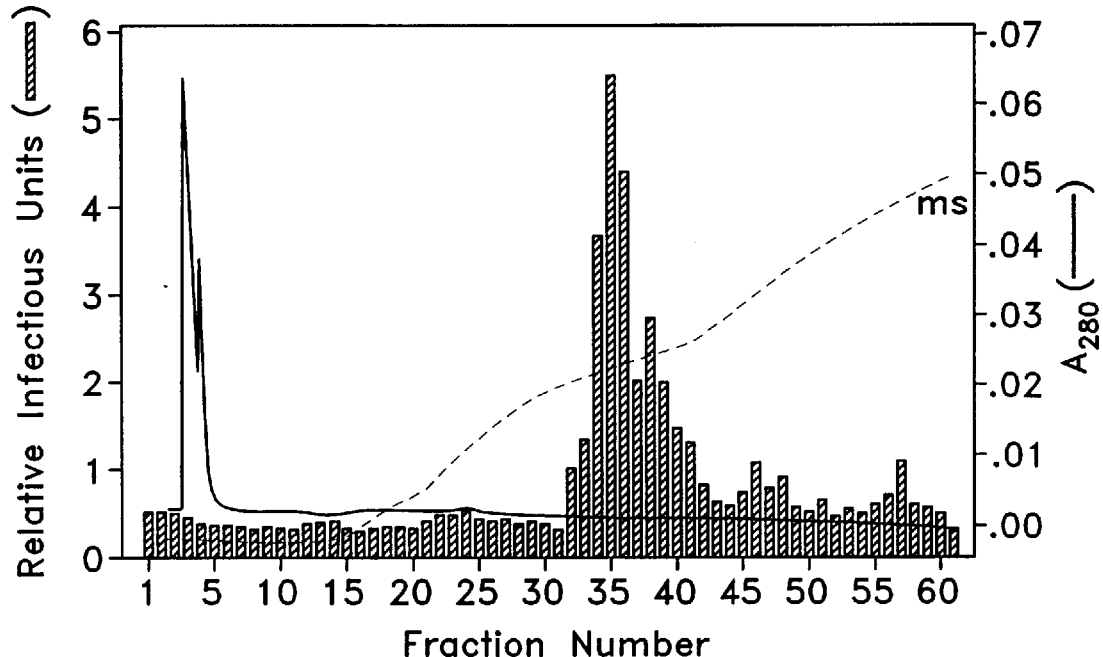

FIG. 10 show the results of sequential fractionation on ion exchange columns: first, on an anion exchange matrix (upper panel), and then on a cation exchange matrix (lower panel). Bars: Viral activity measured in an infectivity assay for either Adenovirus or AAV; Solid line: $A_{280}$ (a measure of total protein); Dotted line: buffer conductivity (mS). As is apparent from the analyzed fractions, it is possible to obtain extremely high levels of separation between AAV and Adenovirus, as well as between AAV and A280-absorbing material (largely proteins) using the techniques of the present invention. In particular, the results revealed that AAV vectors can be retained on both anionic and cationic exchange columns, and that the differential elution of AAV using both anionic and cationic exchange resulted in dramatically enhanced ability to separate AAV from all of the major contaminants of interest (including Adenovirus as well as cellular proteins).

In another exemplary second generation process for rAAV vector production, the filtrate was prepared as described above and was then run on an anion exchange column, followed by pooling of eluant fractions containing AAV, and then subjecting the pooled anion exchange eluants to tangential flow filtration (TFF). As described below, this anion exchange to TFF procedure was found to result in a highly conentrated and purified preparation of AAV.

Figure 11A:
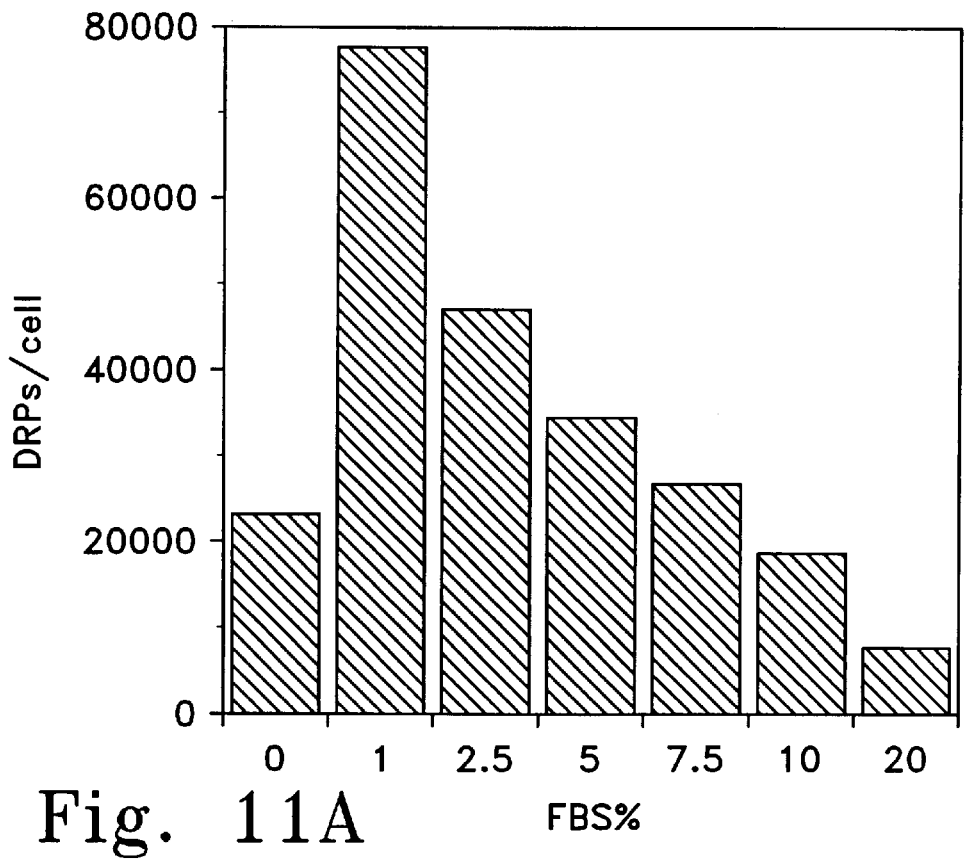
FIGS. 11A and 11B is two bar graphs, showing the effect of fetal bovine serum levels (FBS) in the culture medium on rAAV production. The upper graph indicates DRPs; the lower graph indicates RUs. Serum deficiency in the culture medium is one of a number of stress factors that the producer cells can be subjected to in order to enhance the production of viral particles.
Figure 11B:
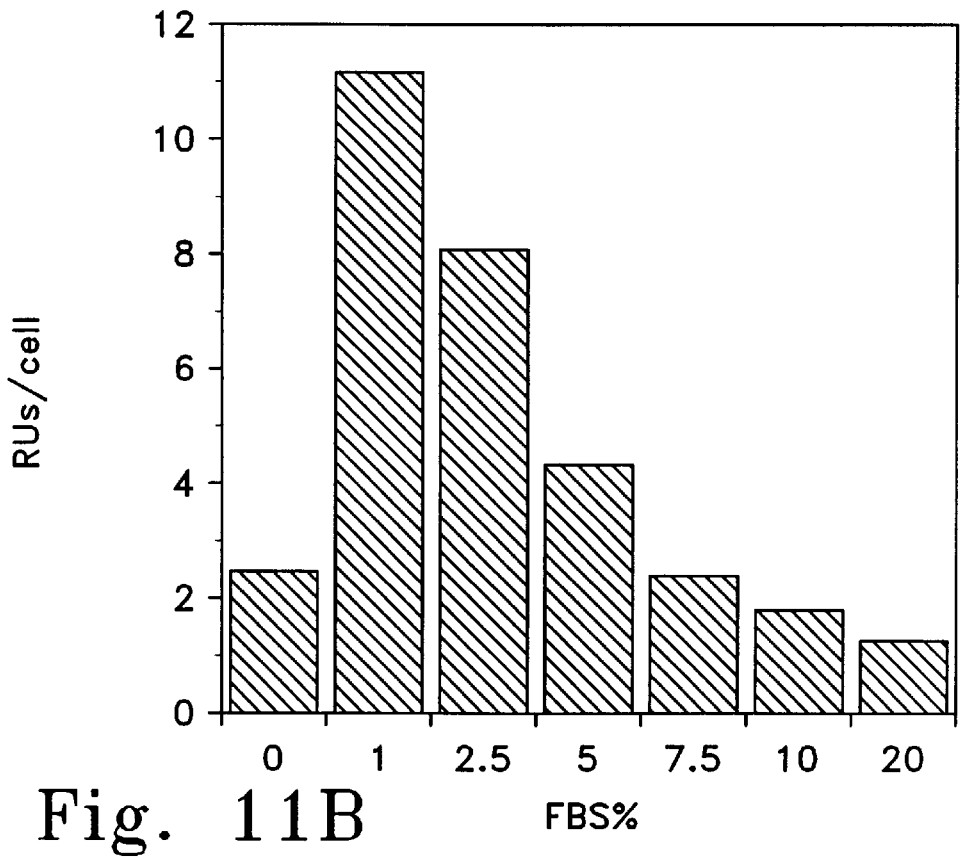

Detailed analysis of AAV obtained using such second generation technology, using techniques as described above and in the art (including infectivity assays, slot blot analyses and SDS gel electrophoresis) provided further confirmation that the material was of high quality and substantially free of contaminating adenovirus particles (and adenovirus protein and DNA), and also substantially free of contaminating cellular proteins and DNA. SDS gels revealed the presence of bands corresponding to VP1, VP2 and VP3 (i.e. the AAV capsid proteins). No other bands were visible after Coomassie staining. These data are consistent with the results of the column fractionation analyses as depicted in FIGS. 10–11.

As an illustrative anion exchange to TFF procedure, the following is an examplary purification and concentration process starting with one liter of pooled fractions from anion exchange chromatography. If desired (as noted above), this pool can be subjected to heat inactivation followed by a filtration step (e.g., using a 0.22 μm filter). For tangential flow filtration (TFF), we employed a sanitized Pellicon XL system equipped with a 300,000 molecular weight cut-off membrane which was operated at 40/0 for inlet and outlet pressures. One liter of pooled material was loaded into the system at a 500 ml volume and then concentrated to 250 ml. Diafiltration was performed with 5 diavolumes (1250 ml) of Modified Ringer's Solution +5% glycerol. Following diafiltration, the retentate was concentrated to a final volume of 14 ml. Total process time was approximately 3.25 hours (not including sanitization time). Silver-stained SDS gels, slot blots, and infectivity assays confirmed that the AAV preparation (which contained approximately $10^{10}$ replicative units) was substantially free of contaminating adenovirus as well as adenoviral and cellular proteins.

The following are results from such a procedure showing infectious and total virus titer as RU (replicative units) and DRP (DNAse-resistant particles) respectively:

300K TFF Volume Total RU Total DRP P/I %RU %DRP
Input Pool 1000ml $8.9\times10^{10}$ $3.1\times10^{14}$ 3483 100 100
Purified Bulk 12.5 ml $7.3\times10^{10}$ $2.3\times10^{14}$ 3103 82 74

Figure 12:
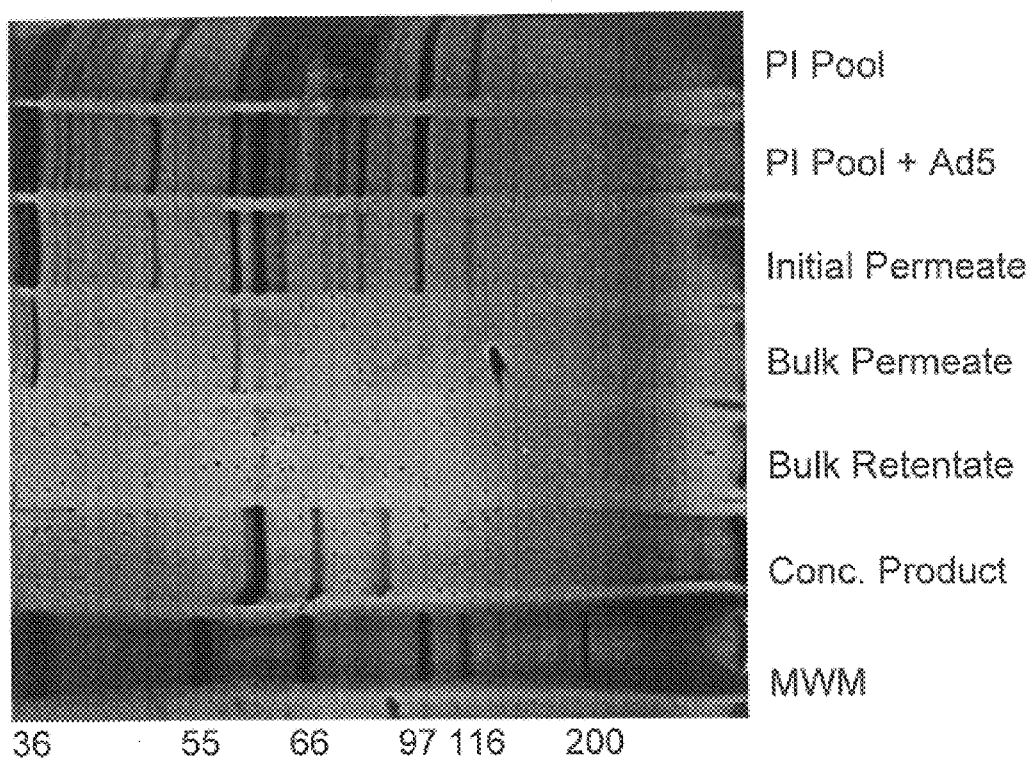
FIG. 12 is a half-tone reproduction of a SDS-polyacrylamide gel analysis for AAV proteins during purification steps. The AAV preparation was subjected to tangential flow filtration after chromatography on an anion exchange column (POROS 50 PI). The silver stained gel shows the highly purified AAV capsid proteins, VP1, VP2, and VP3 in the final bulk material.

The data presented in FIG. 12 illustrates the results of an AAV production run using tangential flow filtration after an anion exchange column. Material purified on the POROS 50 PI column was concentrated using a 300,000 molecular weight cut-off membrane (Millipore Pellicon XL). The concentrated material was diafiltered with five successive volumes of Ringer's Balanced Salt Solution +5% glycerol. The material was then concentrated on the membrane 10-fold. FIG. 12, a half-tone reproduction of an SDS polyacrylamide gel stained with a silver stain, shows the highly-purified AAV capsid proteins, VP1 (85 kD), VP2 (72 kD), and VP3 (62 kD), in the final purified bulk material.

As is apparent from the data presented herein, these second generation techniques for the preparation and purification of AAV result in substantially improved methods as compared with those described previously.

Exemplary media for growing the Adenovirus helper and for preparing rAAV are detailed in the following Table:

TABLE 2

|  | Ad medium | rAAV medium |
|---|---|---|
| INORGANIC SALTS |  |  |
| CaCL | 116.61 |  |
| CuSO4*5H2O | 0.00125 | 0.00125 |
| Fe(NO3)3*9H2O | 0.05 | 0.05 |
| FeSO4.7H2O | 0.417 | 0.417 |
| KCL | 311.8 | 311.8 |
| MgCl2 | 28.61 |  |
| MgSO4 | 48.84 |  |

TABLE 2-continued

|  | Ad medium | rAAV medium |
|---|---|---|
| NaCl | * | * |
| NaHCO3 | 2200 | 2200 |
| NaH2PO4.H2O | 62.5 | 62.5 |
| Na2HPO4 | 71.02 | 71.02 |
| Zn2SO4.7H2O | 0.4315 | 0.4315 |
| OTHER COMPONENTS | | |
| Glucose | 4500 | 4500 |
| HEPES | 3575 | 3575 |
| Hypozanthine Na | 2.39 | 2.39 |
| Linoleic acid | 0.042 | 0.042 |
| Lipoic acid | 0.105 | 0.105 |
| Phenol Red, Na Salt | | |
| Putrescine.2HCL | 0.081 | 0.081 |
| Sodium Pyruvate | 55 | 55 |
| Pluronic Polyol F-68 | 100 | 100 |
| AMINO ACIDS | | |
| L-Alanine | 4,455 | 4,455 |
| L-Arginine.HCL | 273.9 | 273.9 |
| L-Asparagine.H2O | 22.5 | 22.5 |
| L-Aspartic | 19.95 | 19.95 |
| L-Cysteine.HCL.H2O | 17.56 | 17.56 |
| L-Cystine.2HCL | 52.29 | 52.29 |
| L-Glutamic acid | 22.05 | 22.05 |
| L-Glutamine | 657 | 657 |
| Glycine | 26.25 | 26.25 |
| L-Histidine.HCL.H2O | 73.48 | 73.48 |
| L-Isoleucine | 106.97 | 106.97 |
| L-Leucine | 111.45 | 111.45 |
| L-Lysine.HCL | 163.75 | 163.75 |
| L-Methionine | 32.34 | 32.34 |
| L-Phenylalanine | 68.48 | 68.48 |
| L-Proline | 17.25 | 17.25 |
| L-Serine | 36.75 | 36.75 |
| L-Threonine | 101.05 | 101.05 |
| L-Tryptophan | 19.22 | 19.22 |
| L-Tyrosine | 91.79 | 91.79 |
| L-Valine | 99.65 | 99.65 |
| VITAMINS | | |
| d-Biotin | 0.00365 | 0.00365 |
| D-Ca Pantothenate | 2.24 | 1.00 |
| Choline Chloride | 8.98 | 8.98 |
| Folic Acid | 2.65 | 2.65 |
| myo-inositol | 12.6 | 12.6 |
| Niacinamide | 2.0185 | 2.0185 |
| Pyridoxal.HCL | 2 | 2 |
| Pyridoxine.HCL | 0.031 | 0.031 |
| Riboflavin | 0.219 | 0.219 |
| Thiamine.HCL | 2.17 | 2.17 |
| Thymidine | 0.365 | 0.365 |
| Vitamine B12 | 0.68 | 0.68 |

*add appropriate amount of NaCl for osmolality of 300 mOsM (+ or −20 mOsM)

C. Purification of AAV Vector Using Heparin Sulfate Chromatography

As discussed above, chromatographic techniques can be employed to further purify and concentrate AAV preparations in acccordance with the present invention. By way of illustration, a preparation of AAV which is in crude form (e.g. lysate), or which has been eluted from an anion-exchange or cation-exchange column and/or concentrated by tangential flow filtration can be purified by binding to a column comprising heparin sulfate. The AAV can then be eluted from such a column using a buffer containing a salt (e.g. a linear gradient of NaCl).

As illustrative of the use of heparin sulfate chromatography, AAV obtained from a "PI" pool (as described below in Example 9) was first concentrated four-fold and diafiltered into TMEG +100 mM NaCl using a 300K tangential flow filtration membrane. The concentrate was then injected on a 1 ml heparin sulfate column (Pharmacia "Hi-Trap Heparin" column), and eluted using a linear gradient of NaCl.

Figure 13:
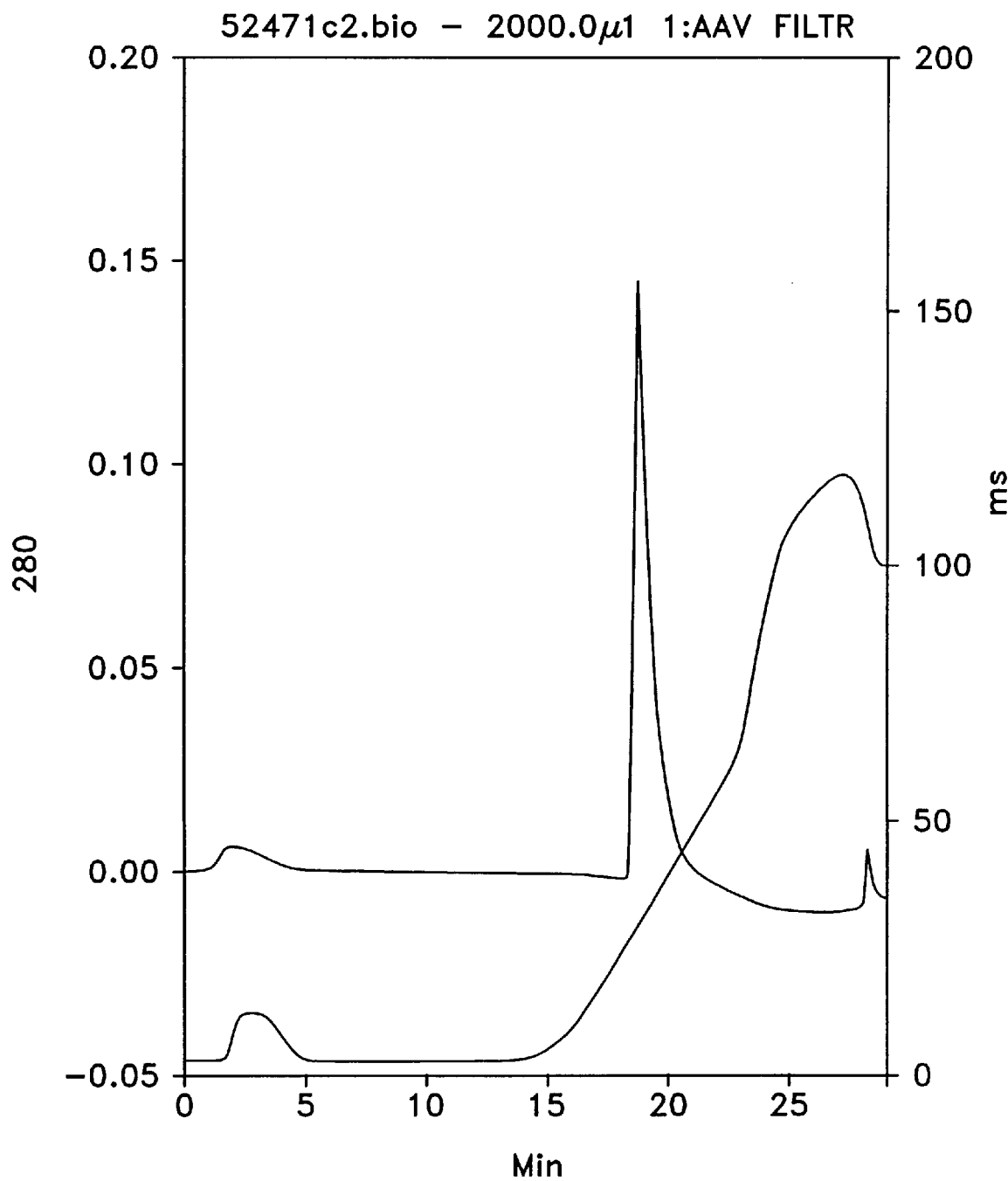
FIG. 13 is a chromatogram showing concentration of AAV on a heparin sulfate column. The sharp peak in absorbance at 280 nm (left-hand axis) at about 18 minutes elution time represents the AAV fraction (after anion exchange and tangential flow filtration) as eluted from heparin sulfate with a linear gradient of 0 to 1 M NaCl (conductivity in ms shown on right-hand axis).

FIG. 13 is a chromatogram showing the resulting concentration of AAV on the heparin sulfate column. The sharp peak in absorbance at 280 nm (left-hand axis) at about 18 minutes elution time represents the AAV fraction as eluted from heparin sulfate with a linear gradient of 0 to 1M NaCl (conductivity in ms shown on right-hand axis).

Example 8

Recombinant AAV Vector Production and Testing

In another set of production runs, we used 3–4×10$^9$ cells grown in a Cell Factory, using DMEM +10% FBS as the growth medium. Cells were infected with Ad at an MOI of about 20, and harvested at 72 hours post-infection. Harvested cells were suspended in TMEG+ NaCl at a concentration of about 5×10$^6$ cells/ml. After mechanical lysis (microfluidization, 2 passes at 8000 psi), lysates were treated with Benzonase (25 units/ml, 37 degrees C., one hour), and then filtered through a 5 micron filter (Pall Profile 11).

As an exemplary anion exchange column, we employed the POROS50 PI column (available from Perseptive Biosystems). Briefly, the filtrate was loaded onto the column in about 100 ml and eluted with a gradient of NaCl to 500 mM. Fractions determined (by infectivity assay) to contain the majority of the AAV were collected and pooled (referred to as the "PI pool").

The PI pool was then diluted about 1:7 in TMEG and loaded on a 50 ml Toso Haas SP650C column, and eluted with a gradient to 500 mM NaCl. Fractions determined (by infectivity assay) to contain the majority of the AAV were collected and pooled (referred to as the "SP pool"). The SP pool was concentrated using a Centriprep 10 K filter, and then was sterilized by passage through a 0.2 micron filter.

The results revealed that the recombinant AAV was essentially free of detectable infectious adenovirus (as determined by limit of detection analysis with serial amplification on 293 cells and TCID50 assay). The preparation was also essentially free of adenoviral DNA (as determined by slot blot analysis), essentially free of cellular proteins (as determined by SDS-PAGE gel analysis), of cellular DNA (determined by PCR analysis), and was also essentially free of phenotypically wild-type AAV (as determined by serial amplification and Southern analysis).

Example 9

The Enhancement of AAV Production by Nutritional Stress

As discussed above, it is believed that AAV production can be enhanced using any of a variety of agents and/or conditions that effectively stress (or de-optimize) growth or metabolism of the AAV producer cells. In this example, it is shown that the depletion of certain amino acids as occurs during culture is associated with a relative enhancement in AAV production; and, conversely, that media supplements to remove the nutritional stress actually result in a dramatic reduction in vector yield.

(a) Nutritional stress during batch and perfusion culture

JL14 cells were inoculated at about 4×10$^5$ cells/ml in 2 liter bioreactors and grown in the rAAV medium shown in Table 2 in either batch mode or by perfusion (using tangential flow filtration, day 1 at 0.4 volumes/day, days 2–3 at 1.2 vol./day, day 4 at 2 vol./day and day 5 at 4 vol./day). Cultures were monitored for cell density, glucose, lactate and amino acids using standard techniques.

The analyses revealed that cell density peaked in batch culture at 1×10$^6$ cells/ml on day 2, and in perfusion culture at 8×10$^6$ cells/ml on day 6. Glucose was not limiting in either case (>1 g/l) and lacate was not inhibitory.

However, amino acid analysis revealed that both glutamate and aspartate were rapidly depleted in both batch and perfusion cultures, as shown in the following Tables:

TABLE 3

Amino acid analysis of BATCH culture medium
(time course-µmol/L)

| | MW | day 0 | day 1 | day 2 | day 3 | day 4 |
|---|---|---|---|---|---|---|
| Aspartic Acid | 133 | 96 | 10 | 4 | 9 | 7 |
| Threonine | 119 | 687 | 644 | 606 | 552 | 533 |
| Serine | 105 | 271 | 230 | 157 | 117 | 98 |
| Asparagine | 132 | 130 | 113 | 96 | 68 | 69 |
| Glutamic Acid | 147 | 90 | 2 | 1 | 1 | 1 |
| Glutamine | 146 | 3424 | 2987 | 2450 | 1989 | 1843 |
| Proline | 115 | 135 | 143 | 162 | 164 | 185 |
| Glycine | 75 | 288 | 241 | 194 | 151 | 130 |
| Alanine | 89 | 189 | 306 | 438 | 644 | 681 |
| Valine | 117 | 692 | 631 | 518 | 417 | 342 |
| Cystine | 121 | 143 | 133 | 120 | 107 | 99 |
| Methionine | 149 | 160 | 132 | 100 | 74 | 58 |
| Isoleucine | 131 | 617 | 531 | 383 | 264 | 182 |
| Leucine | 131 | 645 | 538 | 374 | 248 | 161 |
| Tryosine | 181 | 407 | 379 | 355 | 329 | 315 |
| Phenylalanine | 165 | 323 | 289 | 259 | 231 | 214 |
| Tryptophan | 204 | 47 | 41 | 33 | 28 | 26 |
| Ammonia | 17 | 760 | 816 | 941 | 1021 | 1033 |
| Ornthinine | | 71 | 89 | 110 | 128 | 144 |
| Lysine HCl | | 572 | 521 | 463 | 415 | 384 |
| Histidine | 155 | 276 | 257 | 243 | 229 | 211 |
| Arginine | 174 | 1020 | 943 | 870 | 791 | 747 |

TABLE 4

Amino acid analysis of PERFUSION culture medium
(Time course-µmol/L)

| | MW | day 0 | day 1 | day 2 | day 3 | day 4 | day 5 | day 6 |
|---|---|---|---|---|---|---|---|---|
| Aspartic Acid | 133 | 95 | 12 | 5 | 10 | 10 | 10 | 10 |
| Threonine | 119 | 709 | 691 | 560 | 596 | 651 | 641 | 657 |
| Serine | 105 | 281 | 264 | 147 | 156 | 180 | 199 | 185 |
| Asparagine | 132 | 130 | 124 | 75 | 78 | 109 | 119 | 119 |
| Glutamic Acid | 147 | 88 | 1 | 0 | 1 | 1 | 1 | 0 |
| Glutamine | 146 | 3525 | 3299 | 2517 | 2640 | 2906 | 2986 | 3082 |
| Proline | 115 | 145 | 165 | 163 | 174 | 177 | 157 | 171 |
| Glycine | 75 | 304 | 267 | 189 | 205 | 217 | 227 | 230 |
| Alanine | 89 | 190 | 340 | 341 | 384 | 423 | 333 | 330 |
| Valine | 117 | 678 | 635 | 485 | 500 | 532 | 551 | 561 |
| Cystine | 121 | 141 | 136 | 112 | 118 | 123 | 119 | 118 |
| Methionine | 149 | 157 | 133 | 91 | 99 | 107 | 108 | 107 |
| Isoleucine | 131 | 616 | 543 | 369 | 401 | 430 | 432 | 442 |
| Leucine | 131 | 649 | 554 | 364 | 400 | 430 | 438 | 444 |
| Tryosine | 181 | 413 | 398 | 328 | 355 | 379 | 373 | 386 |
| Phenylalanine | 165 | 336 | 316 | 244 | 268 | 291 | 287 | 292 |
| Tryptophan | 204 | 58 | 47 | 36 | 41 | 48 | 44 | 47 |
| Ammonia | 17 | 831 | 1182 | 956 | 1202 | 1219 | 931 | 990 |
| Ornthinine | | 42 | 97 | 74 | 115 | 112 | 56 | 44 |
| Lysine HCl | | 718 | 651 | 528 | 594 | 643 | 617 | 628 |
| Histidine | 155 | 284 | 310 | 223 | 243 | 262 | 266 | 265 |
| Arginine | 174 | 1058 | 948 | 826 | 901 | 978 | 974 | 1016 |

(b) Nutritional Stress Associated With Enhanced AAV Production

Follow-up studies were performed to confirm the importance of the relative paucity of glutamate and aspartate in the culture media. JL14 cells were taken from a spinner flask and divided into two sets. Each set was innoculated with $3 \times 10^9$ infectious units of 170–37 Ad5. One set of cells was resuspended at $10^6$ cells/mL in rAAV medium (Table 2) containing 10% FBS and 1% L-glutamine (300 mL). The other was resuspended in rAAV medium containing 10% FBS, 1% L-glutamine, 10 mg/L aspartatic acid, and 110 mg/L glutamic acid.

Each set was incubated at 37 degrees for 72 hours in a spinner flask. The cells were harvested, microflidized twice at 8000 psi, Benzonased, plated into an infectivity assay, harvested and probed.

Results showed that the control spinner flask produced 6.2 RUs per cell. The spinner flask supplemented with aspartic and glutamic acid produced 0.94 RUs per cell.

This indicates that when depletion of aspartic acid and glutamic acid is prevented by providing these amino acids in excess, rAAV production is compromised due to the failure to subject the cells to nutritional stress.

Further tests were performed using a HeLa-derived cell line D6 which has an integrated rAAV vector (ITR-(CMV promoter)-(β-gal reporter gene)-ITR), as well as copies of the wild-type AAV rep and cap genes.

The cells were seeded at $5 \times 10^6$ cells per T-225 flask in 30 mL complete DMEM (10% FBS, 2 mM L-Glutamine), and incubated at 37 degrees in 10% $CO_2$ for 2 days, whereupon the cells reached a density of $2 \times 10^7$ cells per flask. Cells in two duplicate flasks were infected with Ad 5 at an MOI of 10. One flask contained complete DMEM, the other contained complete DMEM supplemented with 5 x aspartic acid and glutamic acid. Cells were harvested and counted after 72 hours of culture.

The complete DMEM yielded $2.6 \times 10^7$ cells with 88% viability. The aspartate/glutamate supplemented medium yielded $3.8 \times 10^7$ cells with 91% viability. Cells were resuspended, sonicated, treated with Benzonase (25 U/ML), clarified, and assayed by slot blot analysis.

Results were as follows: D6 virus was produced in complete (unsupplemented) DMEM at $1.8 \times 10^{10}$ DRP/mL (1800 DRP per cell). D6 virus was produced in aspartate/glutatmate supplemented DMEM at $1.4 \times 10^9$ DRP/mL (140 DRP/cell).

Example 10
Recombinant AAV Vector Production Under Serum Stress

As an example of rAAV production under stress conditions, we have used reduced-serum stress in conjunction with techniques as described above. Briefly, JL14 cells were grown in spinner flasks in modified DMEM+10% FBS in continuous serial culture mode, and were split every 3–4 days. Cells from suspension culture were placed into 16 Nunc Cell Factories, 10-stack, at $3 \times 10^8$ cells/factory on a three- to four-day rotation. The medium used for growth had a ten-fold reduction in serum (i.e. DMEM+1% FBS) thereby placing the cells under serum stress.

At 24 hours after seeding, the medium in the factories was removed and fresh medium containing $3 \times 10^9$ Ad units/ml was added. After 72 hours of culture at 37 degrees, the cells were dislodged from the factories by gentle tapping, medium containing cells was collected and the cells were pelleted and resuspended in TMEG+100 mM NaCl, and then lysed by passage through a microfluidizer at 8000 psi. The lysate was clarified through a 5 micron filter and the clarified lysate was loaded on a 500 ml PI anion exhange column. The column was eluted with a gradient of increasing NaCl (up to 500 mM) in TMEG buffer. Fractions were collected and assayed using a Clone 37 assay as described by Allen et al. (WO96/17947, supra). The fractions containing most of the AAV vector were then pooled and concentrated 10-fold using a Centriprep centrifugal concentrator at 1000 x g for 30 minutes. The concentrated material was dialyzed against Ringer's Balanced Salt Solution with 5% glycerol, and stored at –70 degrees C. The AAV was assayed by the Clone 37 assay, as well as by slot blot and SDS-PAGE. The material may also be assayed for the presence of adenovirus, adenoviral proteins, and cellular DNA, as well as other potential contaminants.

FIG. 11 shows the results obtained using GAK-0003 producer cells set up in T-225 flasks at $10^7$ cells per flask, and innoculated on Day 2 with DAB-003 adenovirus at an MOI of 10. Different flasks were cultured for 72 hours at 37 degrees in fresh DMEM containing a different percentage of FBS, as shown in the figure. On Day 5, each flask was harvested, the cells were counted, resuspended, sonicated, Benzonased, and plated to measure vector production as before.

Optimal vector producton was observed at a FBS percentage of 1%. Accordingly, medium that is deficient in FBS (less than 2.5%, preferably less than 2% but more than 0%) is preferred as a condition for subjecting the producer cells to serum stress.

Example 11

Recombinant AAV Vector Production Under pH Stress

As a further example of rAAV production under stress conditions, we have used pH stress in conjunction with techniques as described above. Briefly, AAV producer cells were grown in bioreactors as described above. Cells were then infected with Ad5 at MOI=10 and inoculated into low-serum media (as in Example 11) in suspension in 1.5 liter bioreactors. Cultures were maintained at various elevated pH levels (from 7.2 to 8.0). Cultures were then monitored daily for cell number, viability, glucose consumption, lactate production, pH, osmolarity and AAV production. As shown below, there was an increase in AAV production when the pH was elevated to 7.4; coupled with an even more dramatic increase in the number of AAV particles released into the supernatant (which increased as pH was elevated):

| Culture pH | Cell-associated Particles | Supernatant Particles | Total Particles | % Cell-associated | % in Supernatant |
|---|---|---|---|---|---|
| 7.2 | 4.70E + 12 | 1.90E + 09 | 4.70E + 12 | 100% | 0% |
| 7.4 | 6.50E + 12 | 1.30E + 13 | 1.95E + 13 | 33% | 67% |
| 7.6 | 3.40E + 12 | 1.50E + 13 | 1.84E + 13 | 18% | 82% |
| 8.0 | 1.30E + 12 | 1.50E + 13 | 1.63E + 13 | 8% | 92% |

In sum, as pH was raised, we observed a sharp increase in the number of AAV particles released into the supernatant, and a shift in the percentage of supernatant:cell-associated particles (from nearly all cell-associated at pH 7.2 to mostly supernatant (92%) at pH 8.0). The ability to recover AAV particles directly from the supernatant without the need for lysing the producer cells represents a powerful advantage in terms of AAV production and purification. AAV isolated from the supernatant using pH stress can be readily concentrated and purified using techniques as described herein (e.g. ion-exchange chromatography and/or tangential-flow filtration).

Example 12

General Methods for Additional rAAV Release Experiments

Quantitation of rAAV titers in vector preparations: slot blot assay

The rAAV DNA slot blot assay was conducted as follows. Aliquots of samples were digested with nuclease to remove unencapsidated DNA. The samples were then denatured in 0.4M NaOH, 10 mM EDTA with 1.0 µg/ml salmon sperm DNA at 65° C. Samples and rAAV standards were diluted and filtered onto nylon membranes using a slot blot manifold and washed with 0.4M NaOH. The filter was hybridized with a $^{32}$P-labeled human CFTR cDNA restriction fragment. This probe detects an approximately 1.5 kb fragment from the AAVCF vector (corresponding to the predicted 1.488 kb EcoRI fragment).

Microtiter infectivity assay to measure rAAV

The microtiter infectivity assay was conducted as previously described. Atkinson et al. (1998) *Nucleic Acids Research* 26(11): 2821–2823. Briefly, a high-throughput microtiter infectivity assay to measure infectious virus was conducted as follows. Aliquots (10 µl) of serially diluted cell-free supernatants were inoculated onto HeLa clone 37 cells grown in 96-well microtiter plates. After three days, infected cells were treated and lysed with a denaturation solution (addition of ¹⁄₁₀th volume of 4.0 M NaOH, 10 µg/ml salmon sperm DNA and 100 mM EDTA). Lysate was transferred to a Silent Monitor BiodyneB plate (Pall) and vacuum filtered onto the nylon membrane. The membrane was washed, denatured, hybridized with a $^{32}$P-labeled human CFTR cDNA restriction fragment. This probe detects an approximately 1.5 kb fragment from the AAVCF vector (corresponding to the predicted 1.488 kb EcoRI fragment). Vector replication was quantitated relative to an endogenous genomic CFTR band and is expressed as replication units. One replication unit (RU) is defined as a signal intensity equivalent to that of the endogenous genomic CFTR band which is approximately 1.8 kb. Linear regression of serially diluted known vector standards was used to extrapolate and calculate vector concentration in samples.

Production media

Tables 5 and 6 provide concentrations of components (in mg/l) of media suitable for growing cells and producing rAAV (blanks indicate zero concentration). Generally, it is preferable to have reduced serum levels. For example, the media used in these experiments contained about 1% fetal bovine serum (FBS).

TABLE 5

|  | Concentration |
|---|---|
| INORGANIC SALTS | |
| CaCl2 anhydrous | 200 |
| Fe(NO3)3*9H2O | 0.1 |
| KCL | 400 |
| MgSO4*7H2O | 200 |
| NaCl | 4675 |
| NaHCO3 | 1200 |
| NaH2PO4.H2O | 125 |
| OTHER COMPONENTS | |
| Glucose | 8500 |
| HEPES | 3575 |
| Phenol Red, Na Salt | |
| sodium pyruvate | 110 |
| calcium pantothenate | 6 |
| choline chloride | 6 |
| folic acid | 6 |
| inositol | 11 |
| nicotinamide | 6 |
| pyridoxal HCl | 2 |
| pyridoxine HCl | 4 |
| riboflavin | 0.6 |
| thiamine HCl | 6 |
| F-68 | 500 |
| AMINO ACIDS | |
| L-Alanine | 8.9 |
| L-Arginine.HCL | 236.9 |
| L-Asparagine.H2O | 17 |
| L-Aspartic acid | 13.3 |
| L-Cystine | 72 |
| L-Glutamic acid | 14.7 |
| L-Glutamine | 1168 |
| Glycine | 37.5 |
| L-Histidine.HCL.H2O | 84 |
| L-Isoleucine | 157.3 |
| L-Leucine | 157.2 |
| L-Lysine.HCL | 218.7 |
| L-Methionine | 45.1 |
| L-Phenylalanine | 99 |
| L-Proline | 11.5 |
| L-Serine | 52.5 |
| L-Threonine | 142.8 |
| L-Tryptophan | 26.2 |
| L-Tyrosine | 108 |
| L-Valine | 140.4 |

TABLE 6

| Component | Concentration, mg./L |
|---|---|
| CaCl2 | 200 |
| Fe(NO3)3.9H2O | 0.1 |
| KCl | 400 |
| MgSO4.7H2O | 200 |
| NaCl | 4675 |
| NaHCO3 | 1200 |
| NaH2PO4.H2O | 125 |
| glucose | 4500 |
| HEPES | 3575 |
| sodium pyruvate | 110 |
| calcium pantothenate | 4 |
| choline chloride | 4 |
| folic acid | 4 |
| inositol | 7 |
| nicotinamide | 4 |
| pyridoxal HCl | |
| pyridoxine HCl | 4 |
| riboflavin | 0.4 |
| thiamine HCl | 4 |
| F68 | 500 |
| L-alanine | |
| L-arginine HCl | 84 |
| L-asparagine | |
| L-aspartic acid | |
| L cysteine | 48 |
| Lglutamic | |
| Lglutamine | 876 |
| glycine | 30 |
| l-histidine-HCl.H2O | 42 |
| Lisoleucine | 104.8 |
| L-Leucine | 104.8 |
| L-Lysine HCl | 146.2 |
| L-methionine | 30 |
| L-phenylalanine | 66 |
| L-proline | |
| L-serine | 42 |
| L-threonine | 95.2 |
| L-tryptophan | 16 |
| Ltyrosine | 72 |
| Lvaline | 93.6 |

Example 13

Effect on pH on rAAV Vector Particle Production in Producer Cell Lysates

JL14 cells were inoculated at about $3 \times 10^5$ cells/ml in a 3 liter bioreactor and grown in 1.5 liters of the rAAV medium shown in Table 5. Two days after inoculating the culture medium in the bioreactor with JL14 cells, the bioreactor was perfused with fresh medium, beginning at 0.4 volumes per day, then doubling this amount every 24 hours thereafter. After 5 days, or when the cell density reached $6 \times 10^6$ cells/ml, $3 \times 10^8$ cells were removed and grown under standard conditions, i.e, allowing the pH to vary. The cells remaining in the Bioreactor were concentrated in a volume of 750 ml culture medium, and a three volume medium exchange was performed with production medium (i.e., medium as in Table 2) at pH 7.2 to exchange the medium, so that the final volume of cell culture was 750 ml. Adenovirus type 5 was grown from a stock obtained from the American Type Culture Collection (Manassas, Va.). Adenovirus was diluted into 750 ml production medium and added to the cells (multiplicity of infection (MOI)=10), bringing the final volume to 1.5 liters. Infection with adenovirus was allowed to proceed for one hour at 37° C.

After allowing infection to proceed, $1 \times 10^5$ cells were transferred to each of 5 separate spinner flasks. The volume in the five flasks was brought up to 1.5 liters with production medium at pH 6.6, 7.0, 7.2, 7.4, and 7.8, respectively. The contents of the spinner flasks were transferred to separate bioreactors, which were then maintained individually at pH 6.6, 7.0, 7.2, 7.4, and 7.8. Other culture medium parameters were as follows: temperature =37° C.; dissolved oxygen concentration ($DO_2$)=30%; and agitation =150 rpm. Temperature, pH, $DO_2$, cell density, osmolarity and glucose/lactate were monitored daily. Cell samples were harvested on day 2 and day 3 post-infection and lysed. The cell lysates were assayed by DNAse-resistant particles (DRP) slot blot assay and by the microtiter infectivity assay.

Figure 14A:
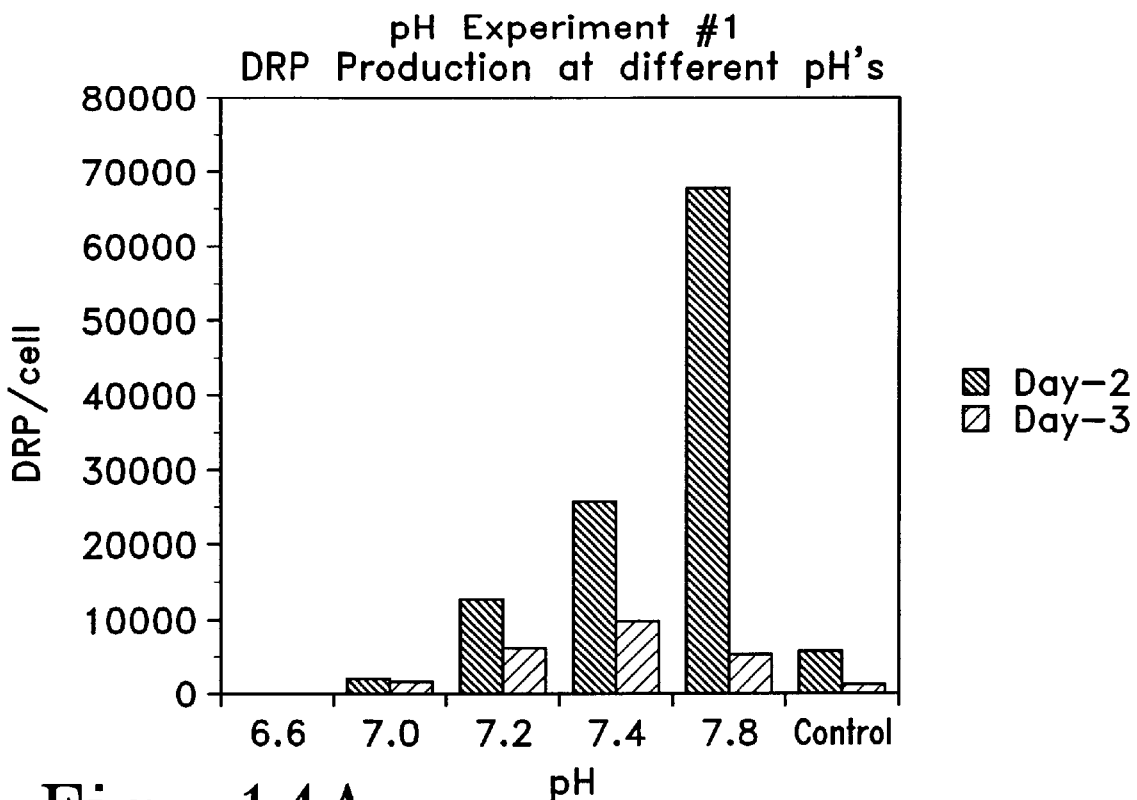
FIGS. 14A and 14B are bar graphs depicting the results of two separate experiments, expressed as DNase resistant particles (DRP) per cell at the various pH levels. Cell cultures were maintained at the indicated pH levels, and cell lysates were assayed at day 2 (solid bars) and day 3 (hatched bars) post-infection.
Figure 14B:
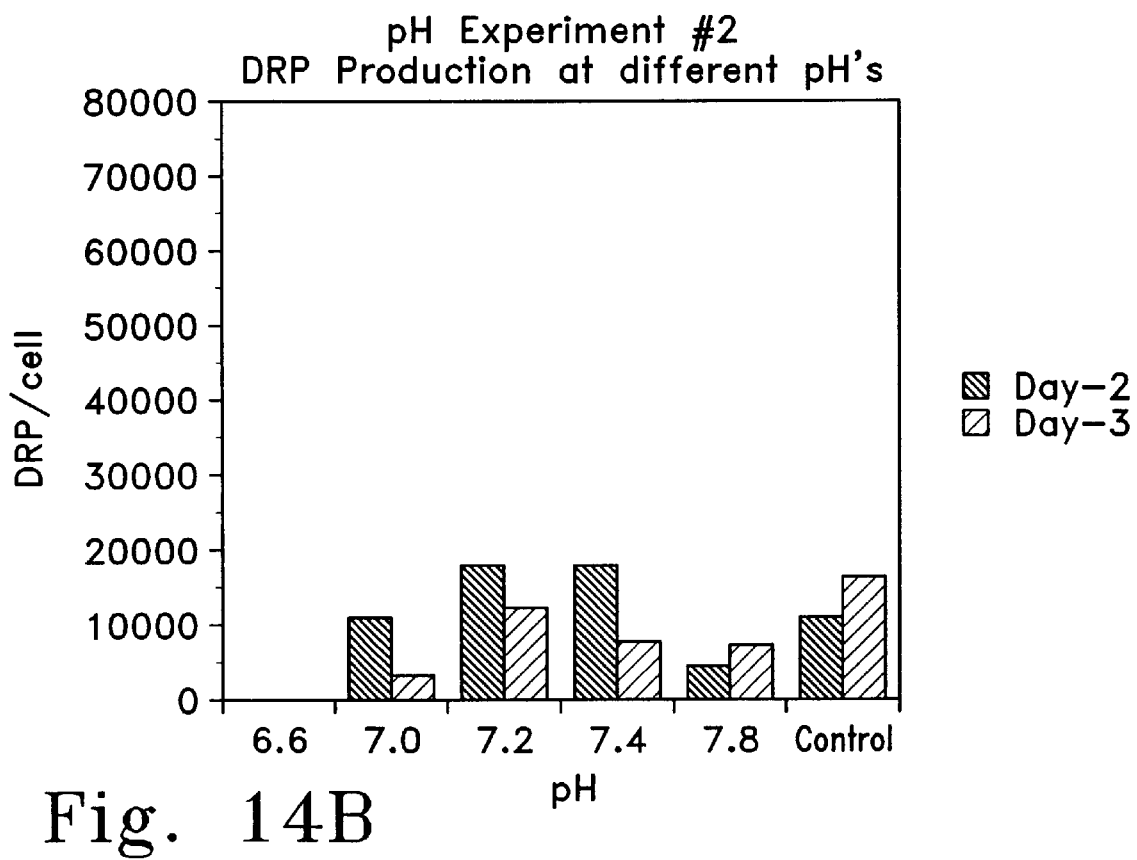

FIGS. 14A and 14B are bar graphs depicting the results of two separate experiments, expressed as DRP per cell at the various pH levels. Solid bars represent DRP/cell at day 2 post-infection; hatched bars represent the DRP/cell at day 3. The DRP/cell in the cultures maintained at pH 7.2, pH 7.4, and pH 7.8 decreased dramatically from day 2 to day 3 post-infection, while this reduction was not as pronounced in the control cell culture. The total cell density did not change appreciably under these culture conditions.

Example 14

Effect on pH Release of rAAV Vector Particles into the Cell Culture Medium

To further investigate the effects of pH on rAAV vector production, JL14 cells were grown in a perfusion bioreactor as described above (using media described in Table 5) to a density of $10^7$ cells/ml. The cell culture was concentrated to a volume of 750 ml and the medium exchanged by performing 3 diavolumes. The total volume was brought to 1.5 liters with production medium containing adenovirus at a MOI of 10. Infection was allowed to proceed for one hour.

After allowing infection to proceed, $1 \times 10^5$ cells were transferred to each of 5 separate spinner flasks. The volume in the five flasks was brought up to 1.5 liters with production medium at pH 7.2, 7.4, 7.6, 7.8, 8.0, and control flasks (pH not maintained at the starting level). The contents of the spinner flasks were transferred to separate bioreactors, which were then maintained individually at pH 7.2, 7.4, 7.6, 7.8, 8.0. Bioreactors maintained the pH at the stated level ±0.05 pH units. Other culture medium parameters were as follows: temperature =37° C.; dissolved oxygen concentration ($DO_2$)=30%; and agitation =150 rpm. Cells and culture supernatants (culture media) were harvested on days 2 and 3.

Figure 15A:
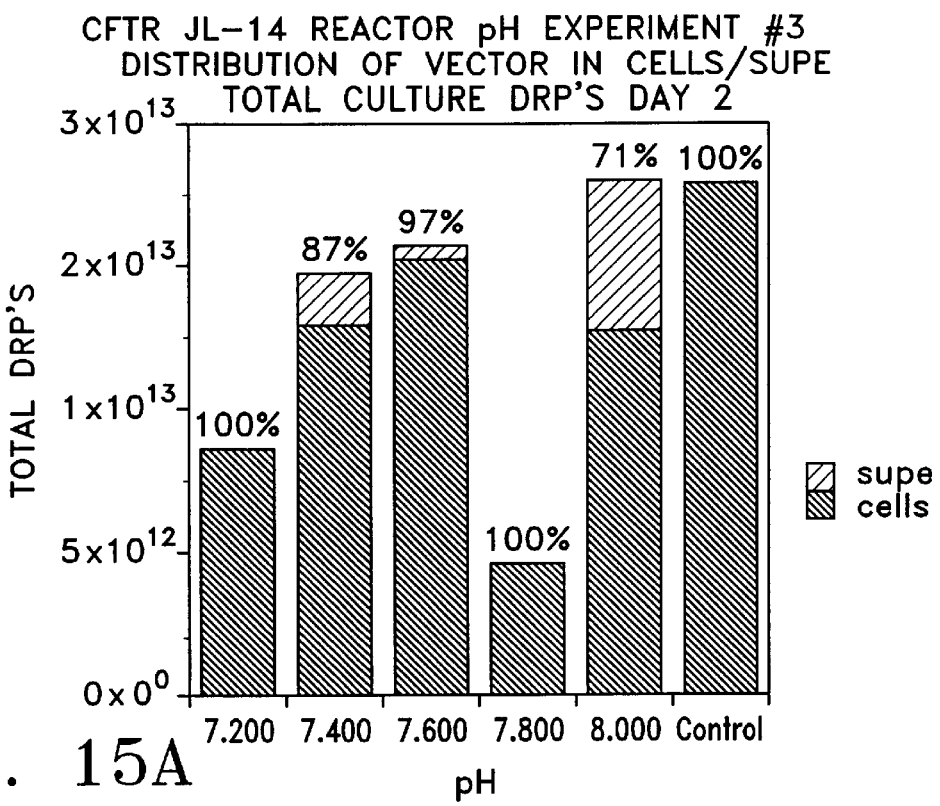
FIGS. 15A and 15B are bar graphs and depict the results, expressed as total DRPs, of rAAV production, at day 2 (FIG. 15A) and day 3 (FIG. 15B) post-infection, in bioreactors maintained at various pH levels. Percentages above each bar are percentages of total DRPs in the cell lysate. The solid portion of each bar represents DRPs in cell lysates, while the hatched portion of each bar represents the DRPs in the cell culture medium. Percentages above each bar indicate the percentage of total DRPs in the cell lysate.
Figure 15B:
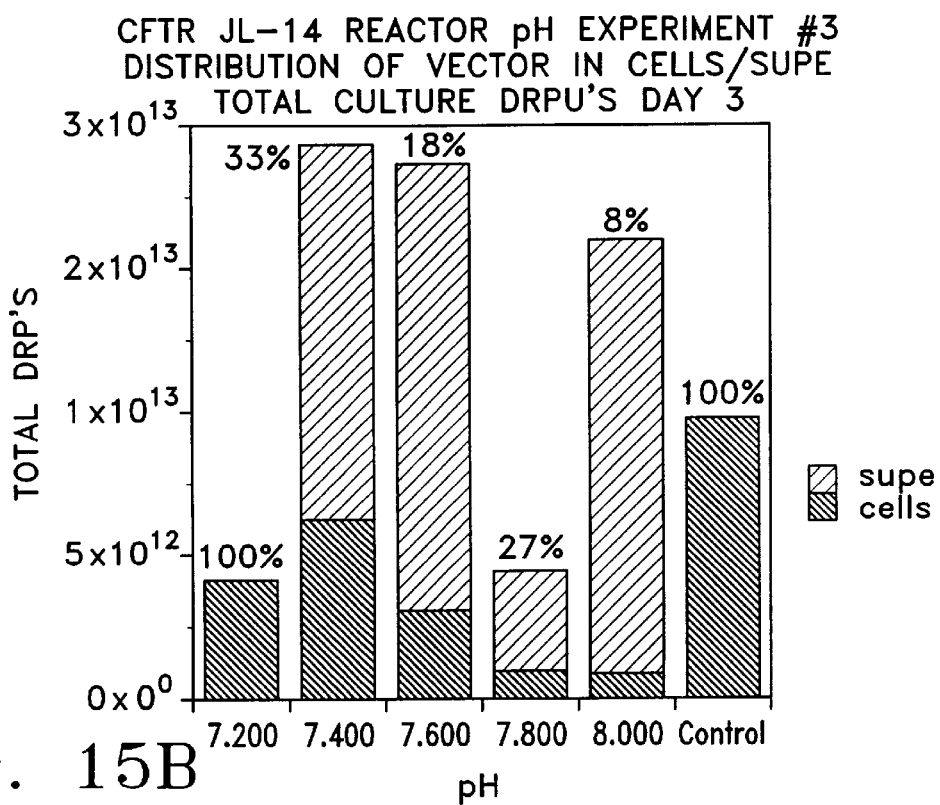

The results are shown in FIGS. 15A and 15B. FIGS. 15A and 15B are bar graphs and depict the results, expressed as total DRPs, of rAAV production in bioreactors maintained at various pH levels. Percentages above each bar are percentages of total DRPs in the cell lysate. The solid portion of each bar represents DRPs in cell lysates, while the hatched portion of each bar represents the DRPs in the cell culture medium. On day 2 post-infection, 29% of the total DRPs were in the culture medium of the culture maintained at pH 8.0, while on day 3, post-infection, the percent of total DRPs in the culture medium rose to 92%. On day 3 post-infection, the percentage of total DRPs in the culture medium was 67% at pH 7.4, 82% at pH 7.6, 73% at pH 7.8 and 92% at pH 8.0. Cultures maintained at pH 7.2 did not yield any DRPs in the cell culture medium in this experiment.

Figure 16A:
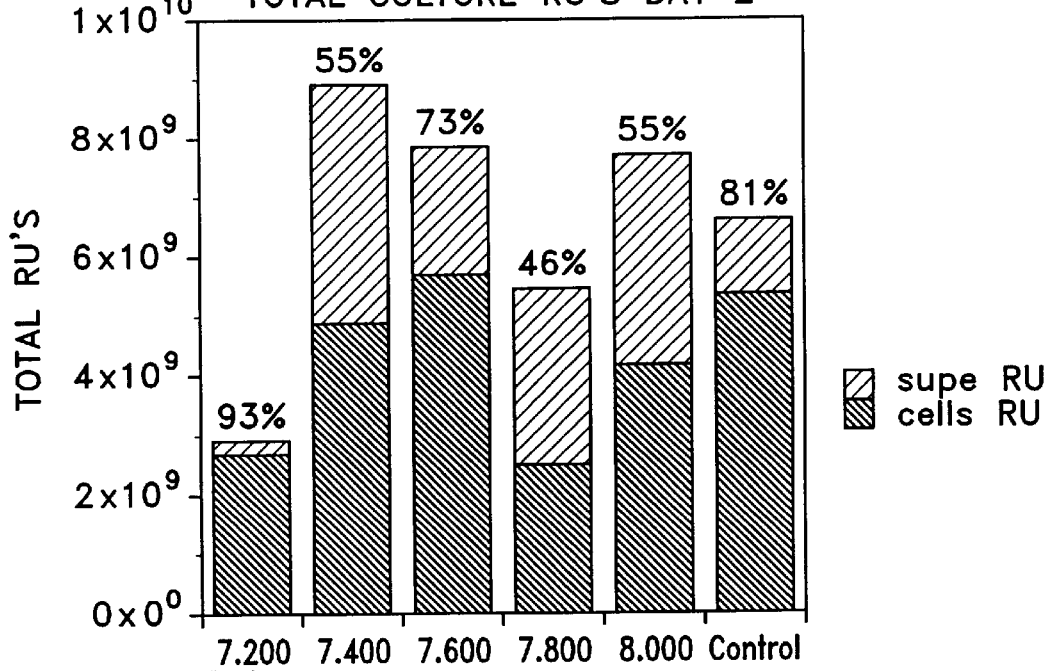
FIGS. 16A and 16B are bar graphs depicting the total replication units (RU), at day 2 (FIG. 16A) and day 3 (FIG. 16B) post-infection, in the culture media (hatched portion of each bar) and cell lysates (solid portion of each bar) when cultures were maintained at the indicated pH levels. Percentages above each bar indicate the percentage of total RUs in the cell lysate.
Figure 16B:
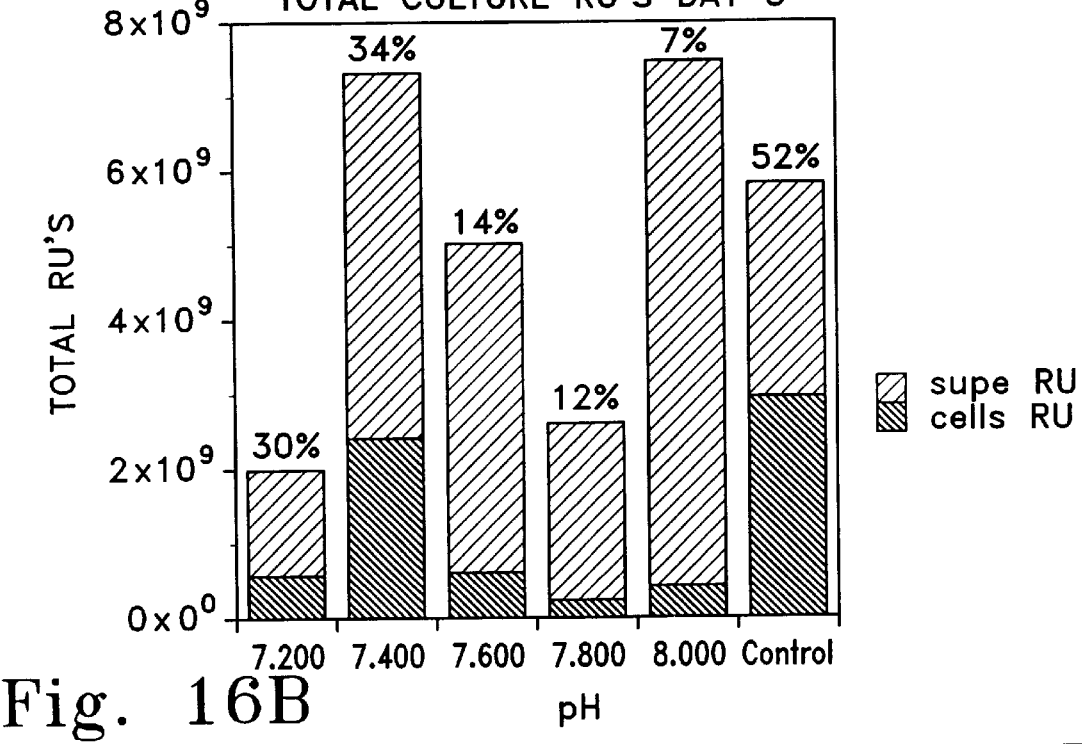

The day 2 and day 3 post-infection cell lysates and culture media from the bioreactors maintained at pH 7.2, 7.4, 7.6, 7.8, and 8.0 were assayed for replication units (RU) using an infectivity assay. The data are shown in FIGS. 16A and 16B. The total cell density did not change appreciably under these culture conditions.

FIGS. 16A and 16B are bar graphs depicting the total replication units (RU) assayed at day 2 (FIG. 16A) and day 3 (FIG. 16B) post-infection in the culture media (hatched portion of each bar) and cell lysates (solid portion of each bar) when cultures were maintained at the indicated pH levels. Percentages above each bar indicate the percentage of total RUs in the cell lysate. These data demonstrate that the rAAV particles released into the cell culture medium are functional in an infectivity assay.

Figure 17:
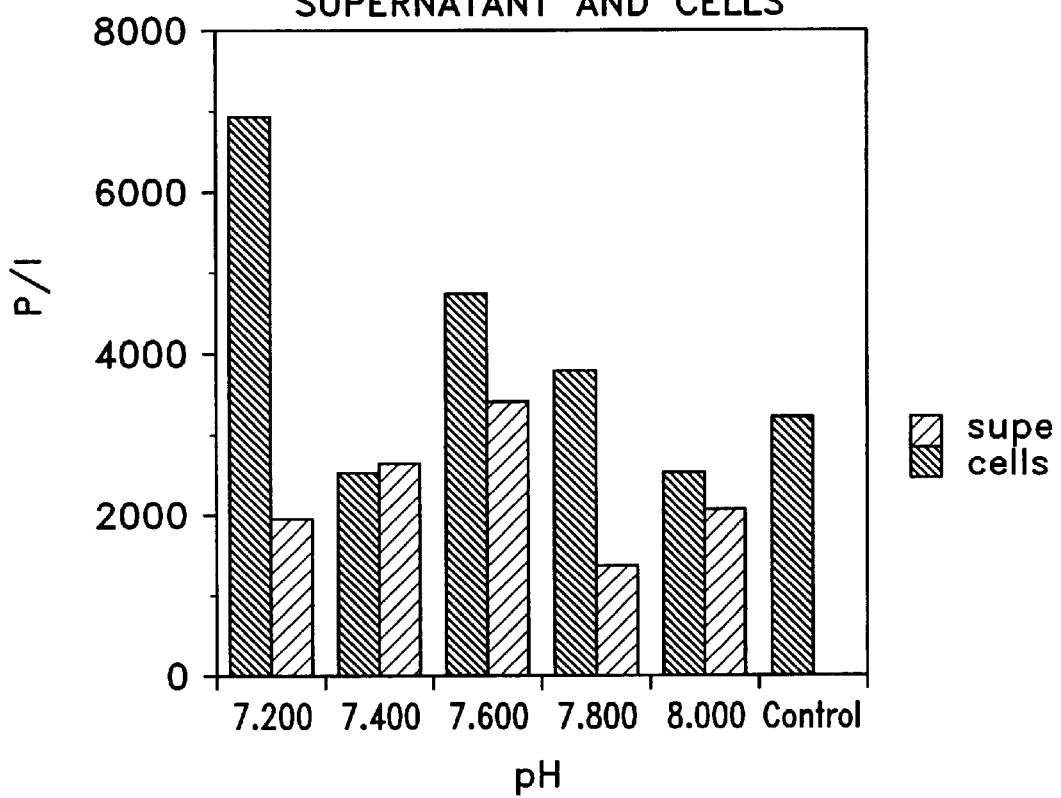
FIG. 17 is a bar graph depicting the particle:infectivity (P/I) ratio of rAAV particles harvested from cell lysates (solid portion of each bar) and cell culture medium (hatched portion of each bar) at day 3 post-infection from bioreactors maintained at the indicated pH levels.

FIG. 17 is a bar graph depicting the particle:infectivity (P/I) ratio of rAAV particles harvested from cell lysates (solid portion of each bar) and cell culture medium (hatched portion of each bar) at day 3 post-infection from bioreactors maintained at the indicated pH levels. These date indicate that the majority of the rAAV vector released into the cell culture medium is infectious.

Example 15

Effect of Osmolality on Release of rAAV Vector Particles into the Cell Culture Medium To assess the effects on release of rAAV into the cell culture medium of starting osmolality of the culture medium, JL14 cells were grown in bioreactors and infected with adenovirus essentially as described in Example 14. The starting osmolality in the individual bioreactors was 130, 200, 300, 400, and 500 mOsm (using NaCl), respectively. In each reactor, the pH was maintained at pH 8.0 (±0.05); temperature =37° C.; $DO_2$=30%; and agitation =150 rpm. On days 2, 3, and 4 post-infection, cell lysates and cell culture media were collected and analyzed for rAAV vector production.

Figure 19A:
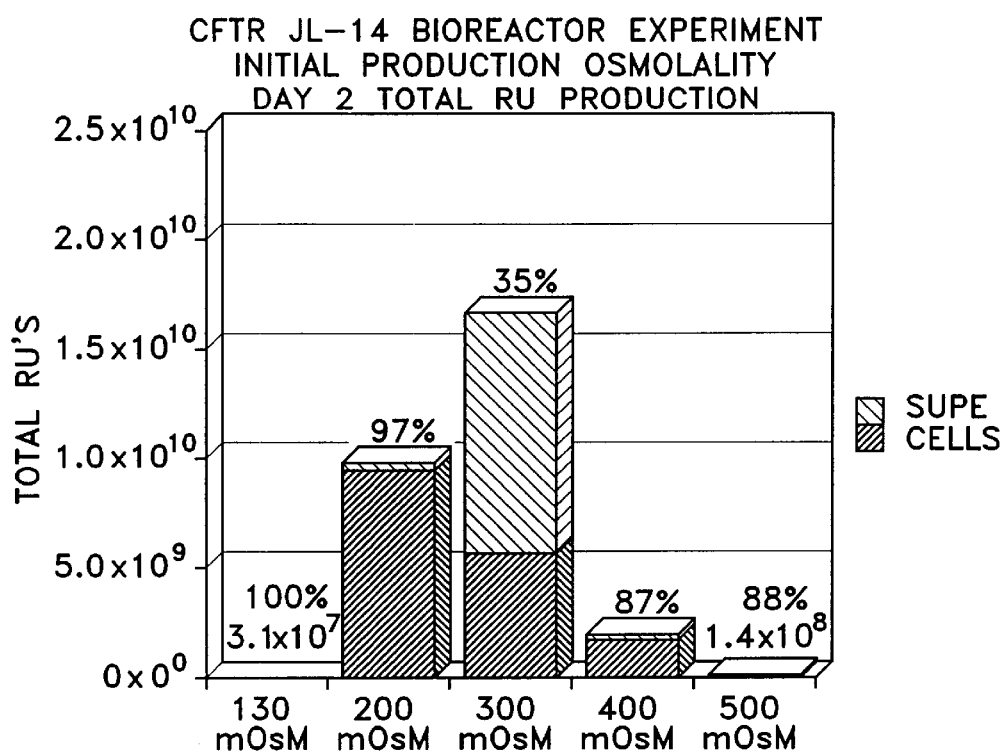
FIGS. 19A, 19B, and 19C are bar graphs depicting the total RUs in cell lysates (solid portion of each bar) and cell culture media (hatched portion of each bar) on day 2 (FIG. 19A), day 3 (FIG. 19B), and day 4 (FIG. 19C) post-infection in bioreactors in which the cell culture media contained the indicated starting osmolality. Percentages above each bar indicate the percentage of total RUs in the cell lysates.
Figure 19B:
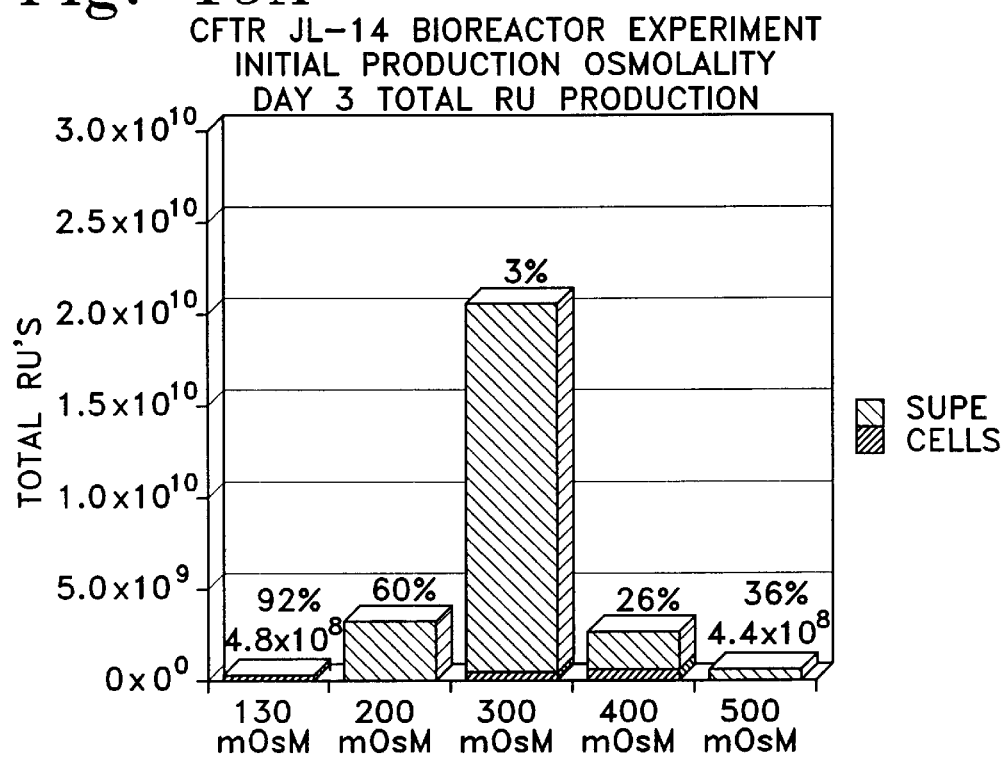
Figure 19C:
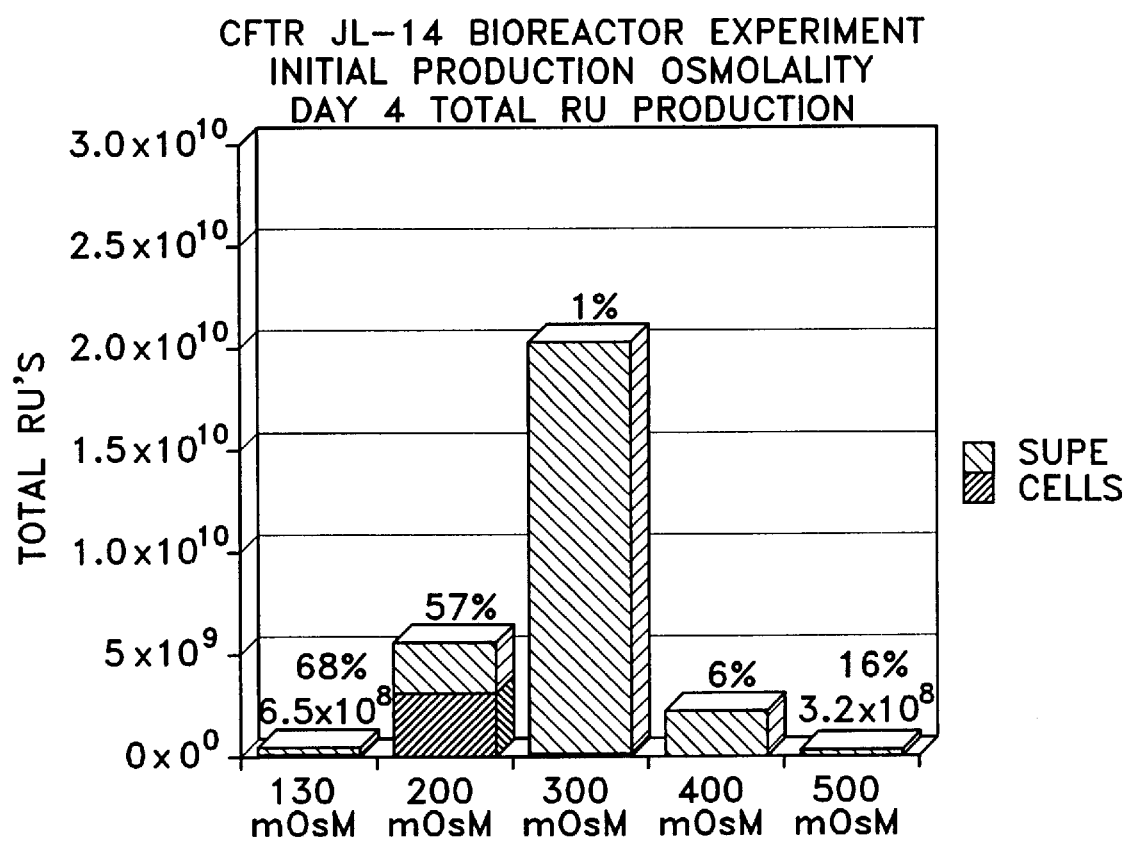
Figure 20:
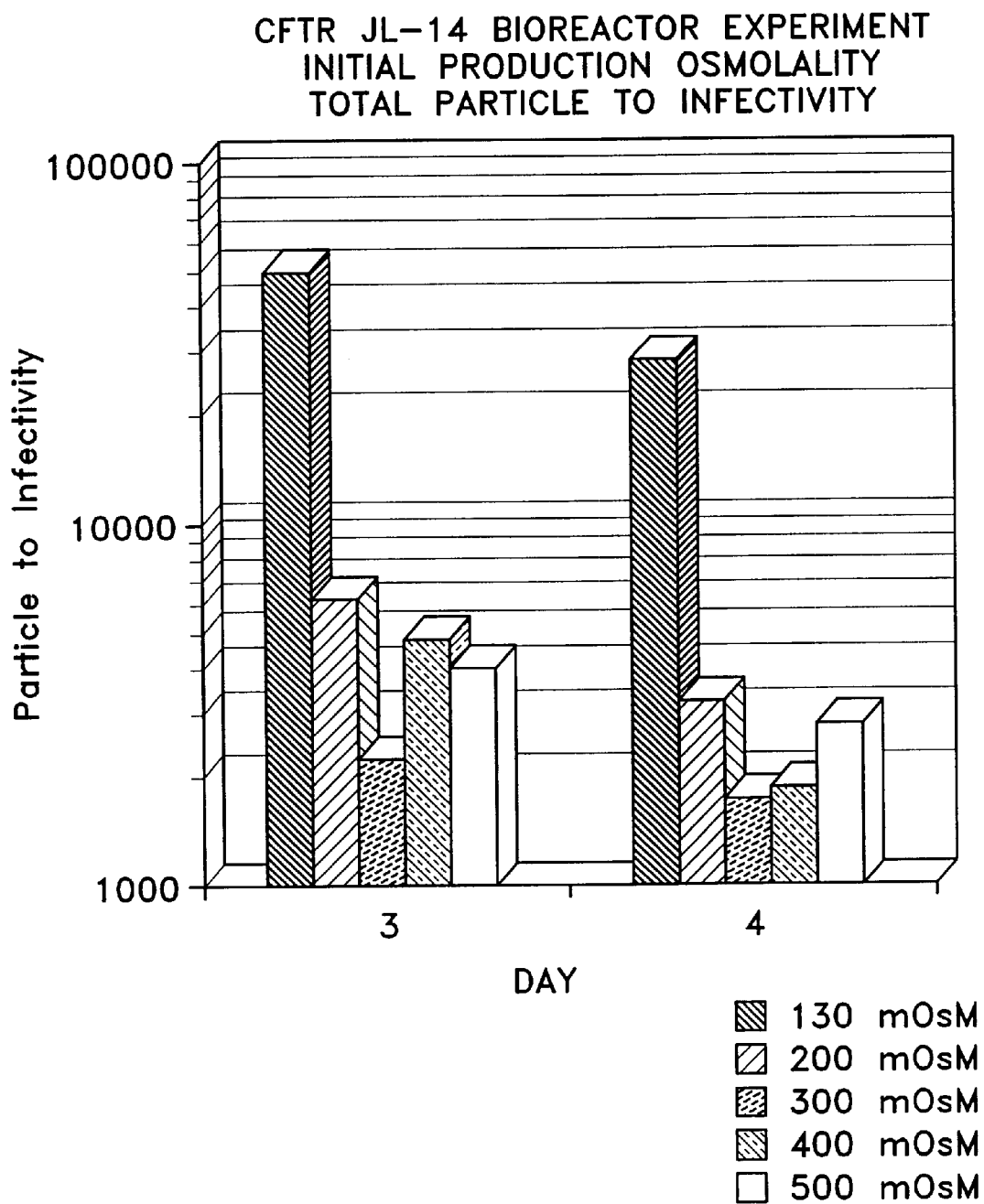
FIG. 20 is a bar graph depicting the P/I ratio of rAAV particles in cell culture media at days 3 and 4 from bioreactor cultures with the indicated starting osmolalities.

The results are shown in FIGS. 18–20.

Figure 18A:
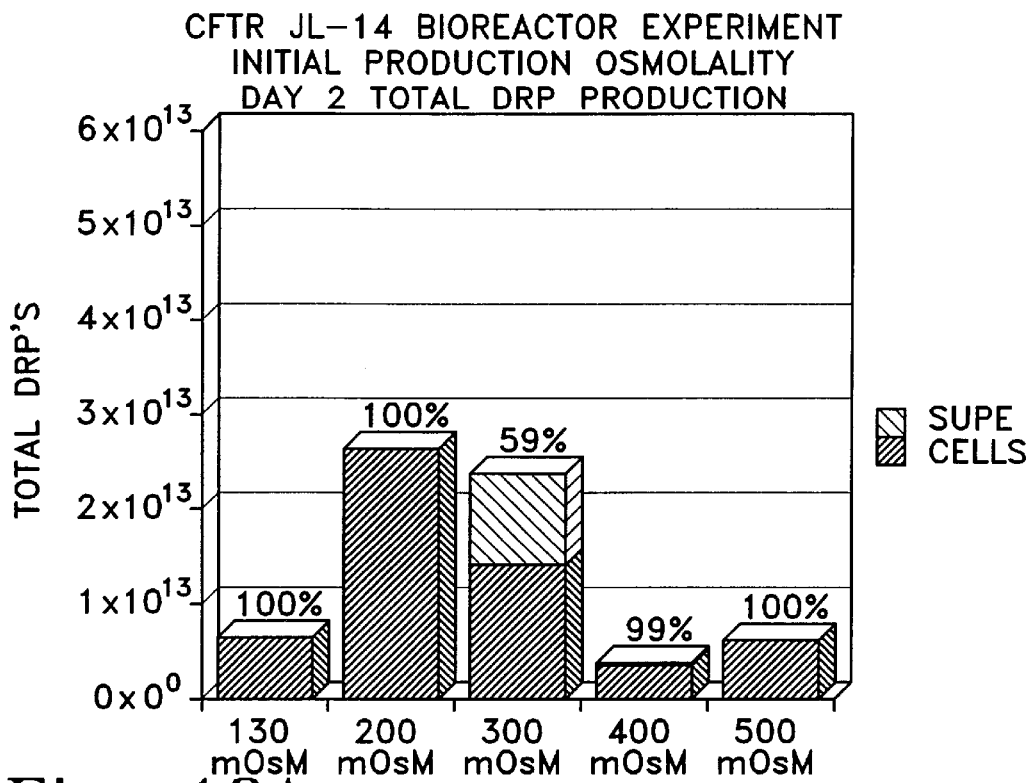
FIGS. 18A, 18B, and 18C are bar graphs depicting the total DRPs in cell lysates (solid portion of each bar) and cell culture media (hatched portion of each bar) on day 2 (FIG. 18A), day 3 (FIG. 18B), and day 4 (FIG. 18C) post-infection in bioreactors in which the cell culture media contained the indicated starting osmolality. Percentages above each bar indicate the percentage of total DRPs in the cell lysate.
Figure 18B:
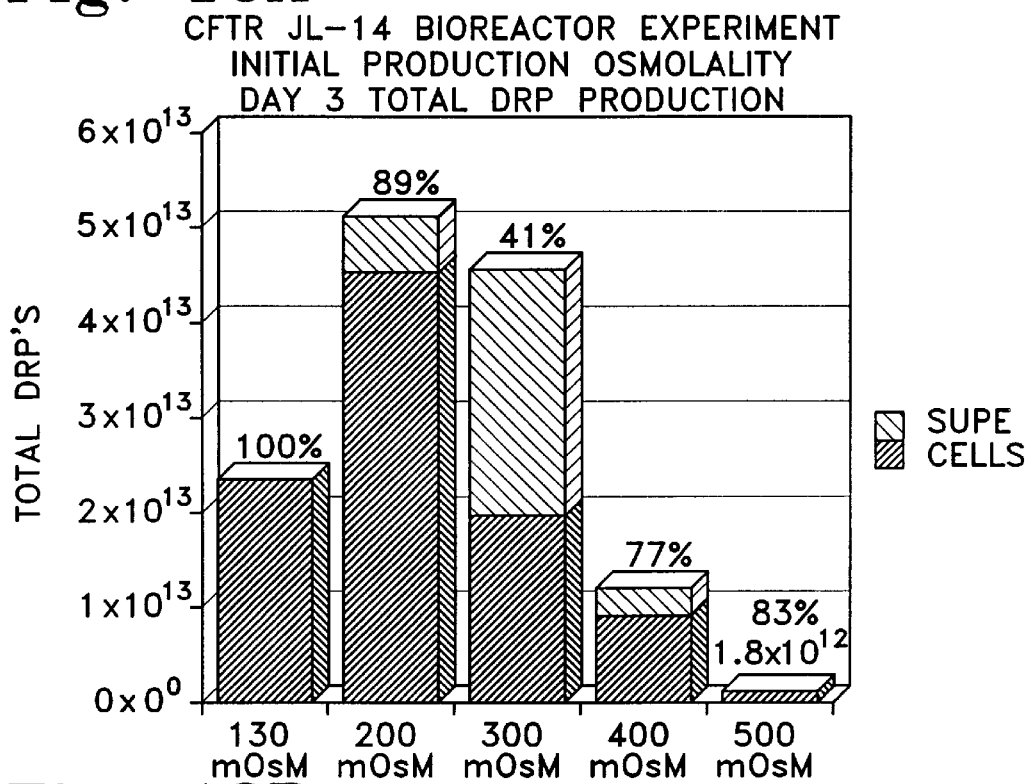
Figure 18C:
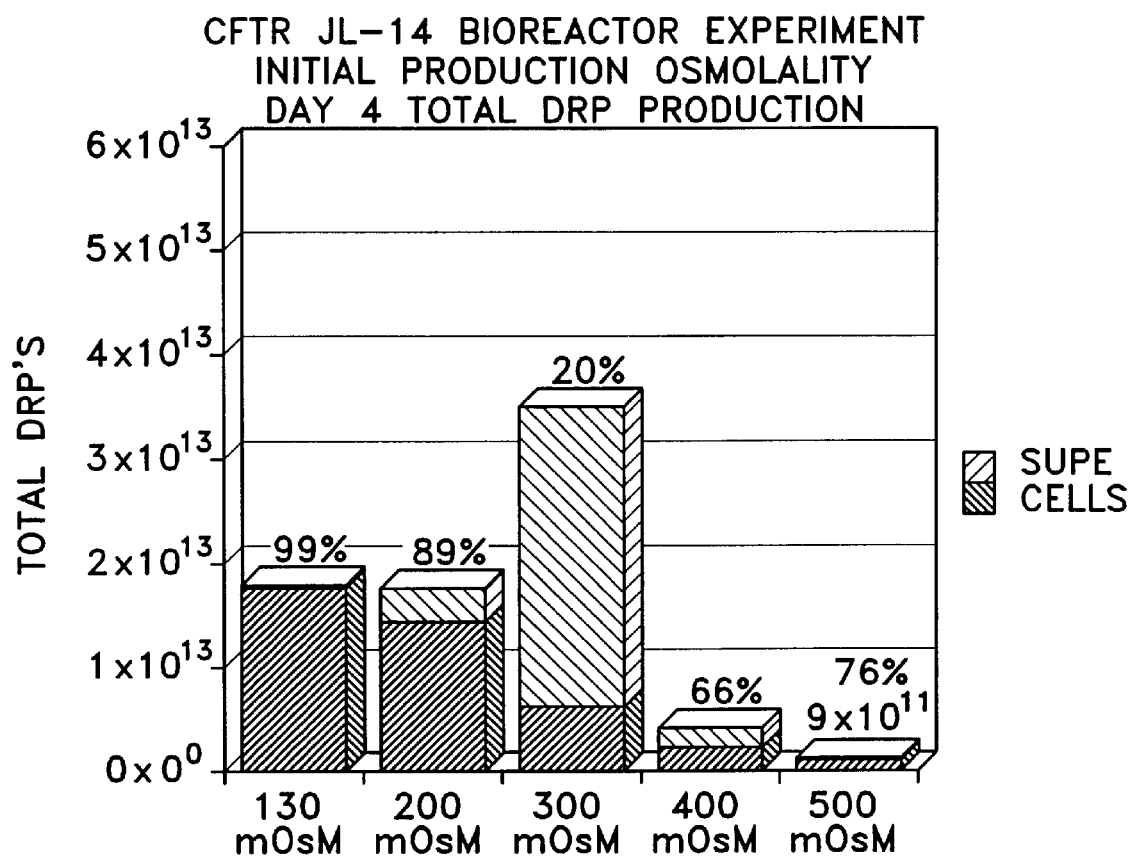

FIGS. 18A, 18B, and 18 C are bar graphs depicting the total DRPs in cell lysates (solid portion of each bar) and cell culture media (hatched portion of each bar) on day 2 (FIG. 18A), day 3 (FIG. 18B), and day 4 (FIG. 18C) post-infection in bioreactors in which the cell culture media contained the indicated starting osmolality. Percentages above each bar indicate the percentage of total DRPs in the cell lysate. These data show that when the cell culture medium has a starting osmolality of 300 mOsm, 41%, 59%, and 80% of the total DRPs are in the cell culture medium at day 2, 3, and 4 respectively. A starting cell culture medium osmolality of 300 mOsm gave the maximum percentage of total rAAV vector in the cell culture medium, compared with other starting osmolalities tested. The total cell density did not change appreciably under these culture conditions.

FIGS. 19A, 19B, and 19C are bar graphs depicting the total RUs in cell lysates (solid portion of each bar) and cell culture media (hatched portion of each bar) on day 2 (FIG. 19A), day 3 (FIG. 19B), and day 4 (FIG. 19C) post-infection in bioreactors in which the cell culture media contained the indicated starting osmolality. Percentages above each bar indicate the percentage of total RUs in the cell lysates. These data indicate that the rAAV vector released into the medium is infectious.

FIG. 20 is a bar graph depicting the P/I ratio of rAAV particles in cell culture media at days 3 and 4 from bioreactor cultures with the indicated starting osmolalities.

Example 16

Effect of Temperature on Release of rAAV Vector Particles into the Cell Culture Medium JL14 cells were grown in bioreactors and infected with adenovirus essentially as described in Example 2. Cells were transferred to bioreactors maintained individually at 31° C., 34° C., 37° C., 39° C., and 42° C., respectively. These temperatures were maintained ±0.5 ° C. The pH in each reactor was maintained at 8.0 (±0.05); agitation =150 rpm; DO2=30%. On days 2, 3, and 4 post-infection, cell lysates and cell culture media was analyzed for rAAV particles.

The results are shown in FIGS. 21 and 22.

Figure 21A:
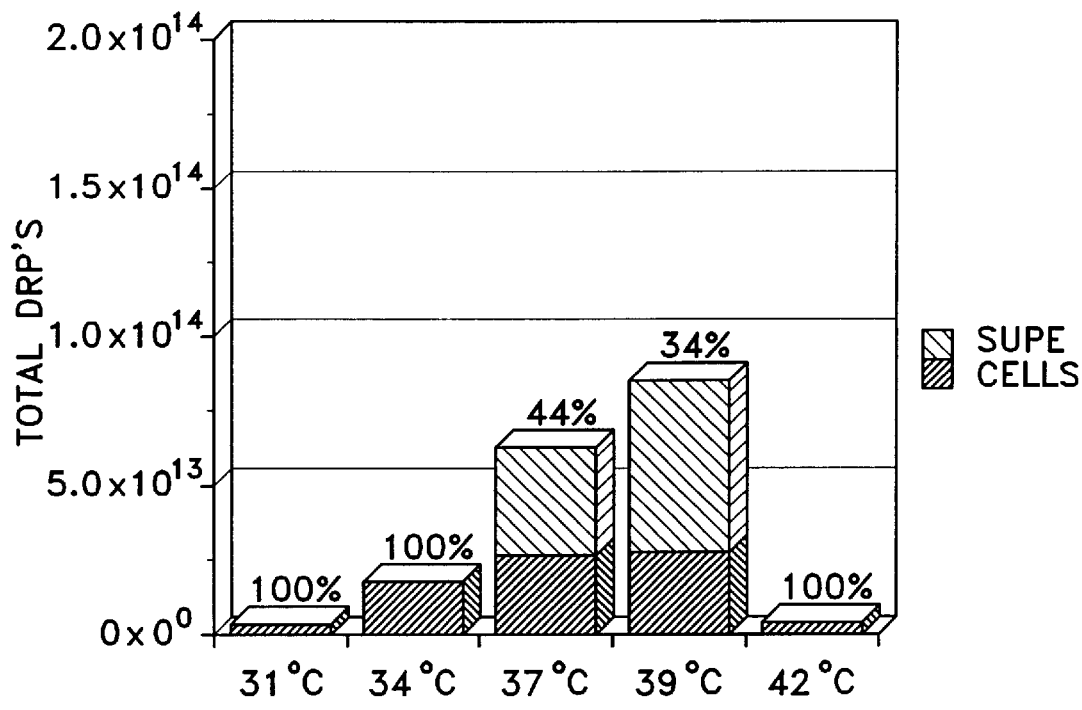
FIGS. 21A–C are bar graphs depicting the total DRPs in cell lysates (solid portion of each bar) and cell culture media (hatched portion of each bar) on day 2 (FIG. 21A), day 3 (FIG. 21B), and day 4 (FIG. 21C) post-infection in bioreactors in which the cell culture media was maintained at the indicated temperature. Percentages above each bar indicate the percentage of total DRPs in the cell lysate.
Figure 21B:
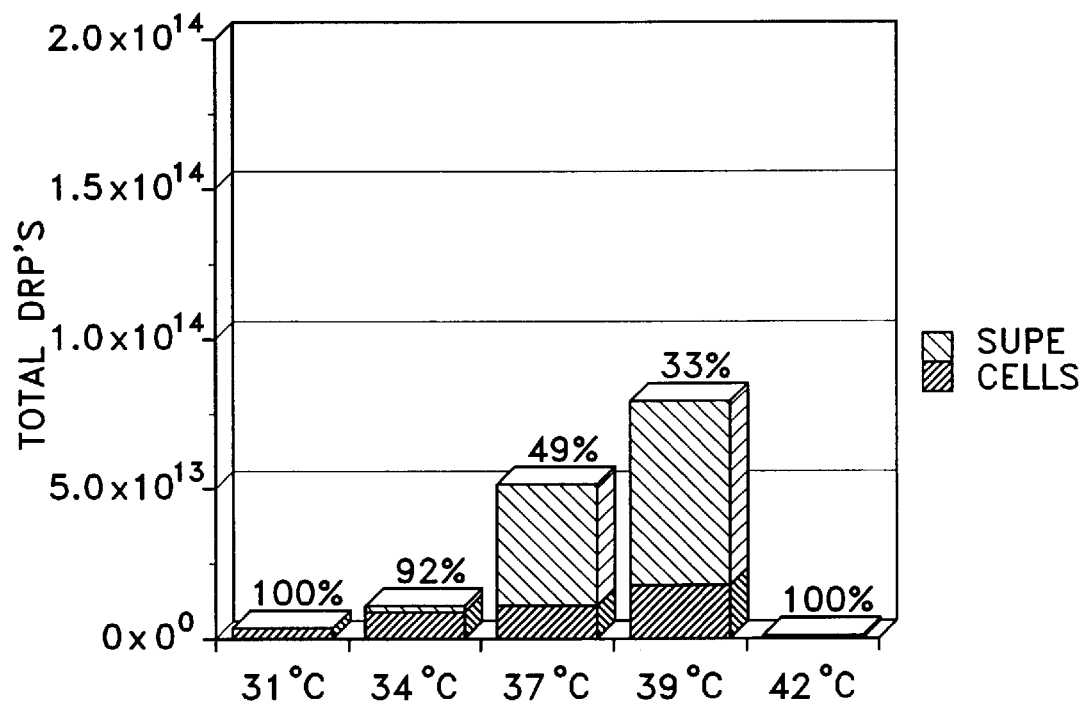
Figure 21C:
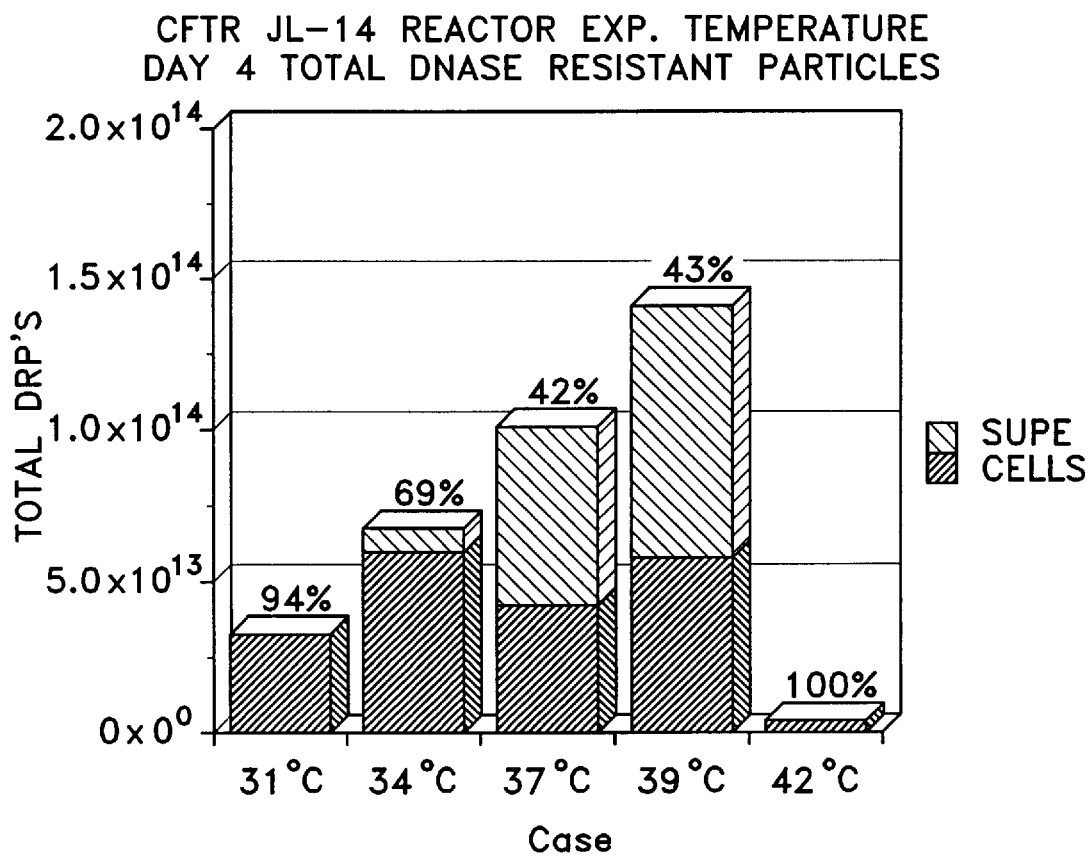

FIGS. 21A–C are bar graphs depicting the total DRPs in cell lysates (solid portion of each bar) and cell culture media (hatched portion of each bar) on day 2 (FIG. 21A), day 3 (FIG. 21B), and day 4 (FIG. 21C) post-infection in bioreactors in which the cell culture media was maintained at the indicated temperature. Percentages above each bar indicate the percentage of total DRPs in the cell lysate. The data show that when the culture medium was maintained at 39° C., 66%, 67%, and 57% of the total DRPs were found in the cell culture medium on days 2, 3, and 4, respectively. The data further indicate that a higher percentage of DRPs was found in the cell culture medium when the culture media was maintained at 39° C., compared to 37° C. or 42° C.

Figure 22A:
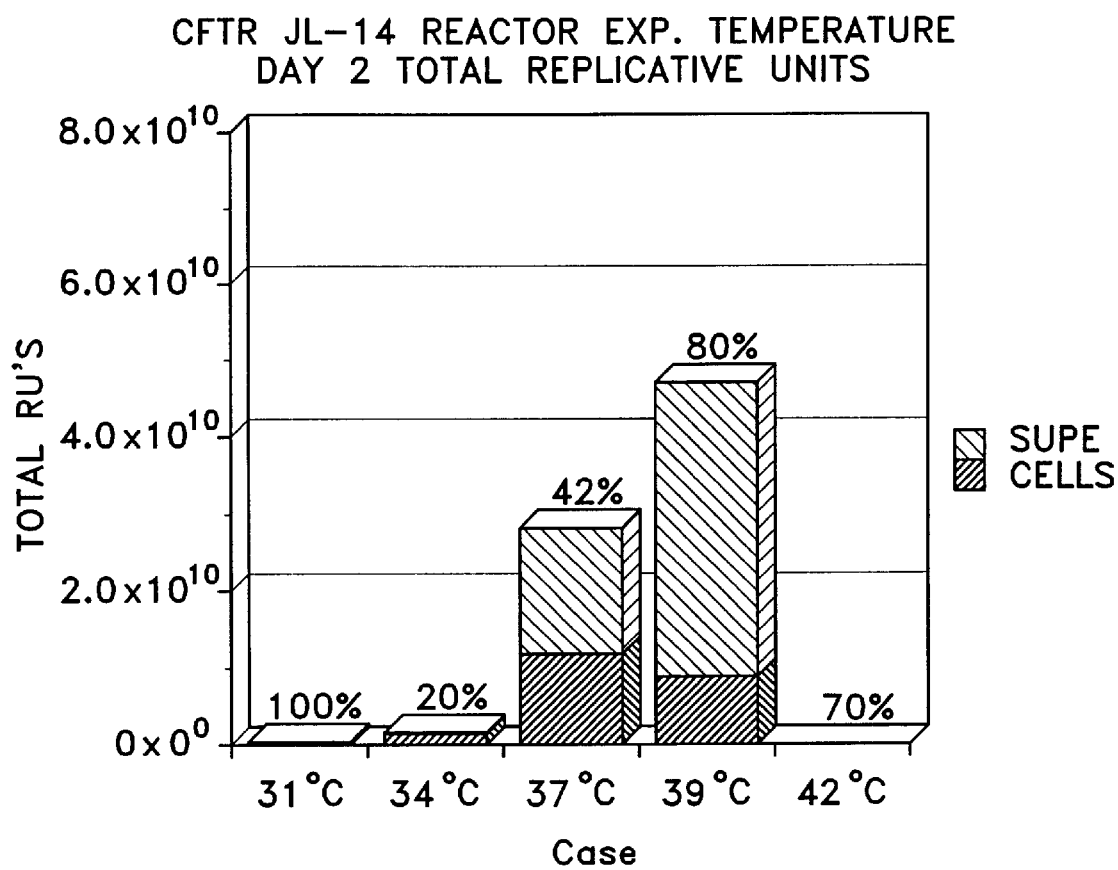
FIGS. 22A–C are bar graphs depicting the total RUs in cell lysates (solid portion of each bar) and cell culture media (hatched portion of each bar) on day 2 (FIG. 22A), day 3 (FIG. 22B), and day 4 (FIG. 22C) post-infection in bioreactors in which the cell culture media was maintained at the indicated temperature. Percentages above each bar in FIG. 22A indicate the percentage of total RUs in the cell lysate.
Figure 22B:
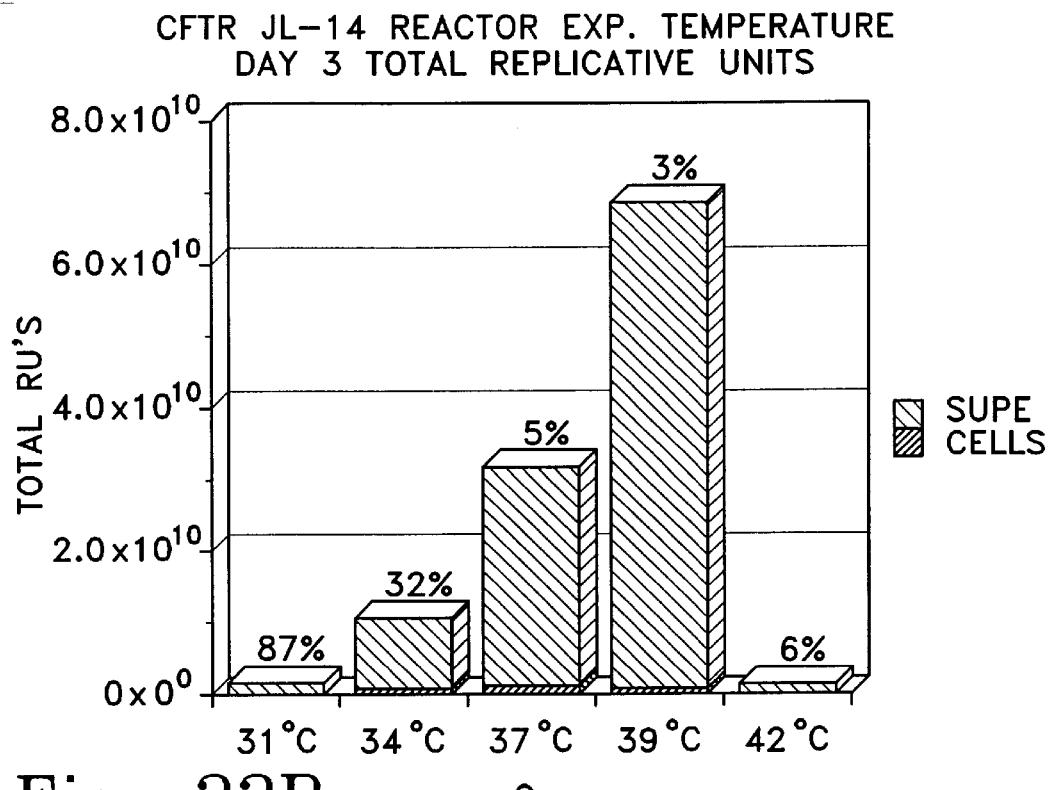
Figure 22C:
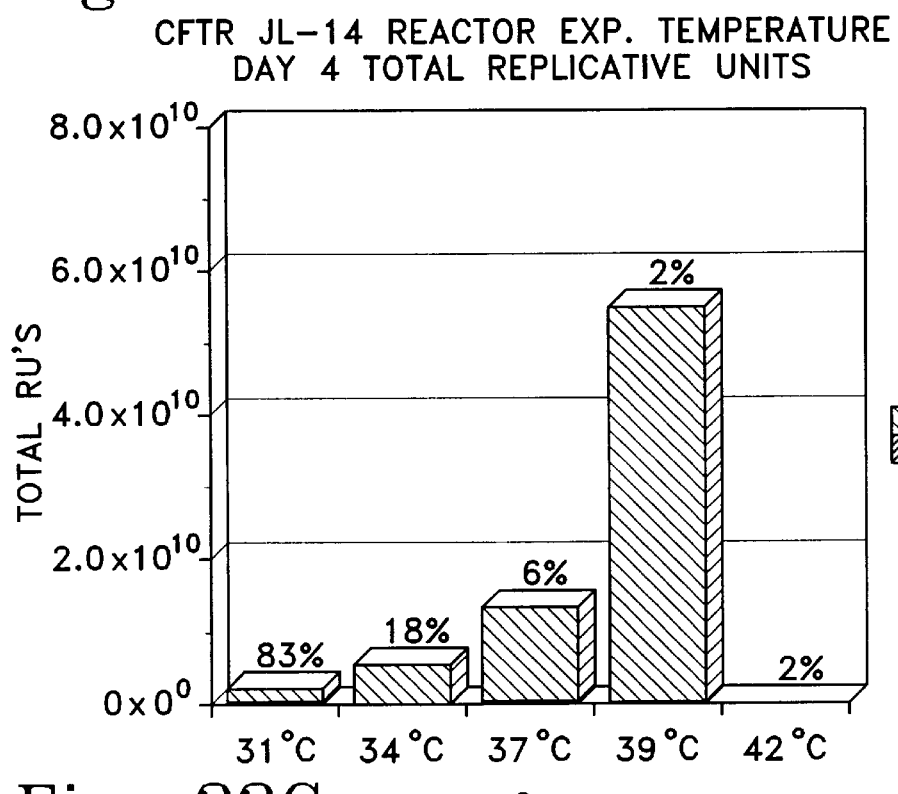

FIGS. 22A–C are bar graphs depicting the total RUs in cell lysates (solid portion of each bar) and cell culture media (hatched portion of each bar) on day 2 (FIG. 22A), day 3 (FIG. 22B), and day 4 (FIG. 22C) post-infection in bioreactors in which the cell culture media was maintained at the indicated temperature. Percentages above each bar in FIG. 22A indicate the percentage of total RUs in the cell culture medium. These data show that when the culture medium was maintained at 39° C., 80%, 97%, and 98% of total RUs were found in the cell culture medium on days 2, 3, and 4, respectively. The total cell density did not change appreciably under these culture conditions.

Example 17

Effect of Culture Medium Supplements on Release of rAAV Vector Particles into the Cell Culture Medium JL14 cells were grown in bioreactors and infected with adenovirus essentially as described in Example 2. Cells were transferred to bioreactors containing various media, as follows: (1) DMEM; (2) DMEM +4 g/liter glucose; (3) DMEM+4 g/liter glucose +4 mM glutamine; (4) DMEM+4 g/liter glucose +4 mM glutamine+amino acids +vitamins ("complete"); (5) 2X DMEM. All starting osmolalities were adjusted to 285–300 mOsm. Other parameters were as follows: temperature maintained at 39° C.; pH maintained at 8.0; $DO_2$ =30%; and agitation =150 rpm. Three days post-infection, the cell culture supernatant was assayed for rAAV vector particles.

Figure 23:
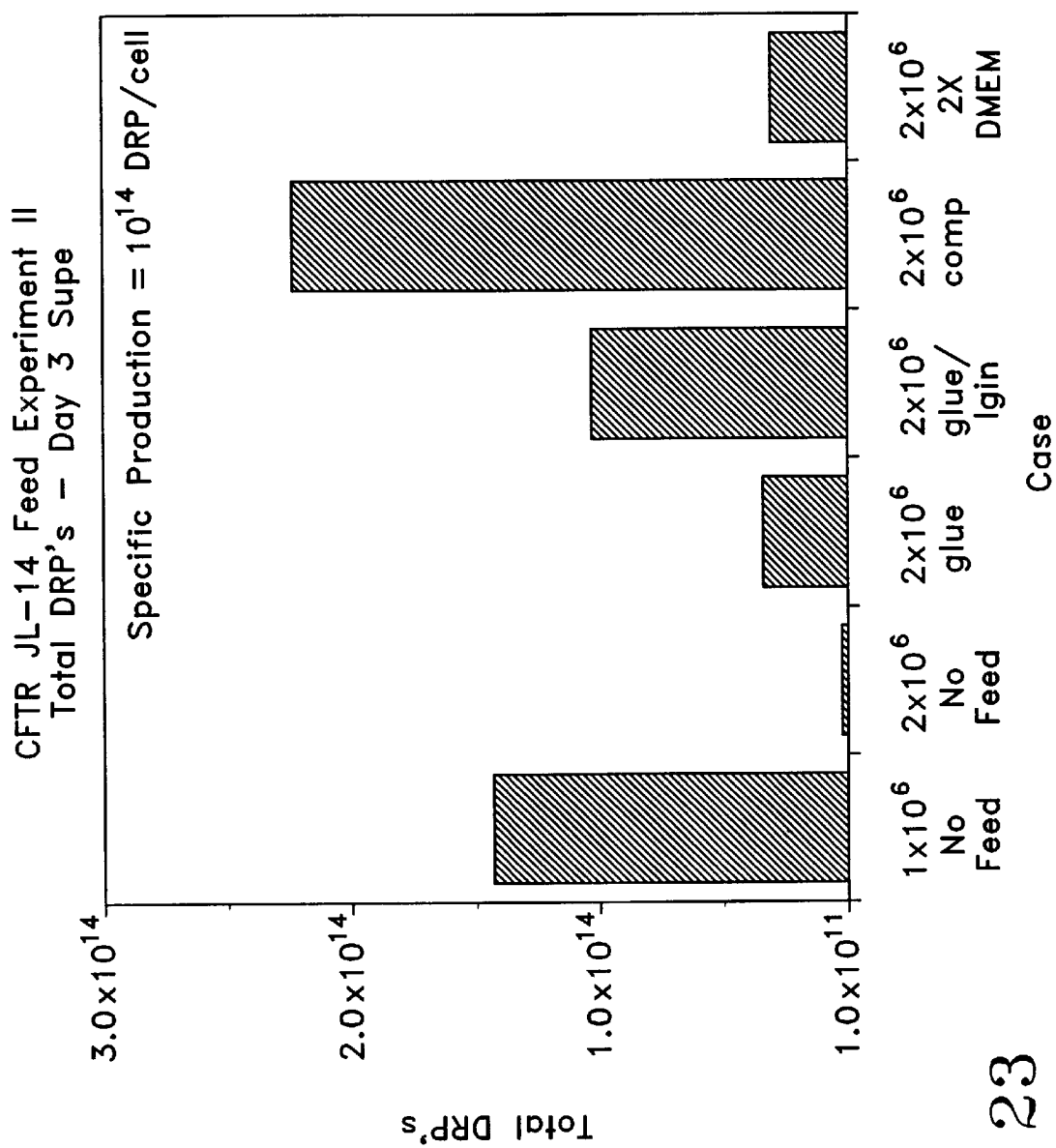
FIG. 23 is a bar graph depicting the total DRPs in the culture media three days post-infection in cultures grown in the various media indicated.
Figure 24:
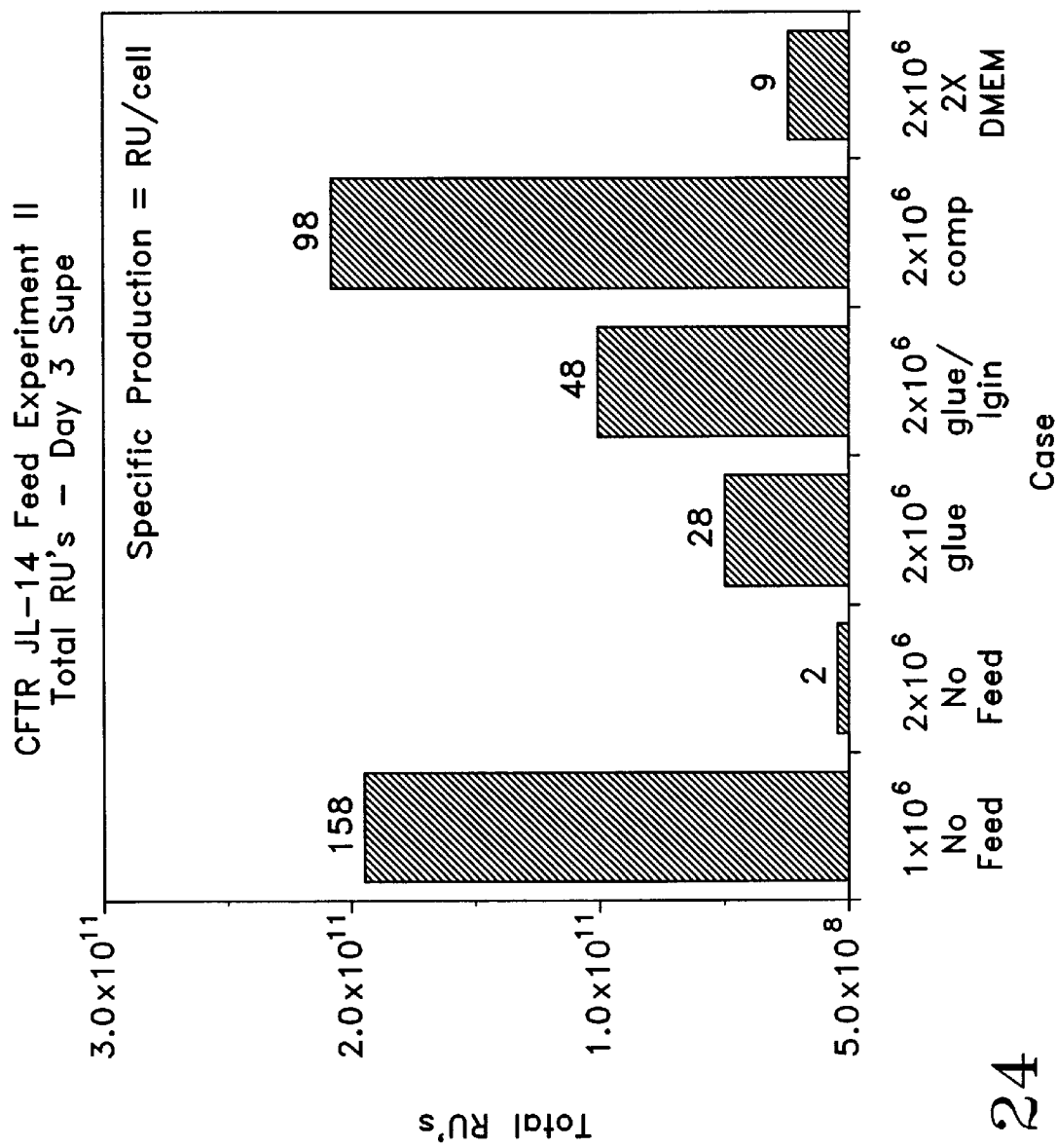
FIG. 24 is a bar graph depicting the RUs in the culture media three days post-infection in cultures grown in the various media indicated.
Figure 25:
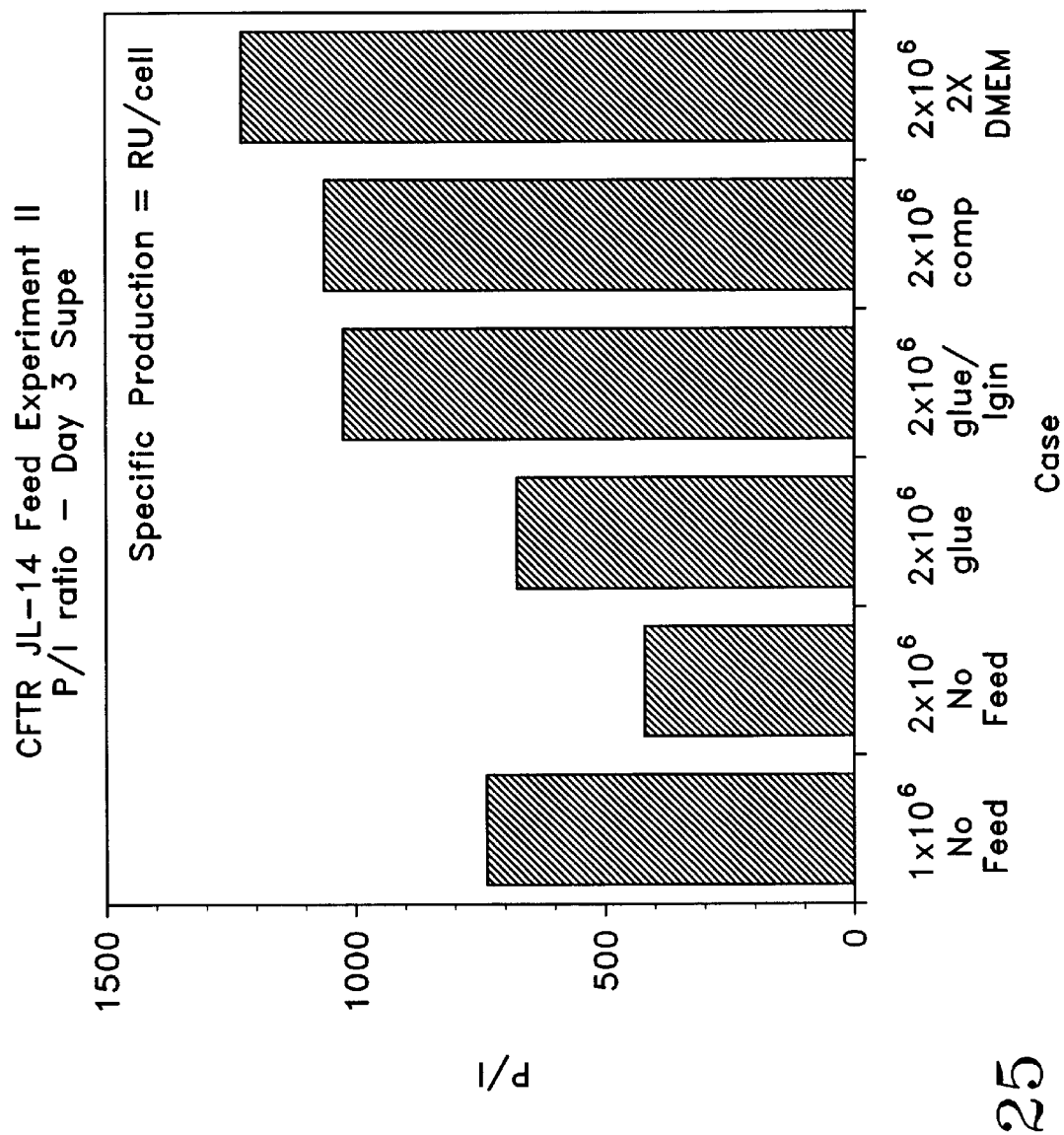
FIG. 25 is a bar graph depicting the P/I ratio of viral particles in the cell culture media when cultures were grown in the various media indicated.
Figure 26:
FIG. 26 shows the relationship of 26A and 26B.

The results are shown in FIGS. 23, 24, and 25.

FIG. 23 is a bar graph depicting the total DRPs in the culture media three days post-infection in cultures grown in the various media indicated.

FIG. 24 is a bar graph depicting the RUs in the culture media three days post-infection in cultures grown in the various media indicated.

FIG. 25 is a bar graph depicting the P/I ratio of viral particles in the cell culture media when cultures were grown in the various media indicated.

Example 18

Effect of Osmolality and Conductivity on Release of rAAV Vector Particles into the Cell Culture Medium from Attached Cell Cultures Example 18A Vector Release from Attached Cell Cultures Media. The media in Table 7 was used in the experiments of this Example.

TABLE 7

Base Media Formulation

| Component | DMEM liquid (Bio Whittaker) mg/L | DMEM Powder (Bio Whittaker) mg/L |
|---|---|---|
| CaCl2 (anhydrous) | 200 | |
| CaCl2.2H2O | | 264.86 |
| Fe(NO3)3.9H2O | 0.10 | 0.10 |
| KCl | 400 | 400 |
| MgSO4 (anhydrous) | | 97.6 |
| MgSO4.7H2O | 200 | |
| NaCl | 6400 | 6400 |
| NaHCO3 | 3700 | |
| NaH2PO4 | | 108.69 |
| NaH2PO4.H2O | 125 | |
| Glucose | 4500 | 4500 |
| Phenol Red | 15.00 | |

TABLE 7-continued

Base Media Formulation

| Component | DMEM liquid (Bio Whittaker) mg/L | DMEM Powder (Bio Whittaker) mg/L |
|---|---|---|
| Phenol Red.Na | | 15.34 |
| Sodium Pyruvate | 110 | |
| L-Arginine.HCl | 84.00 | 84.00 |
| L-Cysteine | 48.00 | |
| L-Cysteine.2HCl | | 62.58 |
| L-Glutamine | 584.00 | 584.00 |
| Glycine | 30.00 | 30.00 |
| L-Histidine.HCl.H2O | 42.00 | 42.00 |
| L-Isoleucine | 104.80 | 104.80 |
| L-Leucine | 104.80 | 104.80 |
| L-Lysine.HCl | 146.20 | 146.20 |
| L-Methionine | 30.00 | 30.00 |
| L-Phenylalanine | 66.00 | 66.00 |
| L-Serine | 42.00 | 42.00 |
| L-Threonine | 95.20 | 95.20 |
| L-Tryptophan | 16.00 | 16.00 |
| L-Tyrosine | 72.00 | |
| L-Tyrosine.2Na | | 103.79 |
| L-Valine | 93.60 | 93.60 |
| D-Ca-Pantothenate | 4.00 | 4.00 |
| Choline Chloride | 4.00 | 4.00 |
| Folic Acid | 4.00 | 4.00 |
| i-Inisitol | 7.00 | 7.00 |
| Nicotinamide | 4.00 | 4.00 |
| Pyridoxine.HCl | 4.00 | 4.00 |
| Riboflavin | 0.40 | 0.40 |
| Thiamine.HCl | 4.00 | 4.00 |

To assess the effects of changes in osmolality and conductivity on release of rAAV vector particles into the cell culture medium of attached cell cultures, JL14 cells were innoculated at about $1 \times 10^7$ cells per flask in T-225 cells and grown in 54 ml of the medium shown in Table 7 with additional formulation as described below in Table 8 (FBS and L-glutamine were supplemented to 1%) overnight at 37° C., 10% $CO_2$, pH 7.2. Twenty four hours post seeding of the cells in the T225 flasks the media was removed and replaced with 54 ml of each test media described below and infected with Ad5 at an MOI of 10. T225 cultures as described were maintained for 72 hours at 37° C., 10% $CO_2$ to allow for rAAV production. Three days later cells and supernatant were collected from each test flask and total cell density as well slot blot and infectivity assays comparing released rAAV (supernatant) and cell associated rAAV (lysed) were performed. "Adjusted osmolality" refers to the osmolality after adding indicated solute, which represents the osmolality at the beginning of the experiment (i.e., upon infection with adenovirus).

TABLE 8

Media Formulation Table

| Media Base | Initial mOsm | Added Solute | Solute mOsm Added | Adjusted mOsm | Conductivity mS |
|---|---|---|---|---|---|
| Liquid DMEM | 359 | None | 0 | 359 | 13.30 |
| Powdered DMEM | 363 | None | 0 | 363 | 13.75 |
| Powdered DMEM | 363 | NaCl | 27 | 390 | 14.88 |
| Powdered DMEM | 363 | NaCl | 66 | 429 | 16.55 |
| Powdered DMEM | 363 | Sorbitol | 28 | 391 | 13.46 |
| Powdered DMEM | 363 | Sorbitol | 63 | 426 | 13.33 |

Figure 27:
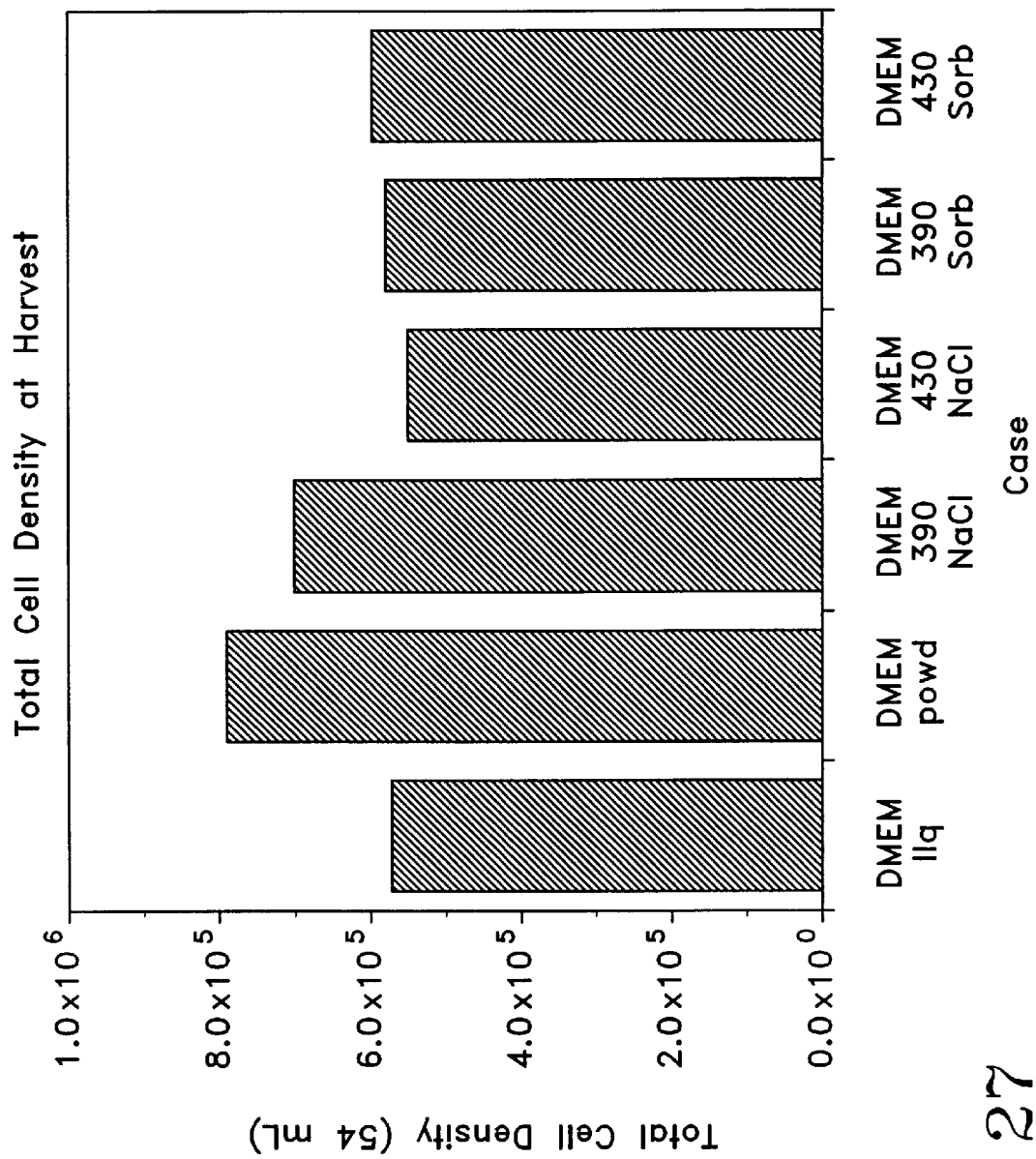
FIG. 27 is a bar graph depicting the total cell density at the time of harvest for the various media formulations.
Figure 28:
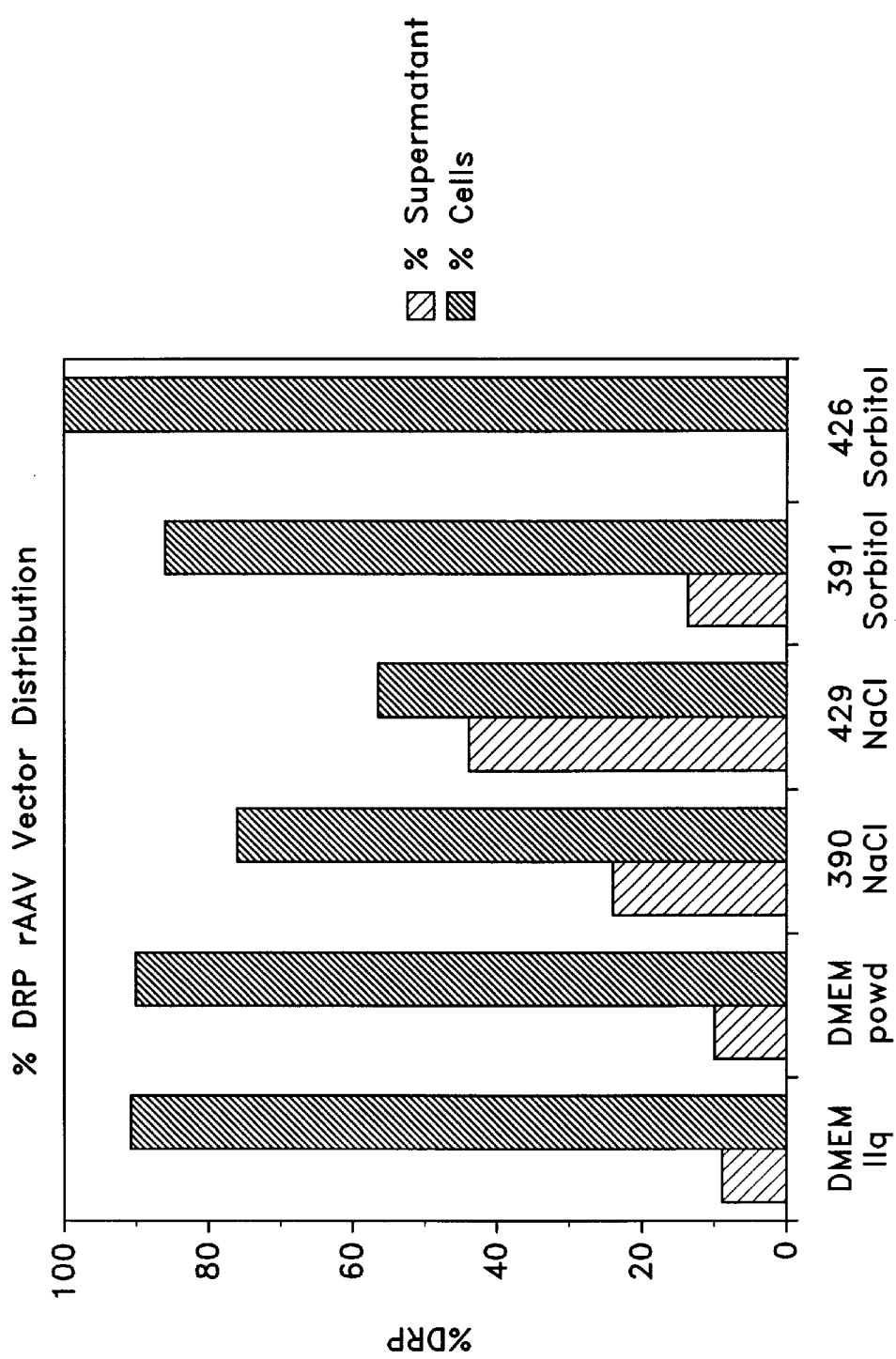
FIG. 28 is a bar graph depicting the percent of DRPs released in the cell culture medium (white bars) versus those retained in the cell (black bars) from attached cell cultures for the various formulations tested.

The results are shown in FIGS. 27–30. The total cell density is not appreciably different if the media is formulated with NaCl or sorbitol (FIG. 27). The maximum percentage of total rAAV vector was released into the culture media (in terms of DRP) when the adjusted osmolality of the media is formulated at approximately 429 mOsm using NaCl (resulting in a conductivity of 16.55 mS) compared with the other starting osmolalities and conductivities tested (FIG. 28). In contrast, there were no released rAAV vector particles detected when sorbitol with adjusted osmolality of 426 (conductivity of 13.33 mS) (FIG. 28).

Figure 29:
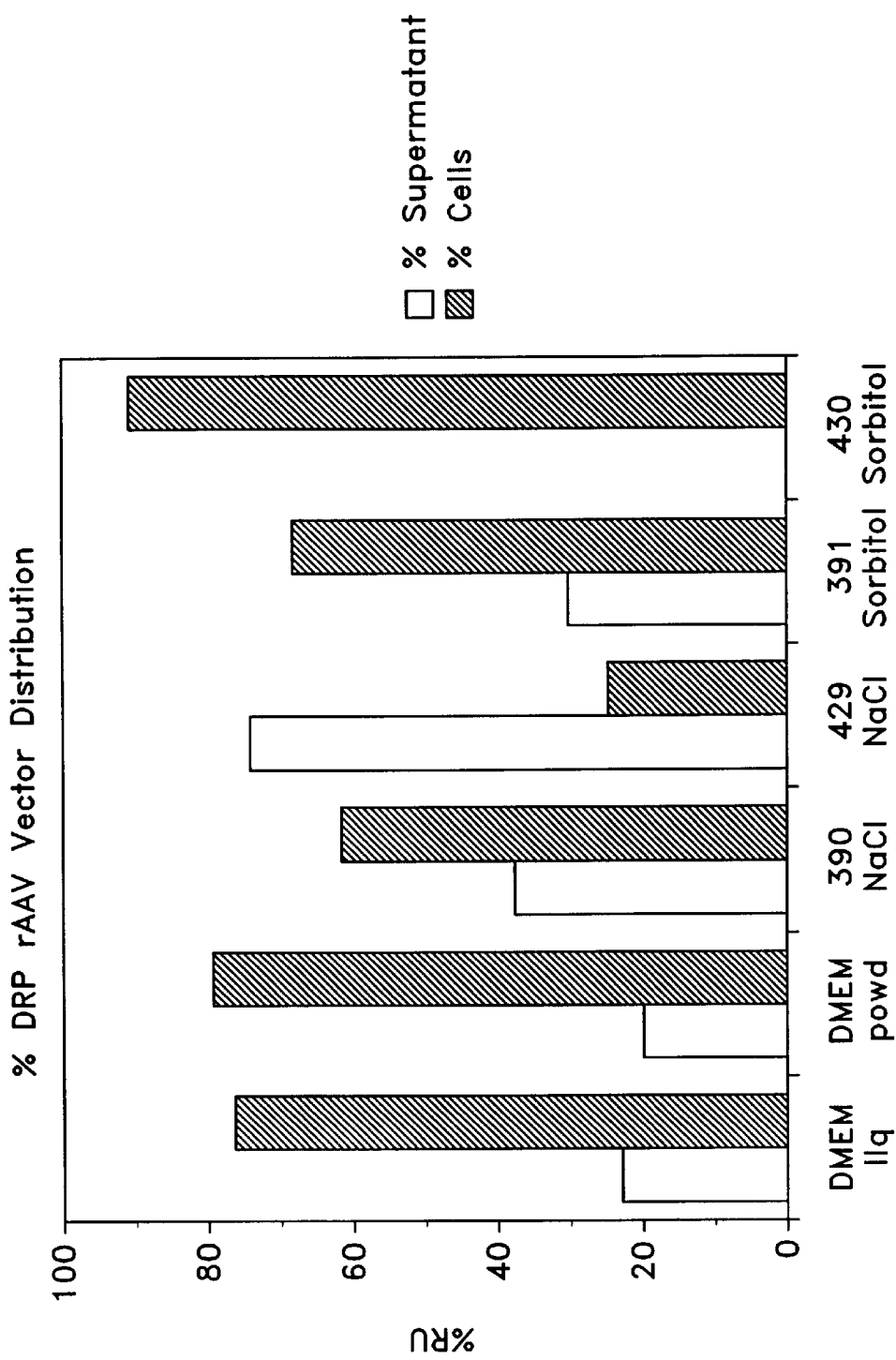
FIG. 29 is a bar graph depicting the percent of RUs released in the cell culture medium (white bars) versus those retained in the cell (black bars) from attached cell cultures for the various formulations tested.

Similarly, when vector production was measured in terms of RUs, the maximum percentage of infectious rAAV vector was released in the culture medium when the starting osmolality of the media is formulated approximately 429 mOsm with NaCl resulting in a conductivity of 16.55 mS (about 80%) compared with the other starting osmolalities and conductivities tested (FIG. 29). In contrast, less than 20% of total RUs were in the culture supernatant when sorbitol was used to adjust the osmolality to 426 mOsm (conductivity of 13.33 mS).

Figure 30:
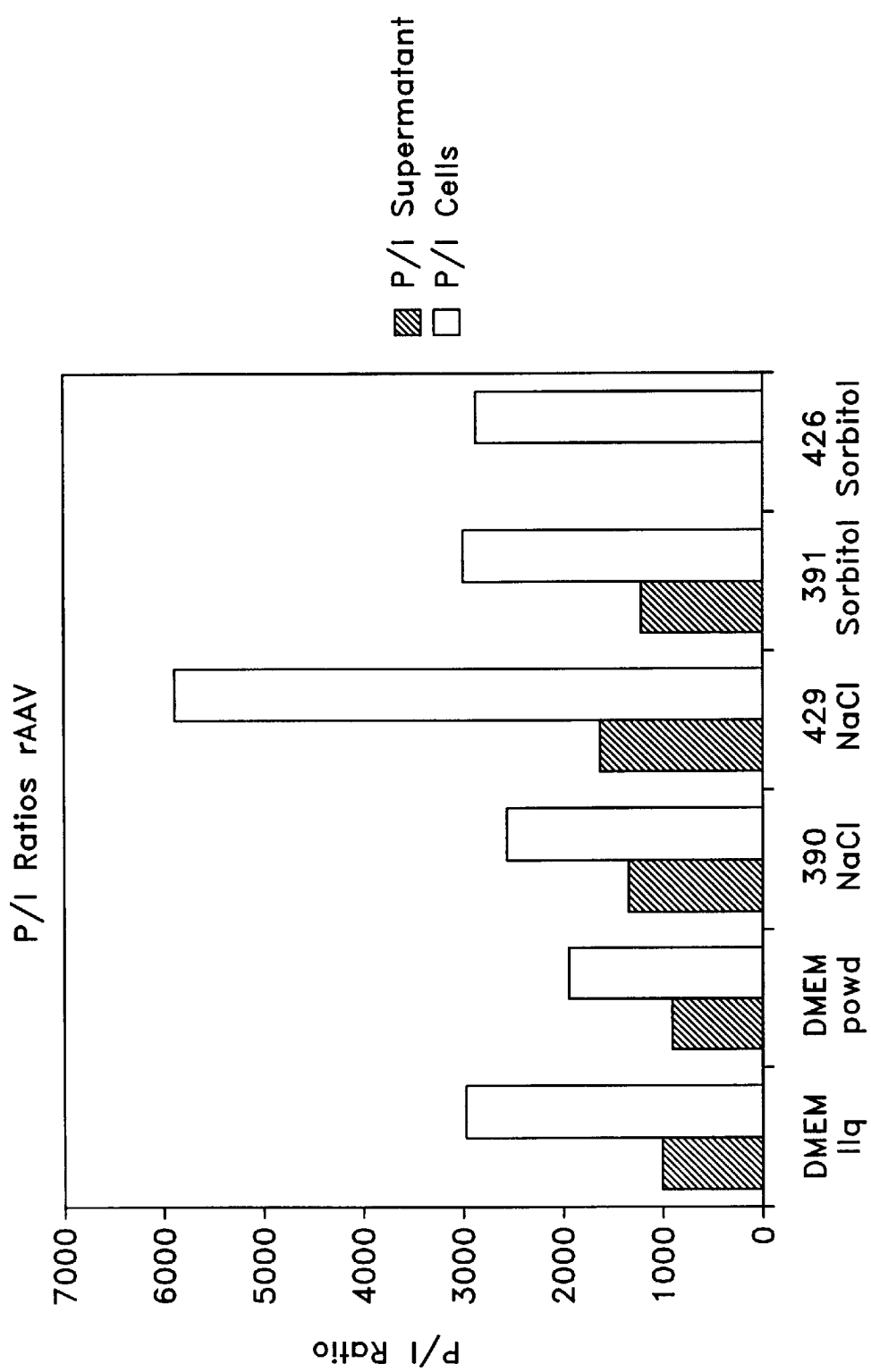
FIG. 30 is a bar graph depicting the particle infectivity (P/I) ratio of rAAV particles harvested from cell lysates (white bars) and cell culture medium (black bars) from attached cell cultures for the various media formulations.

P/I (particle to infectivity ratio) data indicate that the majority of the rAAV vector released into the cell culture medium is infectious (FIG. 30).

Example 18B Effect of Varying Times of Adjusting Osmolality and Conductivity on Vector Release from Attached Cell Cultures JL14 cells were inoculated at about $1 \times 10^7$ cells per flask in T-225 cells and grown in 54 ml of the medium shown in Table 7 overnight at 37° C., 10% $CO_2$, pH 7.2. Twenty four hours post seeding of the cells in the T225 flasks the media was removed and replaced with 54 ml media listed in Table 9 and infected with Ad5 at an MOI of 10. At various time points the media was adjusted with 5M NaCl to achieve a final osmolarity of 450 mOsm. T225 cultures as described were maintained for 72 hours at 37° C., 10% $CO_2$ to allow for rAAV production. Three days later cells and supernatant were collected from each test flask and total cell density as well slot blot infectivity assays comparing released rAAV (supernatant) and cell associated rAAV (lysed) were performed.

450 mOsm cultures released 47%, 69%, and 74% for day 0, 1, and 2 respectively. As little as 1–4 hours prior to harvest on day 3 adjustment of the osmolality and conductivity to 450 mOsm with NaCl results in a majority of infectious RUs released in the cell culture medium (FIG. 31B).

Figure 32:
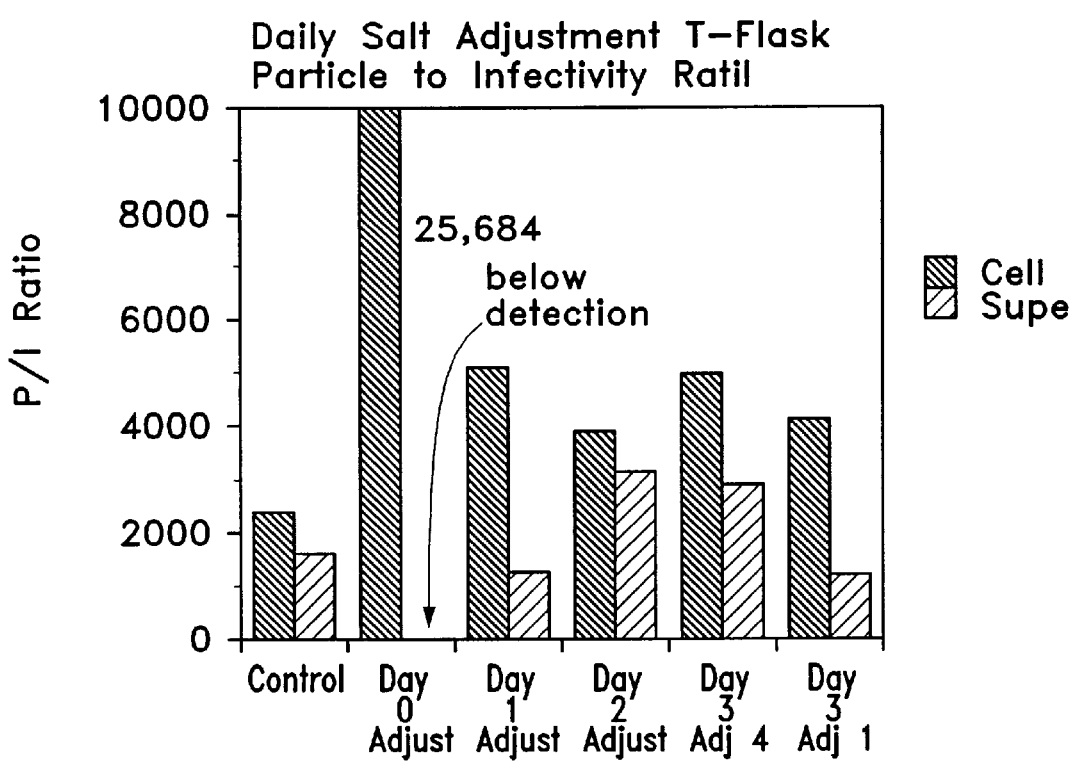
FIG. 32 is a bar depicting the particle infectivity (P/I) ratio of rAAV particles harvested from cell lysates (black bars) and cell culture medium (hatched bars) from attached cell cultures adjusted to 450 mOsm with NaCl at the times indicated in Table 9.

P/I (particle to infectivity ratio) data indicate that the majority of the rAAV vector released into the cell culture medium is infectious (FIG. 32).

Example 19

Effect of Osmolality and Conductivity on Release of rAAV Vector particles into the Cell Culture Medium from Suspension Cell Cultures To further assess the effects of starting osmolality and conductivity of the culture cell medium on the release of rAAV into the cell culture medium from suspension cell cultures, JL14 cells were grown in bioreactors and infected with adenovirus essentially as described in Example 14 using media as described in Table 5. The adjusted osmolality in the individual bioreactors (at the beginning of the experiment) was as described in Table 10. In each reactor, the pH was maintained at pH 8.0 (0.05); 37° C.; DO2=30%; and agitation 150 rpm. The pH of 8.0 was maintained by the controlled addition of sodium carbonate to the culture medium. On days 1,2, and 3 cultures were analyzed for conductivity, osmolality, total cell density, and glucose consumption. On days 2 and 3 post infection, cell lysates and cell culture media were collected and analyzed for rAAV vector production.

TABLE 9

Media Formulations

| Media Base | Starting mOsm | Added Solute | Day Solute Adjusted | Solute mOsm Added | Final mOsm | Day 3 Conductivity mS |
|---|---|---|---|---|---|---|
| Powdered DMEM | 363 | None | ND | 0 | 363 | 12.6 |
| Powdered DMEM | 363 | NaCl | 0 | 87 | 450 | 17 |
| Powdered DMEM | 363 | NaCl | 1 | 87 | 450 | 16.9 |
| Powdered DMEM | 363 | NaCl | 2 | 87 | 450 | 16.9 |
| Powdered DMEM | 363 | NaCl | Day 3 (−4 hr) | 87 | 450 | 16.9 |
| Powdered DMEM | 363 | NaCl | Day 3 (−1 hr) | 87 | 450 | 16.8 |

Figure 31A:
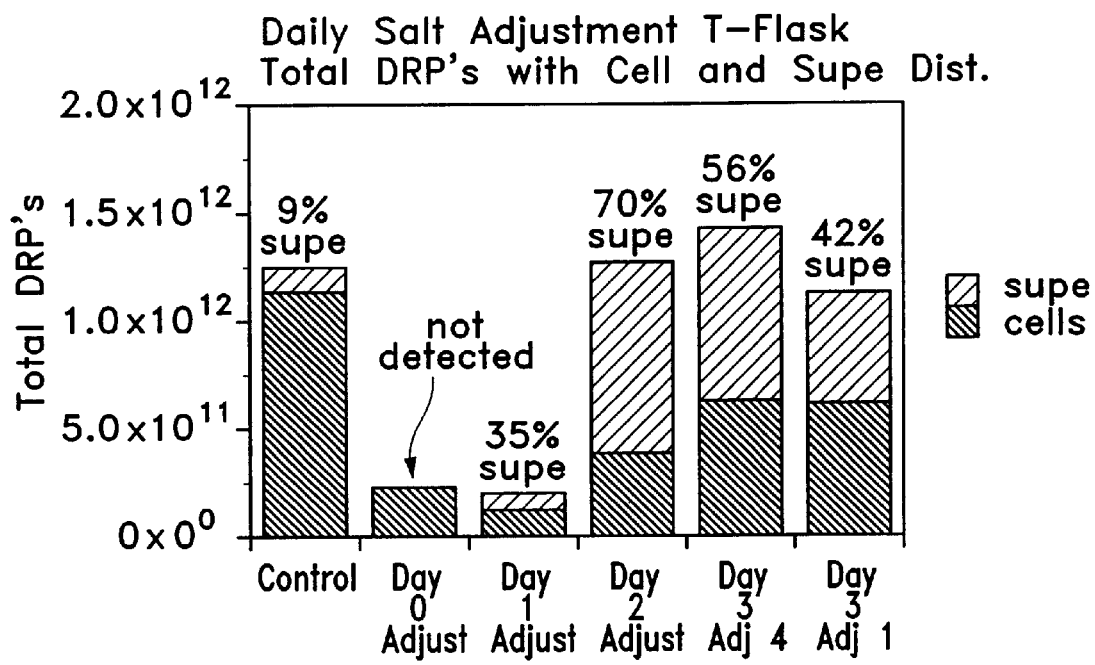
FIGS. 31A and 31B are bar graphs depicting the total DRPs (FIG. 31A) and RUs (FIG. 31B) in cell lysates (solid portion of each bar) and cell culture media (hatched portion of each bar) for attached cell cultures adjusted to 450 mOsm with NaCl at the times indicated in Table 9.
Figure 31B:
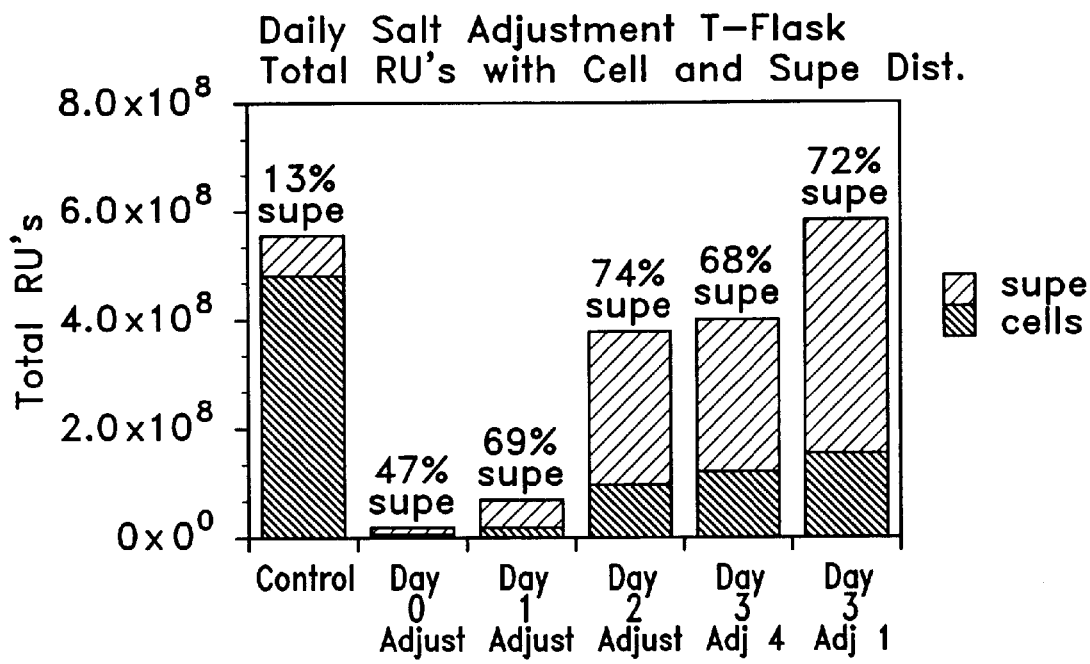

The results are shown in FIGS. 31A, 31B and 32. As shown in FIG. 31A, the majority of DRPs (70%) were released into the media with adjustment of the osmolality and corresponding conductivity at day 2 of rAAV production and that adjustment of the osmolality to 450 mOsm and conductivity with NaCl 4 hours prior to harvest on day 3 results in a majority of DRPs released in the cell culture medium (56%). A significant increase in release of rAAV vector was observed for all conditions in which osmolality (and thus conductivity) was adjusted after day 0 as compared to control.

The data demonstrate the majority of infectious rAAV vector (RUs) were released into the media with adjustment of the osmolality and corresponding conductivity at any time during rAAV production (FIG. 31 B). Only 13% of total RUs were released in the control 363 mOsm culture, while the

TABLE 10

Media formulations for suspension cell culture.

| Starting mOsm | Added Solute | Solute mOsm Added | Adjusted mOsm |
|---|---|---|---|
| 180 | NaCl | 70 | 250 |
| 180 | NaCl | 120 | 300 |
| 180 | NaCl | 170 | 350 |
| 180 | Sorbitol | 20 | 200 |
| 180 | Sorbitol | 120 | 300 |
| 180 | Sorbitol | 170 | 350 |

The results are shown in Tables 11 and 12 and FIGS. 33 and 34.

Table 11 summarizes the change in osmolality of the bioreactor cultures during rAAV vector production due to the controlled addition of sodium bicarbonate to the culture to control the pH of the culture to pH 8.0 (0.05). The data indicate that the changes in osmolality over time were not appreciably different between the NaCl formulated and sorbitol formulated cultures. Generally, osmolality increased over time in all cultures.

TABLE 11

Change in osmolality of the culture over time

| Added Solute | Initial Culture mOsm | Day 0 mOsm | Day 1 mOsm | Day 2 mOsm | Day 3 mOsm |
|---|---|---|---|---|---|
| NaCl | 250 | 265 | 307 | 367 | 396 |
| NaCl | 300 | 302 | 375 | 464 | 460 |
| NaCl | 350 | 348 | 402 | 454 | 485 |
| Sorbitol | 200 | 200 | 255 | 313 | 350 |
| Sorbitol | 300 | 302 | 375 | 464 | 460 |
| Sorbitol | 350 | 336 | 406 | 489 | 530 |

Table 12 depicts the change in conductivity of the bioreactor cultures during rAAV vector production due to the controlled addition of sodium bicarbonate to the culture to control the pH of the culture to pH 8.0 (0.05). The data shows the greatest increase in conductivity of the NaCl formulated bioreactor cultures over time compared to sorbitol formulated cultures which did not change appreciably over time.

TABLE 12

Change in conductivity of the culture over time

| Added Solute | Initial Culture mS | Day 0 mS | Day 1 mS | Day 2 mS | Day 3 mS |
|---|---|---|---|---|---|
| NaCl | 250 | 8.48 | 10 | 12.25 | 13.29 |
| NaCl | 300 | 10.15 | 12.64 | 14.39 | 15.52 |
| NaCl | 350 | 12.38 | 14.12 | 16.26 | 17.28 |
| Sorbitol | 200 | 5.3 | 7.54 | 9.35 | 10.51 |
| Sorbitol | 300 | 5.09 | 7.11 | 9.05 | 10.29 |
| Sorbitol | 350 | 4.88 | 7.48 | 10.04 | 11.5 |

Figure 33A:
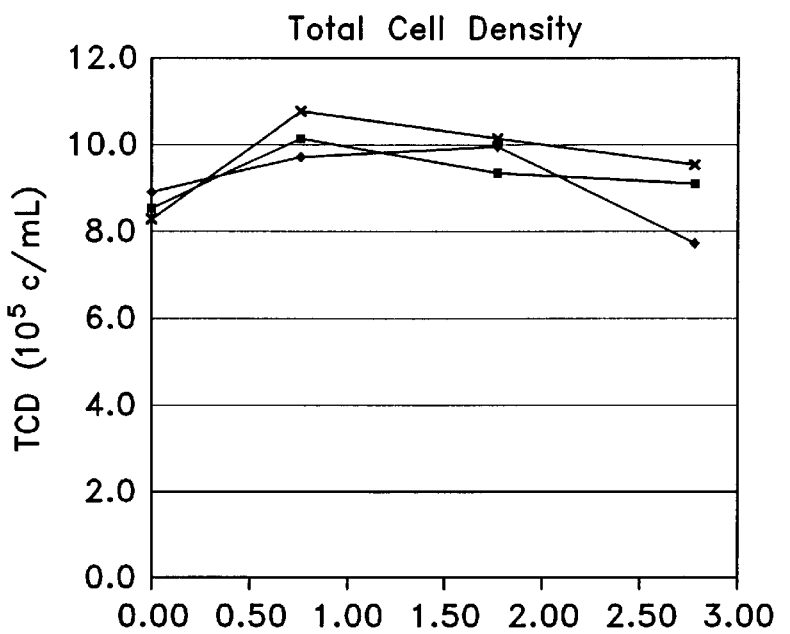
FIGS. 33A and 33B are graphs depicting total cell density for NaCl (FIG. 33A) and sorbitol (FIG. 33B) formulated cultures of various osmolalities and conductivities over time with rAAV vector production.
Figure 33B:
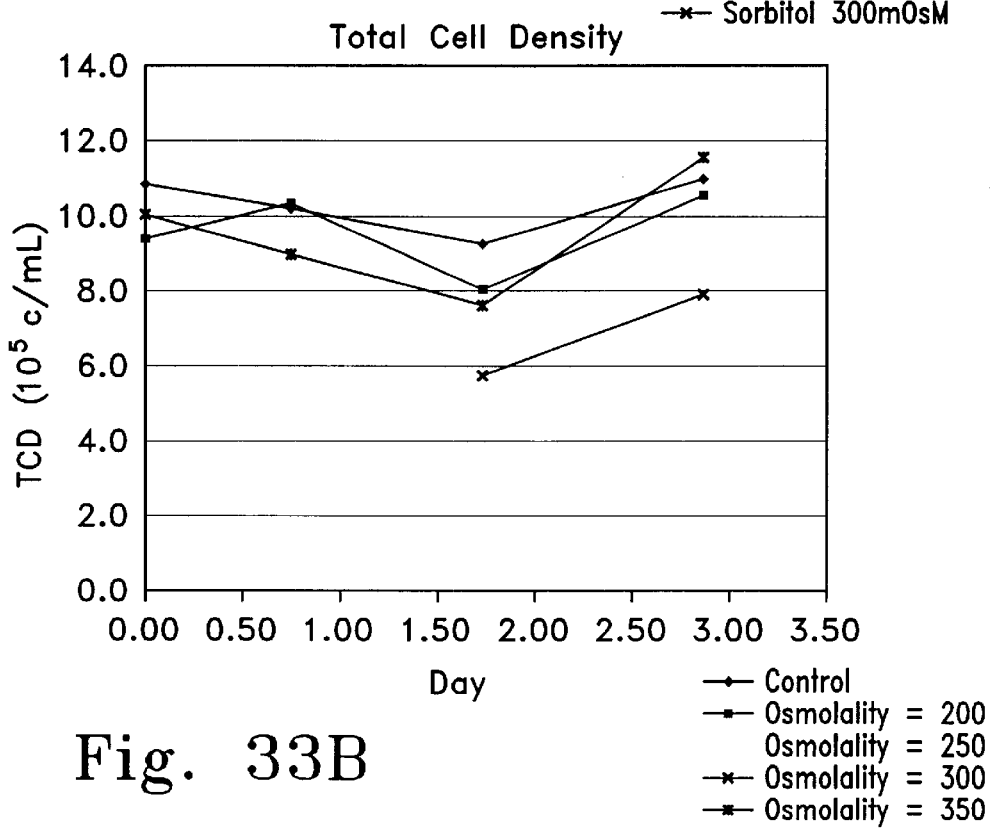
Figure 34A:
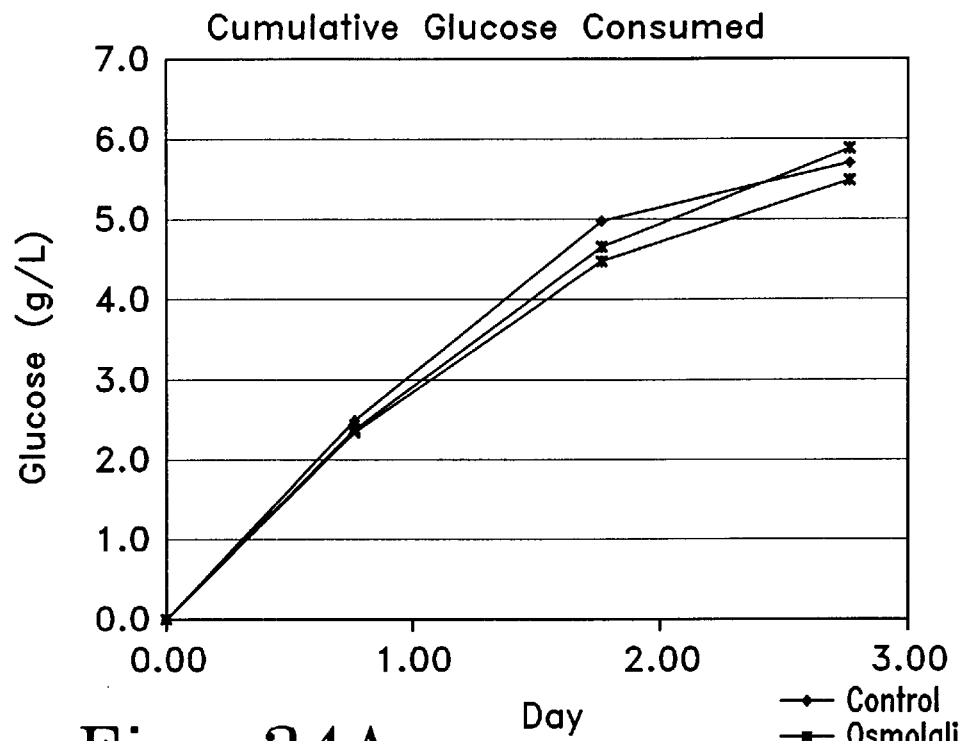
FIGS. 34A and 34B are graphs depicting glucose consumption rates of cells in NaCl (FIG. 34A) and sorbitol (FIG. 34B) formulated cultures of various osmolalities and conductivities over time with rAAV vector production.
Figure 34B:
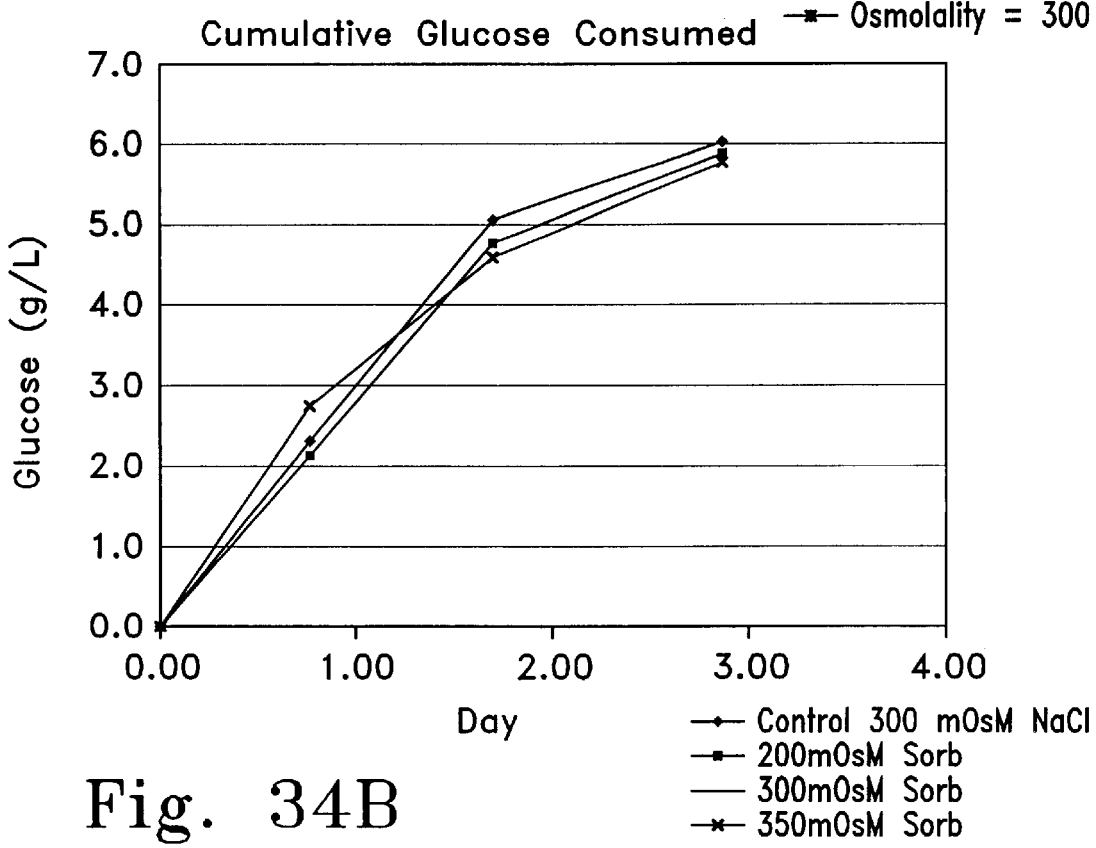

The total cell density remained generally constant over the culture period whether the cultures were formulated with NaCl or sorbitol (Compare FIGS. 33A and 33B). The metabolic rate of the cultures as measured by glucose consumption is equivalent between the NaCl and sorbitol formulated cultures is also equivalent (compare FIGS. 34A and 34B).

Figure 35A:
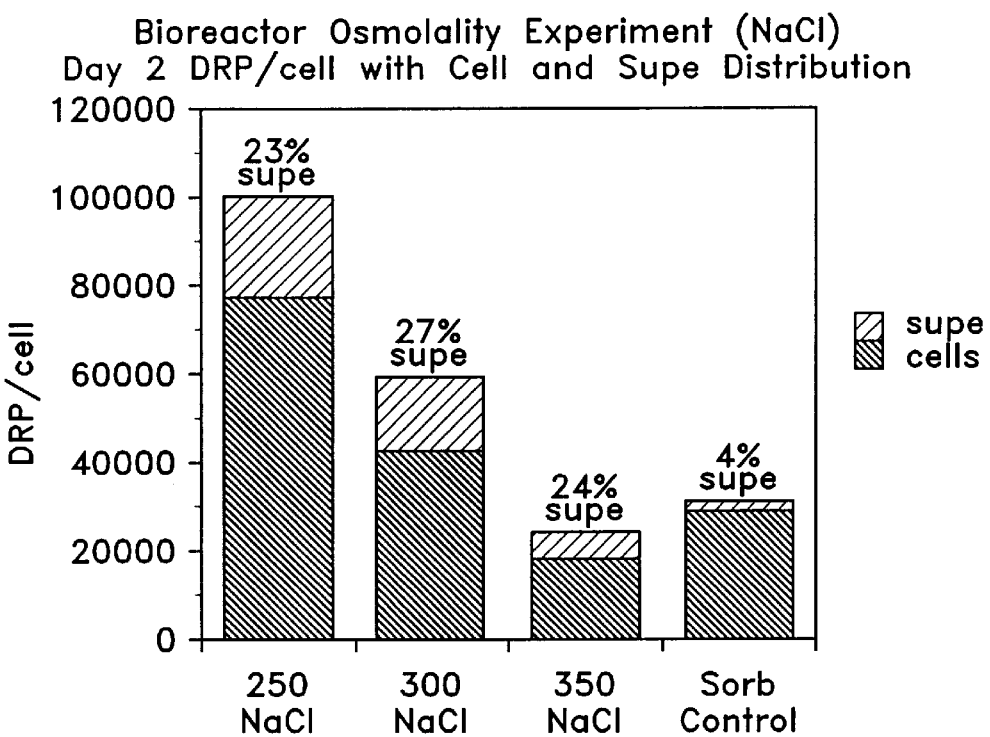
FIGS. 35A–D are bar graphs depicting the total DRPs in cell lysates (solid portion of each bar) and cell culture media (hatched portion of each bar) on day 2 (FIGS. 35A and 35C) and day 3 (FIGS. 35B and 35D) post infection in bioreactors for media formulated at the indicated starting osmolality with NaCl (FIGS. 35A and 35B) or sorbitol respectively. Percentages above each bar indicate the total DRPs in the cell lysate. The sorbitol control in FIGS. 35A and 35B represent the bioreactor formulated at 300 mOsm with sorbitol; the NaCl control in FIGS. 35C and 35D represent the bioreactor formulated with 300 mOsm NaCl.
Figure 35B:
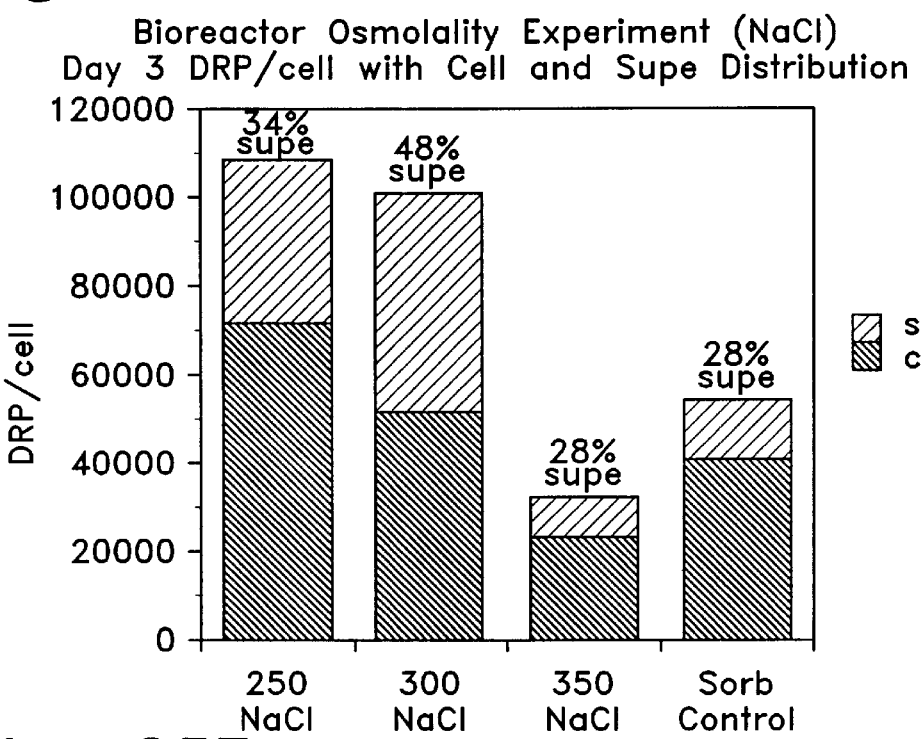
Figure 35C:
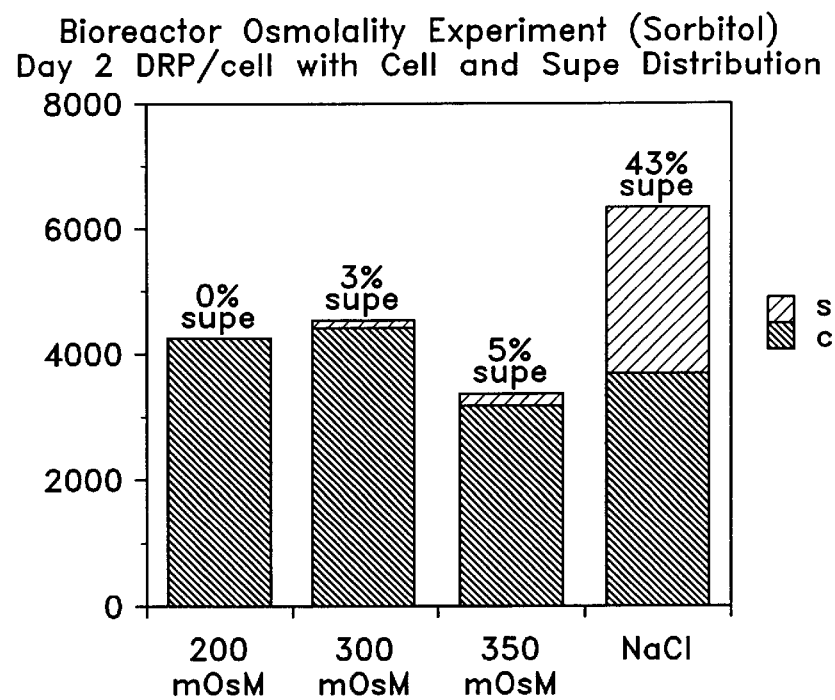
Figure 35D:
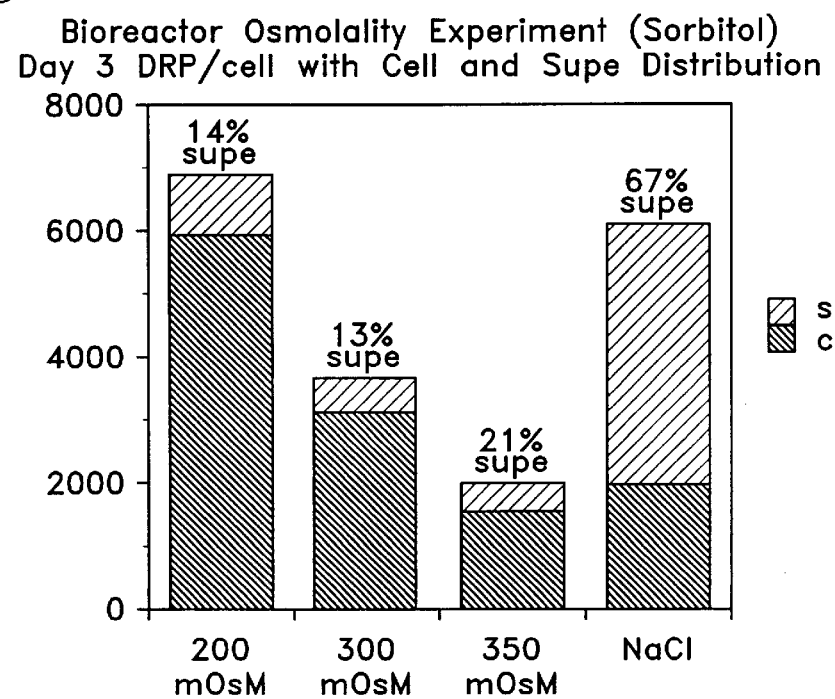
Figure 36A:
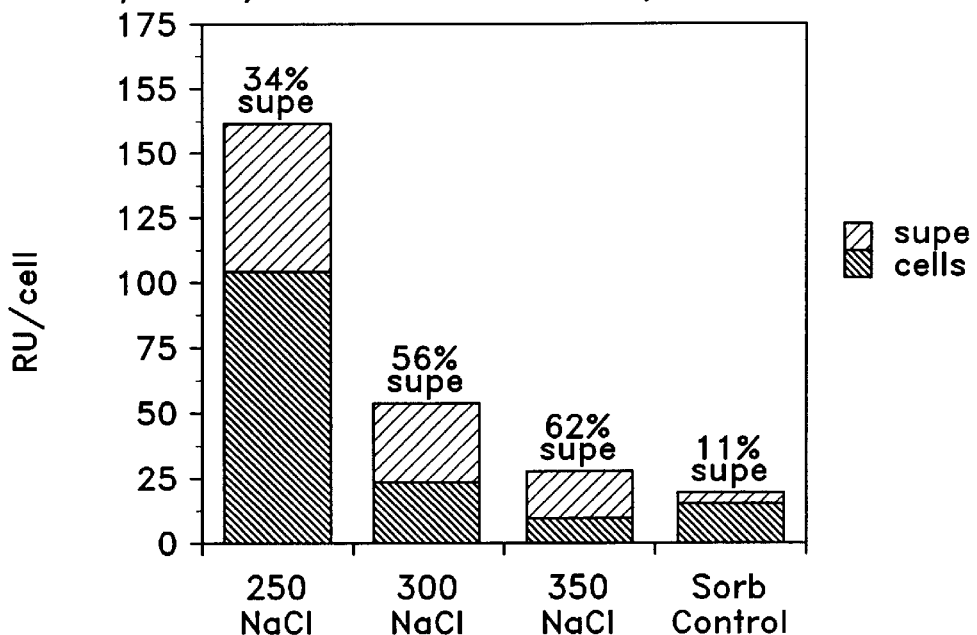
FIGS. 36A–D are bar graphs depicting the RUs per cell in cell lysates (solid portion of each bar) and cell culture media (hatched portion of each bar) on day 2 (FIGS. 36A and 36C) and day 3 (FIGS. 36B and 36D) post infection in bioreactors for media formulated at the indicated starting osmolality with NaCl (FIGS. 36A and 36B) or sorbitol (FIGS. 36C and 36D). Percentages above each bar indicate the percent of RUs per cell contained in the cell lysate.
Figure 36B:
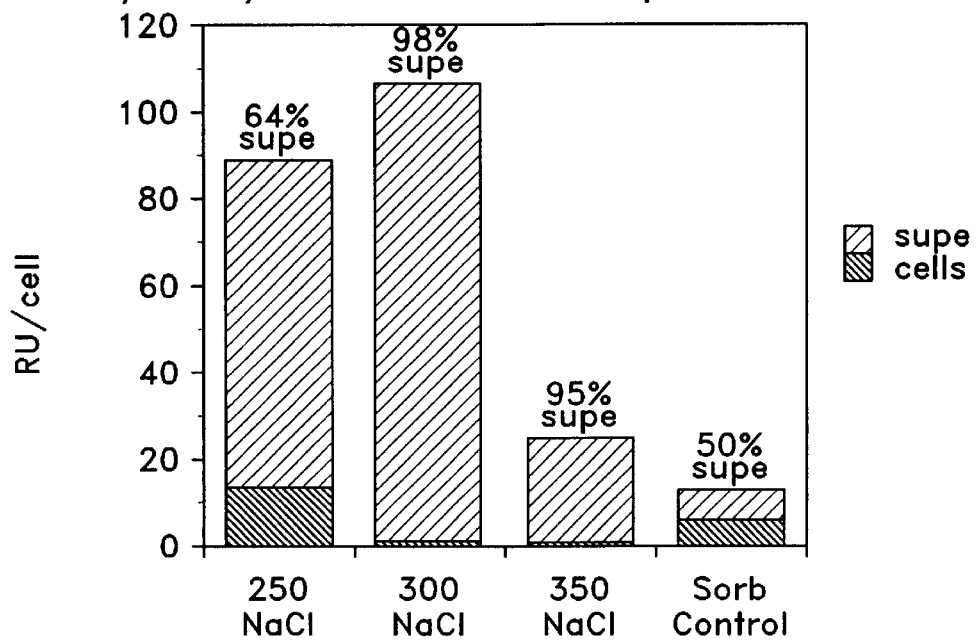
Figure 36C:
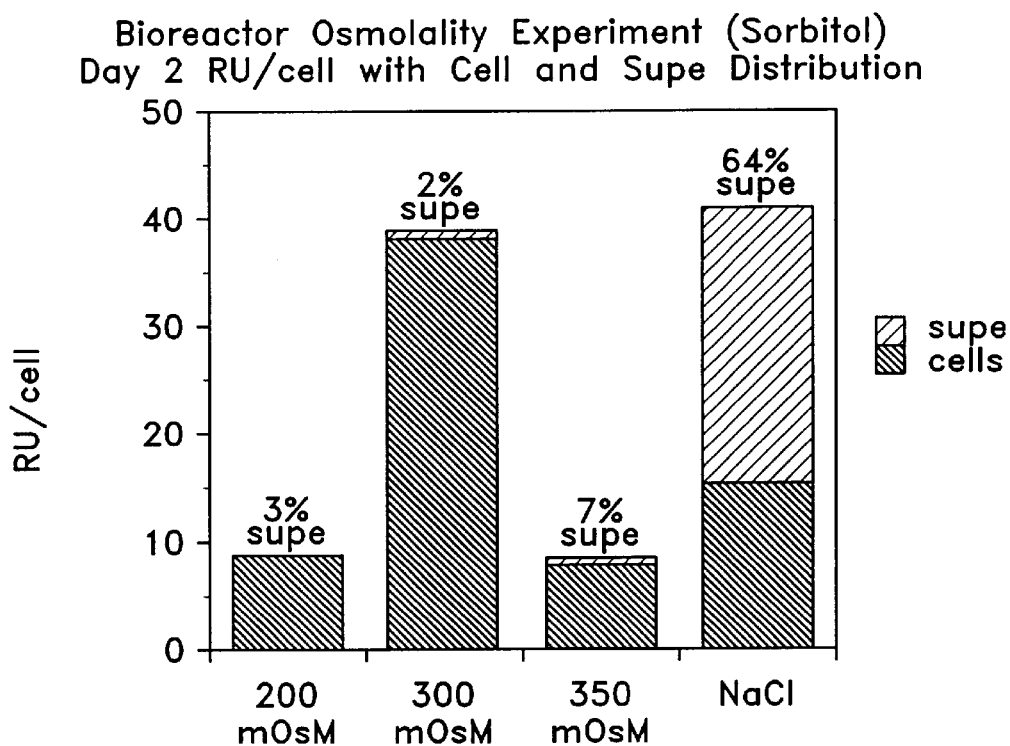
Figure 36D:
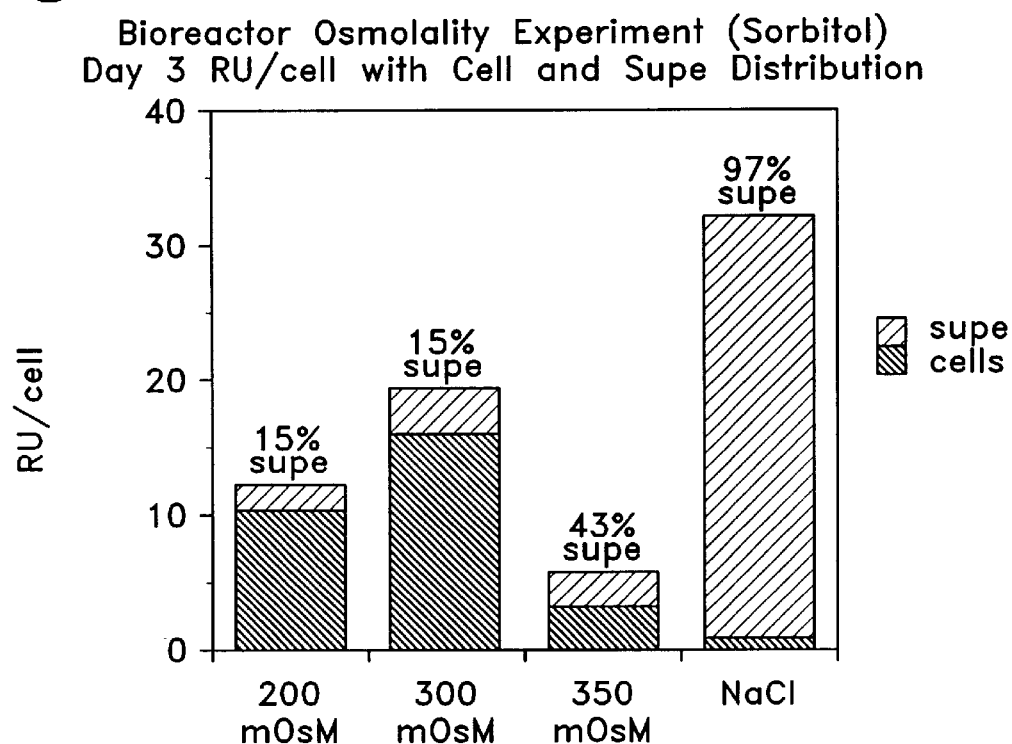

The data evaluating the amount of vector released into the media (by DRPs) show that more DRPs are released into the media when NaCl is used to formulate the media rather than sorbitol (e.g., 27% vs. 4% on day 2; 48% vs. 23% at day 3) (FIGS. 35A and 35B). In terms of RUs, NaCl-formulated cultures released more rAAV at both day 2 and 3 (FIGS. 35C and 35D).

Amount of rAAV released as indicated by RUs shows that more rAAV vector per cell is released into the medium in the cultures formulated with NaCl as opposed to sorbitol as well as the majority of infectious rAAV vector (FIG. 36). 98% or 105.8 RUs were produced per cell in cultures with a starting formulation of 300 mOsm NaCl at day 3 compared to 43% or 3.6 RUs per cell for 350 mOsm starting sorbitol formulated cultures (FIG. 36).

Figure 37C:
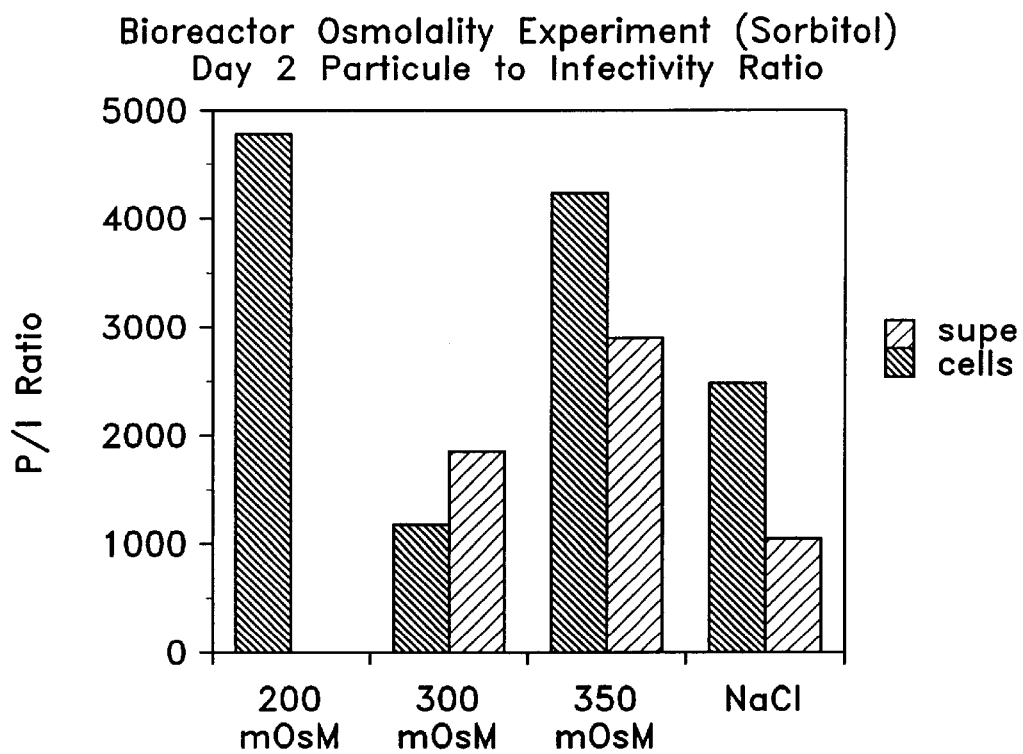
Figure 37D:
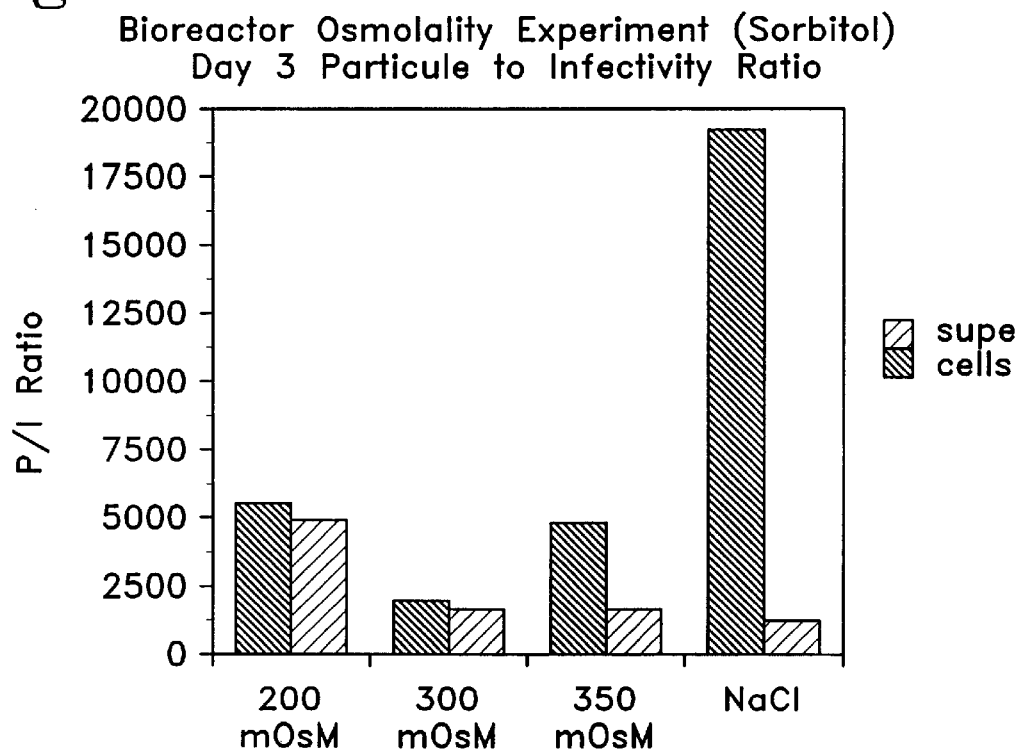

P/I data indicate that the majority of the rAAV vector released into the cell culture medium is infectious (FIG. 37).

As indicated in FIGS. 33A, 33B 34A and 34B, the increase in rAAV vector released into culture medium for NaCl formulated cultures as opposed to sorbitol formulated cultures was not due to a significant difference in metabolic rate (glucose consumption), total cell density, or osmolality of the cultures as there were no appreciable differences in the cultures. However, the cultures did differ in their conductivity (Table 12). Compare, for example, the NaCl formulation at a starting osmolality of 250 mOsm with a conductivity of 10.00 mS that increased to 13.29 mS by day 3 to the sorbitol 300 mOsm starting formulation with a conductivity of 7.11 mS that increased to 10.29 mS by day 3. Generally, the NaCl formulations demonstrating a range of conductivities between approximately 10 and 15 mS demonstrate the greatest percentage release of rAAV vector into the supernatant.

Table 13 is an example of cell culture medium suitable for propagating, maintaining and/or expanding producer cells prior to infection with helper virus (i.e., suitable for maintaining seed train for production).

TABLE 13

Culture Medium, 1 Liter Bottle

| Component | mg/L |
|---|---|
| $CuSO_4 * 5H_2O$ | 0.0013 |
| $Fe(NO_3)_3 * 9H_2O$ | 0.05 |
| $FeSO_4 * 7H_2O$ | 0.42 |
| KCl | 311.8 |
| $NaHCO_3$ | 2200 |
| $Na_2HPO_4 * 7H_2O$ | 134.11 |
| $NaH_2PO_4 * H_2O$ | 62.5 |
| $ZnSO_4 * 7H_2O$ | 0.43 |
| glucose | 4500 |
| HEPES | 3575 |
| hypoxanthine monosodium | 2.4 |
| linoleic acid | 0.04 |
| lipoic acid | 0.1 |
| putrescine * 2HCl | 0.08 |
| sodium pyruvate | 55 |
| thymidine | 0.4 |
| d-biotin | 0.0037 |
| calcium pantothenate | 1.0 |
| choline chloride | 9.0 |
| folic acid | 2.7 |
| inositol | 12.6 |
| nicotinamide | 2.0 |
| pyridoxal HCl | 2.0 |
| pyridoxine HCl | 0.031 |
| riboflavin | 0.22 |
| thiamine HCl | 2.2 |
| vitamine B12 | 0.68 |
| F-68 | 1100 |
| L-alanine | 4.6 |
| L-arginine HCl | 274 |
| L-asparagine * $H_2O$ | 22.5 |
| L-aspartic acid | 20 |
| L-cysteine HCl * $H_2O$ | 17.56 |
| L-cystine * 2HCl | 52.29 |
| L-glutamic acid | 22 |
| L-glutamine | 657 |
| glycine | 26.2 |
| L-histidine HCl * $H_2O$ | 73.4 |
| L-isoleucine | 107 |
| L-leucine | 111.4 |
| L-lysine HCl | 163.8 |
| L-methionine | 32.4 |
| L-phenylalanine | 68.4 |
| L-proline | 17.25 |
| L-serine | 36.8 |
| L-threonine | 101 |
| L-tryptophan | 19.2 |
| L-tyrosine | 91.7 |
| L-valine | 99.6 |

TABLE 13-continued

Culture Medium, 1 Liter Bottle

| Component | mg/L |
|---|---|
| Osmolality | 300 |
| pH | 7.1 |

Example 20

Assaying Viral Titers and High-Throughput Assay Techniques

The temperature-sensitive and wild-type adenovirus stocks used in the preceding examples were produced in 293–1 cells in tissue culture flasks. In this example, the levels of adenovirus being produced by 293–1 cells was quantified by $TCID_{50}$ endpoint assay or infectivity assay.

The $TCID_{50}$ assay was conducted as follows: $1.0 \times 10^3$ 293–1 cells were plated into 96-well microtiter plates and infected with serial dilutions of adenovirus stock and allowed to incubate at 37° C. in a humidified 5% $CO_2$ incubator. Eight replicates of 100 µl of each dilution were inoculated onto the cells. Three days after infection the cells were methanol fixed, washed with PBS and stained with FITC-conjugated anti-hexon antibody (Biodesign) followed by propidium iodide staining to visualize cell nuclei. After rinsing with PBS, the plate was examined under a fluorescent microscope and scored for the presence of hexon containing cells. Titer at endpoint was calculated using a Poisson distribution. A dilution of virus that yields 50% of replicate samples hexon positive has 0.5 IU/100 µl inoculum. Infectious titer is the product of the reciprocal of this dilution, 0.5 IU/100 µl and 10 (conversion factor to ml) to give the final infectious titer per ml.

A high-throughput microtiter infectivity assay to measure infectious virus was conducted as follows. Aliquots (10 µl) of serially diluted cell-free supernatants were inoculated onto HeLa cells grown in 96-well microtiter plates. After three days, infected cells were treated and lysed with a denaturation solution (addition of 1/10th volume of 4.0 M NaOH, 10 µg/ml salmon sperm DNA and 100 mM EDTA). Lysate was transferred to a Silent Monitor BiodyneB plate (Pall) and vacuum filtered onto the nylon membrane. The membrane was washed, denatured, hybridized with $^{32}$P-labeled adenovirus E1A cDNA restriction fragment and analyzed on a phosphorimager (Molecular Dynamics). Linear regression analysis of serially diluted adenovirus standards was used to calculate infectious adenovirus titers in samples, using adenovirus standards titered by the $TCID_{50}$ assay.

Specific virus productivity was calculated by normalizing infectious virus titers in the lysate to cell numbers at the time of infection. Results are shown in Table 14:

TABLE 14

| Adenovirus Production | | | |
|---|---|---|---|
| Adeno-virus | Cell line | Specific productivity (IU/cell) | Assay |
| Ad5 | 293-1 | 125 | $TCID_{50}$ |
|  | HeLa S3 | 400 | $TCID_{50}$ |
| Ad5ts149 | 293-1 | 10 | $TCID_{50}$ |

TABLE 14-continued

| Adenovirus Production | | | |
|---|---|---|---|
| Adeno-virus | Cell line | Specific productivity (IU/cell) | Assay |
|  | 293-1 | 16 | microtiter infectivity |
|  | 293-1 | 15 | microtiter infectivity |
|  | 293-1 | 10 | microtiter infectivity |

These results show that specific production of Adts149 in 293–1 cells was one to two logs lower than Ad5.

An Ad5 virus preparation of known titer showed a linear range extending from 12.5 to 500 IU/well based on linear regression in the microtiter infectivity assay.

Combining a viral infectivity assay with a microtiter array format as described above resulted in a technique which is both rapid and quantitative, and which is highly suitable to automation.

The high-throughput infectivity assay as described above can also be applied to assaying other viruses (e.g., rAAV and wtAAV). The assay can be performed essentially as described above using appropriate mammalian cells (e.g., HeLa C37 cells for rAAV or 293 cells for wtAAV) and under conditions permissive for the replication of the virus to be assayed (e.g., in the presence of helper virus for rAAV and wtAAV); and then lysates can be prepared and nucleic acids in said lysates can be transferred to a membrane as described above. Hybridization of the membrane containing the array of bound nucleic acid pools (each pool being released from the cells of the corresponding culture well) is typically performed with a suitable virus-specific probe (e.g., a probe specific for AAV rep and/or cap might be used to detect wtAAV, or a probe specific for an inserted transgene might be used in the case of a recombinant AAV vector).

The above-described high-throughput infectivity assay exhibited a linear response in the determination of rAAV titers over a relatively broad range of concentrations. For example, when a viral preparation of known titer (as determined by a modified infectious center assay) was serially diluted 1:2, starting from 2400 infectious units or "IU"/well, and used as a standard for the titer determination of two purified tgAAVCF preparations of unknown titer each of which was serially diluted 1:5, the microtiter assay showed a linear range extending from 75 to 600 IU/well based on linear regression. The determination of the titer of wtAAV preferably employed a limiting dilution format (for example, when eight serial limiting dilutions of a wtAAV preparation of known titer were assayed, the titer determined by the microtiter assay was essentially the same as that determined by the standard $TCID_{50}$ assay, $3 \times 10^9$ IU/ml).

Either with limiting dilution or by comparison to a known standard, an infectious virus titer can be determined which corresponds to the titers determined by more classical techniques (e.g., the infectious center assay or the $TCID_{50}$ 50% end-point analysis). Besides its use in the determination of viral titers, this high-throughput infectivity assay has many others uses, including, but not limited to, the screening of cell lines permissive or non-permissive for viral replication and infectivity (e.g. by including various mammalian cells or variants thereof in different wells of a microtiter array); as well as the screening of agents that affect viral infectivity and/or replication (e.g. by including various agents in different wells of a microtiter array as described above and determining the effect of the agents on the resulting infectious titer of virus). Among other things, the ability to rapidly screen for agents or conditions that enhance viral infectivity and/or replication is particularly useful in the context of developing or optimizing the production of viral vectors. Conversely, the ability to rapidly screen for agents or conditions that repress viral infectivity/replication is quite useful in the context of identifying anti-viral therapeutics.

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention, which is delineated by the appended claims.

We claim:

1. A method of generating a population of recombinant adeno-associated virus (rAAV) particles, comprising the following steps:
   a) incubating producer cells in a cell culture medium under conditions comprising a condition that promotes release of rAAV particles into the medium without lysing the cells, wherein the producer cells comprise:
      (i) one or more packaging genes, wherein each said AAV packaging gene encodes an AAV replication or encapsidation protein;
      (ii) a recombinant AAV (rAAV) vector that comprises a heterologous non-AAV polynucleotide flanked by at least one AAV inverted terminal repeat (ITR); and
      (iii) helper virus function for AAV, whereby rAAV virus particles are released from the producer cells into the cell culture medium, and
   b) harvesting the rAAV Particles from the cell culture medium without lysing the cells.

2. The method of claim 1, wherein the condition that promotes release of virus particles is pH.

3. The method of claim 2, wherein the pH is about 7.4 to about 8.0.

4. The method of claim 3, wherein the pH is about 8.0.

5. The method of claim 1, wherein the condition that promotes virus release is incubating cells under sublethal osmotic stress.

6. The method of claim 5, wherein said condition that promotes virus release is incubating producer cells in culture medium that has an osmolality of about 333 mOsm.

7. The method of claim 6, wherein the initial pH of the culture medium is about 8.00.

8. The method of claim 7, wherein the pH of the culture medium is monitored during culture and maintained at about 8.00.

9. The method of claim 8, wherein the pH is adjusted using a sodium base.

10. The method of claim 6, wherein the osmolality of the cell culture medium is adjusted using an ionic salt.

11. The method of claim 10, wherein the ionic salt is NaCl.

12. The method of claim 6, wherein the initial osmolality of the cell culture medium is about 300 mOsm.

13. The method of claim 12, wherein the pH is about 8.00.

14. The method of claim 12, wherein the osmolality of the culture medium is monitored during culture and maintained at about 200 to about 400 mOsm using an ionic salt.

15. The method of claim 14, wherein the ionic salt is NaCl.

16. The method of claim 1, wherein the condition that promotes virus release is temperature.

17. The method of claim 16, wherein the temperature is about 37° C. to about 40° C.

18. The method of claim 17, wherein the temperature is about 39° C.

19. The method of claim 8, wherein the temperature is about 39° C.

20. The method of claim 19, wherein the osmolality is about 300 to about 350 mOsm.

21. The method of claim 12, wherein the temperature is about 39° C.

22. The method of claim 1, wherein the condition that promotes release of virus particles is conductivity.

23. The method of claim 22, wherein the conductivity is at least about 10 mS.

24. The method of claim 22, wherein the conductivity is about 10 mS.

25. The method of claim 22, wherein the conductivity is about 15 mS.

26. The method of claim 22, wherein the conductivity is adjusted using a sodium salt.

27. The method of 26, wherein the sodium salt is NaCl.

28. The method of claim 8, wherein producer cells are cultured for about 48 to about 96 hours after introduction of helper virus function.

29. The method of claim 18, wherein producer cells are cultured for about 48 to about 96 hours after introduction of helper virus function.

30. The method of claim 11, wherein helper virus function is provided by helper virus.

31. A method of generating a population of rAAV particles according to claim 30, wherein said helper virus is an adenovirus.

32. The method of claim 1, further comprising the steps of:
   c) chromatographing the AAV producer cell culture medium on a positively-charged anion exchange resin; and
   d) purifying the chromatographic fractions containing rAAV particles of step c) by cation exchange chromatography or tangential flow filtration to generate a purified population of rAAV vector particles.

33. The method of claim 32, wherein step (d) is cation exchange chromatography.

34. The method of claim 1, further comprising the steps of
   c) chromatographing the AAV producer cell culture medium on a negatively-charged cation exchange resin;
   d) purifying the chromatographic fractions containing rAAV particles of step c) by anion exchange chromatography; and
   e) purifying the chromatographic fractions containing rAAV particles of step d) by cation exchange chromatography to generate a purified population of rAAV vector particles.

35. The method of claim 34, wherein the chromatography of step e) is performed using heparin sulfate.

36. A method of generating a population of rAAV particles according to claim 1, wherein said rAAV vector comprises a heterologous non-AAV polynucleotide flanked by two AAV inverted terminal repeats (ITRs).

37. A method of generating a population of rAAV particles according to claim 1, wherein said AAV producer cell comprises at least one AAV packaging gene that is stably integrated into the genome of said AAV producer cell.

38. A method of generating a population of rAAV particles according to claim 1, wherein said AAV producer cell comprises an AAV rep gene and an AAV cap gene.

39. A method of generating a population of rAAV particles according to claim 38, wherein said AAV rep gene and AAV cap gene are stably integrated into the genome of said AAV producer cell.

40. A method of generating a population of rAAV particles according to claim 1, wherein the producer cell is an attachment-dependent mammalian cell line.

41. A method of generating a population of rAAV particles according to claim 1, wherein the producer cell is a suspension-adapted mammalian cell line.

* * * * *

UNITED STATES PATENT AND TRADEMARK OFFICE
CERTIFICATE OF CORRECTION

PATENT NO. : 6,566,118 B1 Page 1 of 1
DATED : May 20, 2003
INVENTOR(S) : Edward M. Atkinson et al.

It is certified that error appears in the above-identified patent and that said Letters Patent is hereby corrected as shown below:

Column 1,
Line 56, please replace "$1^{10}$" with -- $10^{10}$ --.

Column 21,
Line 41, please replace "WO96117947" with -- WO 96/117947 --.

Column 42,
Line 18, please replace "Na+" should be -- $Na^+$ --.

Column 48,
Lines 6-7, please replace "RAAV" with -- $_R$AAV --.

Column 57,
Line 64, please replace "Ad5" with -- Ad 5 --.

Column 73,
Line 32, please replace "Particles" with -- particles --.
Line 44, please replace "333" with -- 300 --.

Column 74,
Line 28, please replace "claim 11" with -- claim 1 --.

Signed and Sealed this

Twentieth Day of January, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,566,118 B1
DATED : May 20, 2003
INVENTOR(S) : Edward M. Atkinson et al.

It is certified that error appears in the above-identified patent and that said Letters Patent is hereby corrected as shown below:

Column 74,
Line 5, please replace "claim 19" with -- claim 5 --.

Signed and Sealed this

Eighteenth Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO.     : 6,566,118 B1
DATED          : May 20, 2003
INVENTOR(S)    : Edward M. Atkinson et al.

It is certified that error appears in the above-identified patent and that said Letters Patent is hereby corrected as shown below:

Column 74,
Line 5, please replace "claim 19" with -- claim 5 --.

Signed and Sealed this

Eighth Day of June, 2004

JON W. DUDAS
*Acting Director of the United States Patent and Trademark Office*